US006849449B2

(12) United States Patent
Owyang

(10) Patent No.: US 6,849,449 B2
(45) Date of Patent: Feb. 1, 2005

(54) ORPHANIN FQ RECEPTOR NUCLEIC ACIDS

(75) Inventor: Chung Owyang, Ann Arbor, MI (US)

(73) Assignee: Regents of the University of Michigan, Ann Arbor, MI (US)

( * ) Notice: Subject to any disclaimer, the term of this patent is extended or adjusted under 35 U.S.C. 154(b) by 75 days.

(21) Appl. No.: 10/087,345

(22) Filed: Mar. 1, 2002

(65) Prior Publication Data

US 2003/0045696 A1 Mar. 6, 2003

Related U.S. Application Data

(60) Provisional application No. 60/272,429, filed on Mar. 1, 2001.

(51) Int. Cl.[7] .......................... C12N 15/85; C12N 5/00; A01K 67/027; C07H 21/04
(52) U.S. Cl. ................. 435/325; 435/320.1; 435/252.3; 800/8; 536/23.5
(58) Field of Search .............................. 435/320.1, 325, 435/252.3; 536/23.5, 235; 800/8

(56) References Cited

U.S. PATENT DOCUMENTS

| | | | |
|---|---|---|---|
| 4,657,760 A | 4/1987 | Kung et al. ................... 424/85 |
| 4,683,195 A | 7/1987 | Mullis et al. .................. 435/6 |
| 4,683,202 A | 7/1987 | Mullis ......................... 435/91 |
| 4,873,191 A | 10/1989 | Wagner et al. ............ 435/172.3 |
| 4,946,778 A | 8/1990 | Ladner et al. .............. 435/69.6 |
| 4,965,188 A | 10/1990 | Mullis et al. ................. 435/6 |
| 5,096,815 A | 3/1992 | Ladner et al. .............. 435/69.1 |
| 5,198,346 A | 3/1993 | Ladner et al. .............. 435/69.1 |
| 5,206,344 A | 4/1993 | Katre et al. ................. 530/351 |
| 5,223,409 A | 6/1993 | Ladner et al. .............. 435/69.7 |
| 5,225,212 A | 7/1993 | Martin et al. ................ 424/450 |
| 5,614,396 A | 3/1997 | Bradley et al. ........... 435/172.3 |
| 5,674,713 A | 10/1997 | McElroy et al. ........... 435/69.7 |
| 5,733,731 A | 3/1998 | Schatz et al. .................. 435/6 |
| 5,811,238 A | 9/1998 | Stemmer et al. ............... 435/6 |
| 5,821,067 A | * 10/1998 | Grandy et al. ............... 435/7.2 |
| 5,821,219 A | 10/1998 | Grandy et al. ................. 514/2 |
| 5,830,721 A | 11/1998 | Stemmer et al. ......... 435/172.1 |
| 5,837,458 A | 11/1998 | Minshull et al. ............... 435/6 |
| 5,837,809 A | 11/1998 | Grandy et al. .............. 530/326 |
| 5,866,324 A | * 2/1999 | Eppler et al. .................. 435/6 |
| 5,929,035 A | 7/1999 | Owyang ....................... 514/13 |
| 5,976,796 A | 11/1999 | Szalay et al. .................. 435/6 |
| 5,976,807 A | 11/1999 | Horlick et al. ................. 435/6 |
| 6,074,859 A | 6/2000 | Hirokawa et al. ........... 435/189 |
| 6,080,912 A | 6/2000 | Bremel et al. ................ 800/23 |
| 6,103,492 A | * 8/2000 | Yu ............................ 435/69.1 |

FOREIGN PATENT DOCUMENTS

| | | |
|---|---|---|
| WO | WO 84/03564 | 9/1981 |
| WO | WO 90/08832 | 8/1990 |
| WO | WO 93/03367 | 2/1993 |

OTHER PUBLICATIONS

Entrez Nucleotide Database Accession No. U05239.1 (GI:45183), published 1994.*
Wall, R.J. (1996) Theriogenology 45:57–68.*
Pan et al. Identification and differential regional expression of KOR–3/ORL–1 gene splice ... variants in mouse brain. FEBS Lett. Sep. 11, 1998;435(1):65–8.*
Chen et al. Molecular cloning, tissue distribution and chromosomal localization of a novel ... member of the opioid receptor gene family, FEBS Lett. Jun. 27, 1994;347(2–3):279–83.*
Pan et al. Cloning and functional characterization through antisense mapping of a kappa ... 3–related opioid receptor. Mol Pharmacol. Jun. 1995;47(6):1180–8.*
Bunzow et al. Molecular cloning and tissue distribution of a putative member of the rat ... opioid receptor gene family that is not a mu, delta or kappa opioid receptor. type. FEBS Lett. Jun. 27, 1994;347(2–3):284–8.*
Wick et al. Isolation of a novel cDNA encoding a putative membrane receptor with high homology to the cloned mu, delta, and kappa opioid receptors. Brain Res Mol Brain Res. Nov. 1994;27(1):37–44.*
Doetschman T. Interpretation of phenotype in genetically engineered mice ... Lab Anim Sci. Apr. 1999;49(2):137–43.*
Sigmund C.D. Viewpoint: are studies in genetically altered mice out of control? Arterioscler Thromb Vasc Biol. Jun. 2000;20(6):1425–9.*
Mogil et al. The molecular and behavioral pharmacology of the orphanin FQ/nociceptin peptide ... and receptor family, Pharmacol Rev. Sep. 2001;53(3):381–415.*
Brownstein, Proc. Natl. Acad. Sci. USA 90:5391 [1993].
DiChara and North, Trends in Pharamcol. Sci. 13:185 [1992].
Wang et al., FEBS Lett. 348:75 [1994].
Darland et al., Trends Neurosci. 21:215 [1998].
Mollereau et al., FEBS Lett. 341:33 [1994].
Fukuda et al., FEBS Lett. 343:42 [1994].
Bunzow et al., FEBS Lett. 347:284 [1994].
Lachowicz et al., J. Neurochem. 64:34 [1995].
Nishi et al., Biochem. Biophys. Res. Commun. 205:1353 [1994].

(List continued on next page.)

Primary Examiner—David Guzo
Assistant Examiner—Daniel M. Sullivan
(74) Attorney, Agent, or Firm—Medlen & Carroll, LLP

(57) ABSTRACT

The present invention provides Orphanin FQ receptor nucleic acid sequences. Specifically, the present invention provides nucleic acid sequences of differentially expressed splice variants of the Orphanin FQ receptor. The present invention also provides methods of using the Orphanin FQ receptor nucleic acid sequences for the identification of pharmaceutical agents and the generation of animal models of Orphanin FQ receptor-mediated disease states. The present invention thus provides improved method of screening potential therapeutics useful in the treatment of a variety of disease states mediated by Orphanin FQ signaling.

3 Claims, 22 Drawing Sheets

OTHER PUBLICATIONS

Pan et al., Regul. Pept. 54:217 [1994].
Pan et al., Gene 171:255 [1996].
Reinscheid et al., Science 270:792 [1995].
Meunier et al., Nature 377:532 [1995].
Zhang et al., Brain Res. 772:102 [1997].
Yazdani et al., Gastroenterology 116:108 [1999].
Osinski et al., Eur. J. Pharmacol. 365:281 [1999].
Rossi et al., J. Pharamcol. Exp. Ther. 282:858 [1997].
Rossi et al., Brain Res. 792:327 [1998].
Noda et al., J. Biol. Chem. 273:18047 [1998].
Pan et al., FEBS Lett. 395:207 [1996].
Mathis et al., Biochem. Biophys. Res. Commun. 230:462 [1997].
Yamamoto and Nozaki–Taguchi, Anesthesiology 87:1145 [1997].
Blandizzi et al., Biochem. Biophys. Res. Commun. 202:947 [1994].
Mount, Nucleic Acids Res. 10:459 [1982].
Muraoka et al., Am. J. Physiol. 271:G1101 [1996].
Song et al., Proc. Natl. Acad. Sci. U S A 90:9085 [1993].
Calo et al., Br. J. Pharmacol 129:1261 [2000].
Jenck et al., PNAS 97:4938 [2000].
Koster et al., PNAS 96:10444.
Allen et al., J. Neurosci., 19:2152 [1999].
Meng et al., J. Biol. Chem., 275:21939 [2000].
Takahashi et al., Gastroenterology 119:1054 [2000].
Takahashi et al., Gastroenterology 119:71 [2000] (abstract only).
Hashimoto et al., Neurosci. Lett. 278:109 [2000] (abstract only).
Hom et al., Synapse 34:187 [1999] (abstract only).
Goda and Mutneja, Curr. Biol., 8:R889 [1998] (abstract only).
Guerrini et al., J. Med. Chem., 43:2805 [2000] (abstract only).
Chiou, J. Biomed Sci. 7:232 [2000] (abstract only).
Berger et al., J. Pharmacol. Exp. Ther. 294:428 [2000] (abstract only).

* cited by examiner

Figure 2

Figure 6
SEQ ID NO:9

```
   1   tgtgtgcccg tctgccaatt taagcatgtt accagcattc ccatcgtttc caaatgctga
  61   gcccttgaga ctcggagacg cacgtgaaag actactttag ggatatagag actctgtacg
 121   aggtgcagga actctctggg ggtttgtgtg ccagcttttg ccgggggtgg catggggatg
 181   aaaaaggaag tgatggaagg gcagggagag agagagagag agagagagag agagagagag
 241   agagagagag agagagagca acagagagtg catacttatg tgctatatat ctaggggcct
 301   ttctctgttc ttgcctgttc ccacactagt tcacatcttg tttgtatctt tctctttgtg
 361   cctgaatgca ccttgtgggt tgtatatgtg atccttgtgt gcatctctga gcacatatcc
 421   cttgtgtctc tgtatctcta aactgtgcct gtctgggtac ctcttgtat gttctgttta
 481   tttgcaggaa tgtgtcctca tgtgtctcct tgagtgtcca tgtgtctccg agaacggaga
 541   gacaagtcct tggagacagc ttgggatgct gagtcctggg gtgtctgtct gctctggcct
 601   tttctggttg gacaggtatc ctagcaacac ttctgtgagt tgcctagcaa ccaggtcccc
 661   atccttagag aaagagcagg gtctggctgt atgtgggagg tctggctctc attcagtcca
 721   gacaggaaaa acaaacctat gatttgatga tgactagaga ctcagcatag ggtccctagc
 781   ctacatgacc ttaacttatg gttttttttct cagtggactg tgctccccca ccccaccccc
 841   cccgtgctgg caaagaagga ggtccctagg agcttagtat ctctgtgttt tctaagatct
 901   aattctggga tttggctgtg gtgtagcttc aagtgaccag caaacctggc ttcccccttat
 961   ccctgccatg ttgacaggca gctccagact tcagaggcgt gatgctttca tttgtgtgag
1021   gataatatgg gtggcagtgg ccatgtgtag tgggggttcc tgggttcagt tttgtcttga
1081   gcttagtgca cattaggtat aaacagcaca tagtagactc agggcagtgc tgggtccaca
1141   gtccagacaa tctcttgttt attcgcaaga aggcctttac atggagaatt agttgggtca
1201   ggatattgct atcactgtgg tactctaccc tattggacac cggctgaggg cagttctggg
1261   taggaaagct agcaaaatct ggtctgtgct cagtggtggt agcacatgcc tttaatccta
1321   gcattcagga agcagaggca gatgtgtctc taagttctag gacagccaag gctacacaga
1381   caaatcctgt ctctaacctg ttaacttccc caaacaaaac aaaacaaaac agagcaaagc
1441   aaagcaaagc aaaacaaaac aaaacaacat tttcgagtgt tggagcctca cgtctacttc
1501   tgggtgagca tttctctgta tacatcttga atgtgttctt gtgtctaagg ctgtgcgtgt
1561   atgtgtgtct gaattcctgt tcatgtctct attttgtgt tcatggatgt ccccattgtg
1621   tgtcctaggg cctgagtgtg tttgtgttgg gtgagcccat cacattatat gtttgttaat
1681   cttttggctc ctacttggtg tggagcctag gggttctggt ctggtaatct tcctttttt
1741   ttttttttt tggcttcctt ctccaacctg cacagcccct ccttctctca gccgcagcct
1801   tctgcccctc cccttctgg ctgccgcacc ggctgctgcg tctagtcaat atcttatctt
1861   ccgagcagga gctaggagcc attcccagcc gcagcagacc ccaatctaga gtgagagtca
1921   ttgctcagtc cactgtgctc ctgcctgccc gcctttctgc taagcattgg ggtctatttt
1981   ggcccagctt ctgaagaggc tgtgtgtgcc gttggaggta agaggggctc ctgctgcctc
2041   tgacagagct gggggtgggg gagccctggg aggtagctat gtgaagtgcc tgagccttag
2101   gcatttctgg ataaattcca tgccttttgt gccccagtgt accttaggat ggtttaggca
2161   ttttttgtgt ttggctggct gtgagcccct gggtcttggt gggtggacat gtgtgcttgt
2221   gtagctacgt tgcttctgtg cgggtctata accctaatgt gaggtaacct tgtaggtaaa
2281   tgtgcccca tgcctctgtg tgtgtcacca tgtgcccacg ggcatgtctg cctttgtctg
2341   tgtccgtgtg tctgtgtgtg tgcctagtca ttgtgcatgc tcatggaggc gttcatgtgc
2401   ctgttagtgt agttgtgctg tgttctaagg cctcagtgga cggtgtctag cactgtggtt
2461   acttgtttct gtgccctgtt ccaggaactg tactgagtgg cttttgcaggg tgacagcatg
2521   gagtccctct ttcctgctcc atactgggag gtcttgtatg gcagccactt tcaagggaac
2581   ctgtccctcc taaatgagac cgtaccccac cacctgctcc tcaatgctag tcacagcgcc
2641   ttcctgcccc ttggactcaa ggtcaccatc gtggggctct acttggctgt gtgcatcggg
2701   gggctcctgg ggaactgcct cgtcatgtat gtcatcctca ggtaggctgg gccccatcag
2761   tctgtgaagg gggaacctga ggcaggaggc tgttctgggt gaatctgaac aagtatggat
2821   tttctgcttg ctccatcaaa tttctttcct ctctgttcaa gggcatgac caccttgaa
2881   gttcaactcc tgttctgtcc ccatctgtct cagactaggt ggaggcttgg agctgcagat
2941   aaattcatgc catgatgtct gtgtgaataa cctcatgggt acacaggatc ctaggatttc
3001   tcaaacagag gaagagggc tggtgctggg cctgaagctc ttattcattg acttttggga
```

Figure 6 (cont.)

```
3061  tctctattca tggtggatgt ctttagctga gcccatgctc tattggtgct cagaaatatg
3121  aaaatttgga ggactagaaa gaaaggcagc agtactgggc aactgagtca gagtcaacag
3181  tgaggggata ctggagggag cagtatgagg tgcagttctg tggacacaaa agctggacaa
3241  ggagtatgca attggtaaaa tgtgtcacgg caatgatggt ctctgttttt ttccagctgg
3301  gagggcattg aggggactg gagacagcag gtgaggactt gaatgccaga atggggacat
3361  tgggaagaca tgggaggtcc ttgaatggtg aataactaga gcaaggttct tcactgatat
3421  atttcctctt tcaaaaagat gactctgaag aaagcagtca tggtcccctt gatgtatca
3481  tggtaggtgt ggtggtggtg gagaaagggc agtgcaggtt ctatattctg cctcatcacg
3541  atcctcttag tattcctgag caactgtttt ctccattcgt tagatgggaa atatggatta
3601  cataaccata tataggtgca tgtgcataca cgtgtatata gtaatatt gatatgtgat
3661  tggacagtgt agtaggaaaa gccttccaag tactgacttt cagcagagga tccttgtggg
3721  aaactattct atgatctaag tgttagagga tattcatctt tggcaagaag tgcagcaacc
3781  tgggacagtt tgtgagcctt gccttccctt cttgtcctca gcatttctct cccatattta
3841  ctgcatcagg gcagacaagg agcaccatct tttccagtag catcctcaga gagctagtct
3901  caggaactgc tgtggccaca ctggctctgg aggcaaaaca cggcgtgttt gagttggcat
3961  acgccaggag tcagaaaaac ctgctctgag ccccatttg caccttcgca gttccaagcc
4021  ttataaaagc tacttacgtc ctccgagcct cagcttcctt ctctgcagcc tagggatcta
4081  atagcatttt ttcttttggg gtaaacctca aatgagataa aatctacgtg aagagcttgg
4141  ctcagatatc taccattatc gttgttattg ttgtttattg tagttaaggt ctctaggatt
4201  aatgtctaag aaacagaact taatcccaga ttccctgata gcaactaaac tatcatggac
4261  tactgttacc tctagttcta tcactaccat accaccataa ccactctaac caccaccacc
4321  accaccatca ctataatcac ccttccctac cgctatcata aacattaatt cattccacta
4381  atatttatca cttataatgt ccctagcatg gttcccggtg cttggataca tcaaacctaa
4441  ctagcacatc tcttgttttc tttattagaa ttaaaaata aattatgttt atttatgtgt
4501  ctgtgtatgt ctgtctggat gtgtaggtca gaggagaaag ttgggtttct ccttttacca
4561  tgtaagtttc tccttctacc acatgcgtcc tggagataga actcaggttg tcagaattgg
4621  tagtaagtgc ccttaccggc tgagccattt ggctggccca gcattgtctg ttttcattgc
4681  tagacaatac tgtgcagttg gaagacacag atctttgatg aactttacag gcagtgccct
4741  gaaaagcctc tgagagaagt cttaagagag actgaggaga gaagacagca tctctctctc
4801  ttgattcatt ccacaaactc acattcaggt tagaatgca ctcaggtact cctccatgcc
4861  cccaactttt ccagggtagt cttgtcattg atttggaacc tttctgtaga tgtcatagtc
4921  acatggggaa gcttgttaaa gtcccaggct cagtggactt tgggtgtggt gcaggatctg
4981  ccatttaata agcttccttg gagactctgg ggttgagaga ttcaaagacc ataaccctct
5041  tggtggtccc ttagctgcca agtctacgca aaatggccaa atggagcctt tcttctcctt
5101  gtcctctaca ggcacaccaa gatgaagaca gctaccaaca tttacatatt taatctggca
5161  ctggctgata ccctggtctt gctaacactg cccttccagg gcacagacat cctactgggc
5221  ttctggccat ttgggaatgc actctgcaag actgtcattg ctatcgacta ctacaacatg
5281  tttaccagca cttttactct gaccgccatg agcgtagacc gctatgtggc tatctgccac
5341  cctatccgtg cccttgatgt tcggacatcc agcaaagccc aggctgttaa tgtggccata
5401  tgggcctgg cttcagtggt tggtgttcct gttgccatca tgggttcagc acaagtggaa
5461  gatgaaggtc agtgggtggt cctcctccct gactcattag tttcccatgg ttcttgctgg
5521  tccctctgac cccatttctc tcctgcagag atcgagtgcc tggtggagat ccctgcccct
5581  caggactatt ggggccctgt attcgccatc tgcatcttcc ttttttcctt catcatccct
5641  gtgctgatca tctctgtctg ctacagcctc atgattcgac gacttcgtgg tgtccgtctg
5701  ctttcaggct cccgggagaa ggaccgaaac ctgcggcgta tcactcgact ggtgctggta
5761  gtggtggctg tgtttgtggg ctgctggacg cctgtgcagg tgtttgtcct ggttcaagga
5821  ctgggtgttc agcaggtag tgagactgca gttgccatcc tgcgcttctg cacagccctg
5881  ggctatgtca acagttgtct caatccccatt ctctatgctt tcctggatga gaacttcaag
5941  gcctgcttta gaaagttctg ctgtgcttca tccctgcacc gggagatgca ggtttctgat
6001  cgtgtgcgga gcattgccaa ggatgttggc cttggttgca agacttctga gacagtacca
6061  cggccagcat gactaggcgt ggacctgccc atggtgcctg tcagcccaca gagcccatct
6121  acacccaaca cggagctcac acaggtcact gctctctagg ttgaccctga accttgagca
6181  tctggagcct tgaatggctt ttcttttgga tcaggatgct cagtcctaga ggaagacctt
```

Figure 6 (cont.)

```
6241  ttagcaccat gggacaggtc aaagcatcaa ggtggtctcc atggcctctg tcagattaag
6301  ttccctccct ggtataggac cagagaggac caaaggaact gaatagaaac atccacaaca
6361  cagtggacat gcctggtgag cccatgtagg tattcatgct tcacttgact cttctctggc
6421  ttctccctgc tgccctggct ctagctgggc tcaacctgag gtattgtagt ggtcatgtag
6481  tcactcttgt gactacatgt tgtgtgctgt tgctctcggc ctttcagtat ttccacagga
6541  ctgctgaaca tacctggtat tgcagtgggg agcattaatt ttcttttaaa gtgagactgg
6601  cccttaagct tggcgttgcc ttggagcgtc ttctacttct gacttcactg atgcagtcag
6661  attacccgag ggtgagcatc agtggtttct tggatggctg ttttctgaag attcttccca
6721  tccagtacat ggagtctatg aagggagtca caattcatct ggtactgcca ctacctgctc
6781  tataatcctg ggctatcttc ttggcaagat gacagtgggg gagacaagac acagagcttc
6841  cctaaggctc tttccctcca aaaccactgt gaactcttat cctacagact gttcggcaag
6901  cactgcttct aggtgtgtgg gaggtaatca ggagaaagct tgtggcctc tgtaggctgc
6961  tcacaacatg gaggcaccac atgctggtct tgcctgctta gtacaggcag gacagagcag
7021  aatatgctct ctctcgattc tctacaaact ccctcagttc tccagcagag tctcttttac
7081  ttgctatcag aggtcaggag ttgtactgct agaagcatac ttgtagcttg ggaagagtgg
7141  cagtcaggat gtgttctact ctatatccac agtgaccacc tgcttcatat atagggttag
7201  gacatatctg agtaaggcct gagtgtgctg ccaaattgga ggttggtatg agagctgatg
7261  cctaaagtgg ctcatttgca aggactatta tggtttggaa tagcaatggg cactggtcgg
7321  cgaagaagag tctatacctt cgagatctat ttgatggttc acagaagagg ttttgtcaaa
7381  cgcccttcta tgggtcagat atcaaaatac cagcaacgtt ggatagattc tgaccttta
7441  ctgagacctc ggtcagatgg tttcatgtca tgcagagaac ctaggctggt tcctgtgtca
7501  gagagacctg ggcttctggg gaggccaggg ttcttccttt gacacttgtg cgggacgcgt
7561  tagctctaga gttttcttgc taatgctaag aaactttgtg aatttgtata tctttatgta
7621  tttaagcatg caacaagcgt catttccatg catgtagcta gccctgaacc tgcctctggg
7681  gtaatgaagg agtgctcata acaaacactt atccagtgac cagtactgtc catagcctaa
7741  gtgtttctga ctccagctac ataagagtaa cttcctgggt attgatatgc actgggatga
7801  ggcacagaac caggttcatg ggttttaaac ctgttctgcc cttgcaaggg actttaagga
7861  acttcttgat tgatgggagg aaaactagtt cctgggttgc agaggctgct gcctttcctt
7921  ctcccaagac aatgactatc ttttctcccc acactcagga acagtgggta gatgcctttc
7981  ttcacagttt ttctttgtag actcttgctg cttgagcaaa tctaaaagga gttgtggtga
8041  tcagagcaga ggacccttct ctggtggcag agcaaccccta tgctatagag atctaccccc
8101  tggctcttgt ctgtgtaggc ccaatctggc tcaattgacc ctctggcaga tggcccttat
8161  caggggggct ttgaagaggg tcttacttgc caaagcgctt gctttcagta cagagctggt
8221  gagccaaagc ttggttttat acaagtttta atgacattgt ccatttgttt tttgttttt
8281  agtctagcag tttataatca aaaggtatga atttctaata ggcttaaaag atgcagccca
8341  tgcaggcatg gtggattgga ttctatgaga tt
```

Figure 7
SEQ ID NO:10

```
   1    ctgcacagcc cctccttctc tcagccgcag ccttctgccc ctcccccttc tggctgccgc
  61    accggctgct gcgtctagtc aatatcttat cttccgagca ggagctagga gccattccca
 121    gccgcagcag accccaatct agagtgagag tcattgctca gtccactgtg ctcctgcctg
 181    cccgcctttc tgctaagcat tggggtctat tttggcccag cttctgaaga ggctgtgtgt
 241    gccgttggag gaactgtact gagtggcttt gcagggtgac agcatggagt ccctctttcc
 301    tgctccatac tgggaggtct tgtatggcag ccactttcaa gggaacctgt ccctcctaaa
 361    tgagaccgta ccccaccacc tgctcctcaa tgctagtcac agcgccttcc tgcccttgg
 421    actcaaggtc accatcgtgg ggctctactt ggctgtgtgc atcggggggc tcctggggaa
 481    ctgcctcgtc atgtatgtca tcctcagctg ggagggcatt gagggggact ggagacagca
 541    gacaatactg tgcagttgga agacacagat ctttgatgaa ctttacaggc agtgccctga
 601    aaagcctctg agagaagtct taagagagac tgaggagaga agacagcatc tctctctctt
 661    gattcattcc acaaactcac attcaggcac accaagatga agacagctac caacatttac
 721    atatttaatc tggcactggc tgataccctg gtcttgctaa cactgccctt ccagggcaca
 781    gacatcctac tgggcttctg gccatttggg aatgcactct gcaagactgt cattgctatc
 841    gactactaca acatgtttac cagcactttt actctgaccg ccatgagcgt agaccgctat
 901    gtggctatct gccaccctat ccgtgccctt gatgttcgga catccagcaa agcccaggct
 961    gttaatgtgg ccatatgggc cctggcttca gtggttggtg ttcctgttgc catcatgggt
1021    tcagcacaag tggaagatga agagatcgag tgcctggtgg agatccctgc ccctcaggac
1081    tattggggcc ctgtattcgc catctgcatc ttcctttttt ccttcatcat ccctgtgctg
1141    atcatctctg tctgctacag cctcatgatt cgacgacttc gtggtgtccg tctgctttca
1201    ggctcccggg agaaggaccg aaacctgcgg cgtatcactc gactggtgct ggtagtggtg
1261    gctgtgtttg tgggctgctg gacgcctgtg caggtgtttg tcctggttca aggactgggt
1321    gttcagccag gtagtgagac tgcagttgcc atcctgcgct tctgcacagc cctgggctat
1381    gtcaacagtt gtctcaatcc cattctctat gctttcctgg atgagaactt caaggcctgc
1441    tttagaaagt tctgctgtgc ttcatccctg caccgggaga tgcaggtttc tgatcgtgtg
1501    cggagcattg ccaaggatgt tggccttggt tgcaagactt ctgagacagt accacggcca
1561    gcatga
```

Figure 8
SEQ ID NO:11

MESLFPAPYWEVLYGSHFQGNLSLLNETVPHHLLLNASHSAFLPLGLKVTIVGLYLAVCIGGLLGN
CLVMYVILSWEGIEGDWRQQTILCSWKTQIFDELYRQCPEKPLREVLRETEERRQHLSLLIHSTNSH
SGTPR

Figure 9
SEQ ID NO:12

```
   1   ctgcacagcc cctccttctc tcagccgcag ccttctgccc ctcccccttc tggctgccgc
  61   accggctgct gcgtctagtc aatatcttat cttccgagca ggagctagga gccattccca
 121   gccgcagcag accccaatct agagtgagag tcattgctca gtccactgtg ctcctgcctg
 181   cccgcctttc tgctaagcat tggggtctat tttggcccag cttctgaaga ggctgtgtgt
 241   gccgttggag gaactgtact gagtggcttt gcagggtgac agcatggagt ccctcttcc
 301   tgctccatac tgggaggtct tgtatggcag ccactttcaa gggaacctgt ccctcctaaa
 361   tgagaccgta ccccaccacc tgctcctcaa tgctagtcac agcgccttcc tgcccttgg
 421   actcaaggtc accatcgtgg ggctctactt ggctgtgtgc atcgggggc tcctggggaa
 481   ctgcctcgtc atgtatgtca tcctcagctg ggagggcatt gagggggact ggagacagca
 541   ggcacaccaa gatgaagaca gctaccaaca tttacatatt taatctggca ctggctgata
 601   ccctggtctt gctaacactg cccttccagg gcacagacat cctactgggc ttctggccat
 661   ttgggaatgc actctgcaag actgtcattg ctatcgacta ctacaacatg tttaccagca
 721   cttttactct gaccgccatg agcgtagacc gctatgtggc tatctgccac cctatccgtg
 781   cccttgatgt tcggacatcc agcaaagccc aggctgttaa tgtggccata tgggccctgg
 841   cttcagtggt tggtgttcct gttgccatca tgggttcagc acaagtggaa gatgaagaga
 901   tcgagtgcct ggtggagatc cctgcccctc aggactattg gggccctgta ttcgccatct
 961   gcatcttcct ttttccttc atcatccctg tgctgatcat ctctgtctgc tacagcctca
1021   tgattcgacg acttcgtggt gtccgtctgc tttcaggctc ccggagaag gaccgaaacc
1081   tgcggcgtat cactcgactg gtgctggtag tggtgctgt gtttgtgggc tgctggacgc
1141   ctgtgcaggt gtttgtcctg gttcaaggac tgggtgttca gccaggtagt gagactgcag
1201   ttgccatcct gcgcttctgc acagccctgg gctatgtcaa cagttgtctc aatcccattc
1261   tctatgcttt cctggatgag aacttcaagg cctgctttag aaagttctgc tgtgcttcat
1321   ccctgcaccg ggagatgcag gtttctgatc gtgtgcggag cattgccaag gatgttggcc
1381   ttggttgcaa gacttctgag acagtaccac ggccagcatg a
```

Figure 10
SEQ ID NO:13

MESLFPAPYWEVLYGSHFQGNLSLLNETVPHHLLLNASHSAFLPLGLKVTIVGLYLAVCIGGLLGNCLVMY
VILSWEGIEGDWRQQAHQDEDSYQHLHI

Figure 11
SEQ ID NO:14

```
   1    ctgcacagcc cctccttctc tcagccgcag ccttctgccc ctcccccttc tggctgccgc
  61    accggctgct gcgtctagtc aatatcttat cttccgagca ggagctagga gccattccca
 121    gccgcagcag accccaatct agagtgagag tcattgctca gtccactgtg ctcctgcctg
 181    cccgccttc  tgctaagcat tggggtctat tttggcccag cttctgaaga ggctgtgtgt
 241    gccgttggag gaactgtact gagtggcttt gcagggtgac agcatggagt ccctcttttcc
 301    tgctccatac tgggaggtct tgtatggcag ccactttcaa gggaacctgt ccctcctaaa
 361    tgagaccgta ccccaccacc tgctcctcaa tgctagtcac agcgccttcc tgccccttgg
 421    actcaaggtc accatcgtgg ggctctactt ggctgtgtgc atcggggggc tcctggggaa
 481    ctgcctcgtc atgtatgtca tcctcaggca caccaagatg aagacagcta ccaacattta
 541    catatttaat ctggcactgg ctgatacccct ggtcttgcta acactgccct tccagggcac
 601    agacatccta ctgggcttct ggccatttgg gaatgcactc tgcaagactg tcattgctat
 661    cgactactac aacatgttta ccagcacttt tactctgacc gccatgagcg tagaccgcta
 721    tgtggctatc tgccaccctc tccgtgccct tgatgttcgg acatccagca aagcccaggc
 781    tgttaatgtg gccatatggg ccctggcttc agtggttggt gttcctgttg ccatcatggg
 841    ttcagcacaa gtggaagatg aagagatcga gtgcctggtg gagatccctg cccctcagga
 901    ctattggggc cctgtattcg ccatctgcat cttccttttt tccttcatca tccctgtgct
 961    gatcatctct gtctgctaca gcctcatgat tcgacgactt cgtggtgtcc gtctgctttc
1021    aggctcccgg gagaaggacc gaaacctgcg gcgtatcact cgactggtgc tggtagtggt
1081    ggctgtgttt gtgggctgct ggacgcctgt gcaggtgttt gtcctggttc aaggactggg
1141    tgttcagcca ggtagtgaga ctgcagttgc catcctgcgc ttctgcacag ccctgggcta
1201    tgtcaacagt tgtctcaatc ccattctcta tgctttcctg gatgagaact tcaaggcctg
1261    ctttagaaag ttctgctgtg cttcatccct gcaccgggag atgcaggttt ctgatcgtgt
1321    gcggagcatt gccaaggatg ttggccttgg ttgcaagact tctgagacag taccacggcc
1381    agcatga
```

Figure 12
SEQ ID NO:15

MESLFPAPYWEVLYGSHFQGNLSLLNETVPHHLLLNASHSAFLPLGLKVTIVGLYLAVCIGGLLGNCLVMY
VILRHTKMKTATNIYIFNLALADTLVLLTLPFQGTDILLGFWPFGNALCKTVIAIDYYNMFTSTFTLTAMS
VDRYVAICHPIRALDVRTSSKAQAVNVAIWALASVVGVPVAIMGSAQVEDEEIECLVEIPAPQDYWGPVFA
ICIFLFSFIIPVLIISVCYSLMIRRLRGVRLLSGSREKDRNLRRITRLVLVVVAVFVGCWTPVQVFVLVQG
LGVQPGSETAVAILRFCTALGYVNSCLNPILYAFLDENFKACFRKFCCASSLHREMQVSDRVRSIAKDVGL
GCKTSETVPRPA

Figure 13
SEQ ID NO:16

```
   1    ctgcacagcc cctccttctc tcagccgcag ccttctgccc ctcccccttc tggctgccgc
  61    accggctgct gcgtctagtc aatatcttat cttccgagca ggagctagga gccattccca
 121    gccgcagcag accccaatct agagtgagag tcattgctca gtccactgtg ctcctgcctg
 181    cccgcctttc tgctaagcat tggggtctat tttggcccag cttctgaaga ggctgtgtgt
 241    gccgttggag gaactgtact gagtggcttt gcagggtgac agcatggagt ccctctttcc
 301    tgctccatac tgggaggtct tgtatggcag ccactttcaa gggaacctgt ccctcctaaa
 361    tgagaccgta ccccaccacc tgctcctcaa tgctagtcac agcgccttcc tgccccttgg
 421    actcaaggtc accatcgtgg ggctctactt ggctgtgtgc atcgggggggc tcctggggaa
 481    ctgcctcgtc atgcacacca agatgaagac agctaccaac atttacatat ttaatctggc
 541    actggctgat accctggtct tgctaacact gccccttccag ggcacagaca tcctactggg
 601    cttctggcca tttgggaatg cactctgcaa gactgtcatt gctatcgact actacaacat
 661    gtttaccagc acttttactc tgaccgccat gagcgtagac cgctatgtgg ctatctgcca
 721    ccctatccgt gcccttgatg ttcggacatc cagcaaagcc caggctgtta atgtggccat
 781    atgggccctg gcttcagtgg ttggtgttcc tgttgccatc atgggttcag cacaagtgga
 841    agatgaagag atcgagtgcc tggtggagat ccctgcccct caggactatt ggggccctgt
 901    attcgccatc tgcatcttcc ttttttcctt catcatccct gtgctgatca tctctgtctg
 961    ctacagcctc atgattcgac gacttcgtgg tgtccgtctg ctttcaggct cccgggagaa
1021    ggaccgaaac ctgcggcgta tcactcgact ggtgctggta gtggtggctg tgtttgtggg
1081    ctgctggacg cctgtgcagg tgtttgtcct ggttcaagga ctgggtgttc agccaggtag
1141    tgagactgca gttgccatcc tgcgcttctg cacagccctg ggctatgtca acagttgtct
1201    caatcccatt ctctatgctt tcctggatga gaacttcaag gcctgcttta gaaagttctg
1261    ctgtgcttca tccctgcacc gggagatgca ggtttctgat cgtgtgcgga gcattgccaq
1321    ggatgttggc cttggttgca agacttctga gacagtacca cggccagcat ga
```

Figure 14
SEQ ID NO:17

MESLFPAPYWEVLYGSHFQGNLSLLNETVPHHLLLNASHSAFLPLGLKVTIVGLYLAVCIGGLLGNCLVMH
TKMKTATNIYIFNLALADTLVLLTLPFQGTDILLGFWPFGNALCKTVIAIDYYNMFTSTFTLTAMSVDRYV
AICHPIRALDVRTSSKAQAVNVAIWALASVVGVPVAIMGSAQVEDEEIECLVEIPAPQDYWGPVFAICIFL
FSFIIPVLIISVCYSLMIRRLRGVRLLSGSREKDRNLRRITRLVLVVVAVFVGCWTPVQVFVLVQGLGVQP
GSETAVAILRFCTALGYVNSCLNPILYAFLDENFKACFRKFCCASSLHREMQVSDRVRSIAKDVGLGCKTS
ETVPRPA

Figure 15
SEQ ID NO:18

```
1    gctcatggag gcgttcatgt gcctgttagt gtagttgtgc tgtgttctaa ggcctcagtg
61   gacggtgtct agcactgtgg ttacttgttt ctgtgccctg ttccaggaac tgtactgagt
121  ggctttgcag ggtgacagca tggagtccct ctttcctgct ccatactggg aggtcttgta
181  tggcagccac tttcaaggga acctgtccct cctaaatgag accgtacccc accacctgct
241  cctcaatgct agtcacagcg ccttcctgcc ccttggactc aaggtcacca tcgtggggct
301  ctacttggct gtgtgcatcg gggggctcct ggggaactgc ctcgtcatgt atgtcatcct
361  cagctgggag ggcattgagg gggactggag acagcaggca caccaagatg aagacagcta
421  ccaacattta catatttaa
```

Figure 16
SEQ ID NO:19

```
   1    gctcatggag gcgttcatgt gcctgttagt gtagttgtgc tgtgttctaa ggcctcagtg
  61    gacggtgtct agcactgtgg ttacttgttt ctgtgccctg ttccaggaac tgtactgagt
 121    ggctttgcag ggtgacagca tggagtccct ctttcctgct ccatactggg aggtcttgta
 181    tggcagccac tttcaaggga acctgtccct cctaaatgag accgtacccc accacctgct
 241    cctcaatgct agtcacagcg ccttcctgcc ccttggactc aaggtcacca tcgtggggct
 301    ctacttggct gtgtgcatcg ggggctcct ggggaactgc ctcgtcatgt atgtcatcct
 361    caggcacacc aagatgaaga cagctaccaa catttacata tttaatctgg cactggctga
 421    taccctggtc ttgctaacac tgcccttcca gggcacagac atcctactgg gcttctggcc
 481    atttgggaat gcactctgca agactgtcat tgctatcgac tactacaaca tgtttaccag
 541    cacttttact ctgaccgcca tgagcgtaga ccgctatgtg gctatctgcc accctatccg
 601    tgcccttgat gttcggacat ccagcaaagc ccaggctgtt aatgtggcca tatgggccct
 661    ggcttcagtg gttggtgttc ctgttgccat catgggttca gcacaagtgg aagatgaaga
 721    gatcgagtgc ctggtggaga tccctgcccc tcaggactat ggggccctg tattcgccat
 781    ctgcatcttc ctttttcct tcatcatccc tgtgctgatc atctctgtct gctacagcct
 841    catgattcga cgacttcgtg gtgtccgtct gctttcaggc tcccgggaga aggaccgaaa
 901    cctgcggcgt atcactcgac tggtgctggt agtggtggct gtgtttgtgg gctgctggac
 961    gcctgtgcag gtgtttgtcc tggttcaagg actgggtgtt cagccaggta gtgagactgc
1021    agttgccatc ctgcgcttct gcacagccct gggctatgtc aacagttgtc tcaatccat
1081    tctctatgct ttcctggatg agaacttcaa ggcctgcttt agaaagttct gctgtgcttc
1141    atccctgcac cgggagatgc aggtttctga tcgtgtgcgg agcattgcca aggatgttgg
1201    ccttggttgc aagacttctg agacagtacc acggccagca tga
```

Figure 17
SEQ ID NO:20

```
1     gctcatggag gcgttcatgt gcctgttagt gtagttgtgc tgtgttctaa ggcctcagtg
61    gacggtgtct agcactgtgg ttacttgttt ctgtgccctg ttccaggaac tgtactgagt
121   ggctttgcag ggtgacagca tggagtccct ctttcctgct ccatactggg aggtcttgta
181   tggcagccac tttcaaggga acctgtccct cctaaatgag accgtacccc accacctgct
241   cctcaatgct agtcacagcg ccttcctgcc ccttggactc aaggtcacca tcgtggggct
301   ctacttggct gtgtgcatcg gggggctcct ggggaactgc ctcgtcatgc acaccaagat
361   gaagacagct accaacattt acatatttaa tctggcactg gctgataccc tggtcttgct
421   aacactgccc ttccagggca cagacatcct actgggcttc tggccatttg gaatgcact
481   ctgcaagact gtcattgcta tcgactacta caacatgttt accagcactt ttactctgac
541   cgccatgagc gtagaccgct atgtggctat ctgccaccct atccgtgccc ttgatgttcg
601   gacatccagc aaagcccagg ctgttaatgt ggccatatgg gccctggctt cagtggttgg
661   tgttcctgtt gccatcatgg gttcagcaca agtggaagat gaagagatcg agtgcctggt
721   ggagatccct gcccctcagg actattgggg ccctgtattc gccatctgca tcttcctttt
781   ttccttcatc atccctgtgc tgatcatctc tgtctgctac agcctcatga ttcgacgact
841   tcgtggtgtc cgtctgcttt caggctcccg ggagaaggac cgaaacctgc ggcgtatcac
901   tcgactggtg ctggtagtgg tggctgtgtt tgtgggctgc tggacgcctg tgcaggtgtt
961   tgtcctggtt caaggactgg gtgttcagcc aggtagtgag actgcagttg ccatcctgcg
1021  cttctgcaca gccctgggct atgtcaacag ttgtctcaat cccattctct atgctttcct
1081  ggatgagaac ttcaaggcct gctttagaaa gttctgctgt gcttcatccc tgcaccggga
1141  gatgcaggtt tctgatcgtg tgcggagcat tgccaaggat gttggccttg gttgcaagac
1201  ttctgagaca gtaccacggc cagcatga
```

Figure 18
SEQ ID NO:21

```
  1    gctcatggag gcgttcatgt gcctgttagt gtagttgtgc tgtgttctaa ggcctcagtg
 61    gacggtgtct agcactgtgg ttacttgttt ctgtgccctg ttccaggaac tgtactgagt
121    ggctttgcag ggtgacagca tggagtccct ctttcctgct ccatactggg aggtcttgta
181    tggcagccac tttcaaggga acctgtccct cctaaatgag accgtacccc accacctgct
241    cctcaatgct agtcacagcg ccttcctgcc ccttggactc aaggtcacca tcgtggggct
301    ctacttggct gtgtgcatcg ggggctcct ggggaactgc ctcgtcatgt atgtcatcct
361    cagagatcga gtgcctggtg gagatccctg cccctcagga ctattggggc cctgtattcg
421    ccatctgcat cttccttttt tccttcatca tccctgtgct gatcatctct gtctgctaca
481    gcctcatgat tcgacgactt cgtggtgtcc gtctgctttc aggctcccgg gagaaggacc
541    gaaacctgcg gcgtatcact cgactggtgc tggtagtggt ggctgtgttt gtgggctgct
601    ggacgcctgt gcaggtgttt gtcctggttc aaggactggg tgttcagcca ggtagtgaga
661    ctgcagttgc catcctgcgc ttctgcacag ccctgggcta tgtcaacagt tgtctcaatc
721    ccattctcta tgctttcctg gatgagaact tcaaggcctg ctttagaaag ttctgctgtg
781    cttcatccct gcaccgggag atgcaggttt ctgatcgtgt gcggagcatt gccaaggatg
841    ttggccttgg ttgcaagact tctgagacag taccacggcc agcatga
```

Figure 19
SEQ ID NO:22

```
   1  cctgctctgc acctgtcgtc gactgccagc cggctgaggg cggggggtctc cacggtggtc
  61  ccagctccca aggaggttgc agaagtaccg tacagagtgg atttgcaggg cagtggcatg
 121  gagcccctct tccccgcgcc gttctgggag gttatctacg gcagccacct tcagggcaac
 181  ctgtccctcc tgagcccaa  ccacagtctg ctgccccgc  atctgctgct caatgccagc
 241  cacggcgcct tcctgcccct cgggctcaag gtcaccatcg tggggctcta cctggccgtg
 301  tgtgtcggag ggctcctggg gaactgcctt gtcatgtacg tcatcctcag gcacaccaaa
 361  atgaagacag ccaccaatat ttacatcttt aacctggccc tggccgacac tctggtcctg
 421  ctgacgctgc ccttccaggg cacggacatc ctcctgggct tctggccgtt tgggaatgcg
 481  ctgtgcaaga cagtcattgc cattgactac tacaacatgt tcaccagcac cttcacccta
 541  actgccatga gtgtggatcg ctatgtagcc atctgccacc ccatccgtgc cctcgacgtc
 601  cgcacgtcca gcaaagccca ggctgtcaat gtggccatct gggccctggc ctctgttgtc
 661  ggtgttcccg ttgccatcat gggctcggca caggtcgagg atgaagagat cgagtgcctg
 721  gtggagatcc ctacccctca ggattactgg ggcccggtgt ttgccatctg catcttcctc
 781  ttctccttca tcgtccccgt gctcgtcatc tctgtctgct acagcctcat gatccggcgg
 841  ctccgtggag tccgcctgct ctcgggctcc cgagagaagg accggaacct gcggcgcatc
 901  actcggctgg tgctggtggt agtggctgtg ttcgtgggct gctggacgcc tgtccaggtc
 961  ttcgtgctgg cccaagggct ggggggttcag ccgagcagcg agactgccgt ggccattctg
1021  cgcttctgca cggccctggg ctacgtcaac agctgcctca ccccatcct ctacgccttc
1081  ctggatgaga acttcaaggc ctgcttccgc aagttctgct gtgcatctgc cctgcgccgg
1141  gacgtgcagg tgtctgaccg cgtgcgcagc attgccaagg acgtggccct ggcctgcaag
1201  acctctgaga cggtaccgcg gcccgcatga ctaggcgtgg acctgcccat ggtgcctgtc
1261  agcccgcaga gccatctac  gcccaacaca gagctcacac aggtcactgc tctctaggcg
1321  gacacaccct gggcctgag  catccagagc ctgggatggg cttttccctg tgggccaggg
1381  atgctcggtc ccagaggagg acctagtgac atcatgggac aggtcaaagc attagggcca
1441  cctccatggc cccagacaga ctaaagctgc cctcctggtg cagggccgag gggacacaag
1501  gacctacctg gaagcagctg acatgctggt ggacgccgt  tactggagcc cgtgcccctc
1561  cctccccgtg cttcatgtga ctcttggcct ctctgctgct gcgttggcag aaccctgggt
1621  gggcaggcac ccggaggagg agcagcagct gtgtcatcct gtgccccca  tgtgctgtgt
1681  gctgtttgca tggcagggct ccagctgcct tcagccctgt gacgtctcct cagggcagct
1741  ggacaggctt ggcacggccc gggaagtgca gcaggcagct tttctttggg gtgggacttg
1801  ccctgagctt ggagctgcca cctggaggac ttgcctgttc cgactccacc tgtgcagccg
1861  gggccacccc aggagaaagt gtccaggtgg gggctggcag tccctggctg cagacccga
1921  gctggccctc ggaccgcacc tctgaaggtt ttctgtgtgc tgcacggtgc aggcctcatc
1981  cctgactgca gcttgactct gggcccaacc cccatttccc ttcaggagac cagcgagagg
2041  ccctggccat ccctccagcg gtgcaatgaa ctatatgctg tggaccgtca acccagccct
2101  gcttctcagt gtggggcagg tgtctcagga cgaaggcgcc gcgtgaccac atgggcagct
2161  ctgttcacaa agtggaggcc tcgtttcct  ggtcttgact gctctgtttg ggtgggagaa
2221  gattctctgg gggtcccac  atcctcccaa ggctcccctc acagcctctc ctttgcttga
2281  agccagaggt cagtggccgt gctgtgttgc ggggaagctg tgtggaagga gaagctggtg
2341  gccacagcag agtcctgctc tggggacgcc tgcttcattt acaagcctca agatggctct
2401  gtgtagggcc tgagcttgct gcccaacggg aggatggctt cacagcagag ccagcatgag
2461  gggtggggcc tggcagggct tgcttgagcc aaactgcaaa ggctgtggtg gctgtgagga
2521  cactgcgggg gttg
```

Figure 20
SEQ ID NO:23

MESLFPAPYWEVLYGSHFQGNLSLLNETVPHHLLLNASHSAFLPLGLKVTIVGLYLAVCIGGLLGN
CLVMYVILRDRVPGGDPCPSGLLGPCIRHLHLPFFLHHPCADHLCLLQPHDSTTSWCPSAFRLPGE
GPKPAAYHSTGAGSGGCVCGLLDACAGVCPGSRTGCSAR

SEQUENCE LISTING

```
<160> NUMBER OF SEQ ID NOS: 36

<210> SEQ ID NO 1
<211> LENGTH: 23
<212> TYPE: DNA
<213> ORGANISM: Artificial Sequence
<220> FEATURE:
<223> OTHER INFORMATION: Synthetic

<400> SEQUENCE: 1
gcagcagccg gtgcggcagc cag                                          23

<210> SEQ ID NO 2
<211> LENGTH: 21
<212> TYPE: DNA
<213> ORGANISM: Artificial Sequence
<220> FEATURE:
<223> OTHER INFORMATION: Synthetic

<400> SEQUENCE: 2
```

-continued tagacaccgt ccactgaggc c                                              21

<210> SEQ ID NO 3
<211> LENGTH: 26
<212> TYPE: DNA
<213> ORGANISM: Artificial Sequence
<220> FEATURE:
<223> OTHER INFORMATION: Synthetic

<400> SEQUENCE: 3
gtttctgtgc cctgttccag gaactg                                         26

<210> SEQ ID NO 4
<211> LENGTH: 25
<212> TYPE: DNA
<213> ORGANISM: Artificial Sequence
<220> FEATURE:
<223> OTHER INFORMATION: Synthetic

<400> SEQUENCE: 4
cctgcccctt ggactcaagg tcacc                                          25

<210> SEQ ID NO 5
<211> LENGTH: 24
<212> TYPE: DNA
<213> ORGANISM: Artificial Sequence
<220> FEATURE:
<223> OTHER INFORMATION: Synthetic

<400> SEQUENCE: 5
ggtccacgcc tagtcatgct ggcc                                           24

<210> SEQ ID NO 6
<211> LENGTH: 25
<212> TYPE: DNA
<213> ORGANISM: Artificial Sequence
<220> FEATURE:
<223> OTHER INFORMATION: Synthetic

<400> SEQUENCE: 6
gctcagtcca ctgtgctcct gcctg                                          25

<210> SEQ ID NO 7
<211> LENGTH: 26
<212> TYPE: DNA
<213> ORGANISM: Artificial Sequence
<220> FEATURE:
<223> OTHER INFORMATION: Synthetic

<400> SEQUENCE: 7
ggtgctaaaa ggtcttcctc taggac                                         26

<210> SEQ ID NO 8
<211> LENGTH: 20
<212> TYPE: DNA
<213> ORGANISM: Artificial Sequence
<220> FEATURE:
<223> OTHER INFORMATION: Synthetic

<400> SEQUENCE: 8
cagtgttagc aagaccaggg                                                20

<210> SEQ ID NO 9
<211> LENGTH: 8372
<212> TYPE: DNA
<213> ORGANISM: Rattus norvegicus

<400> SEQUENCE: 9

```
tgtgtgcccg tctgccaatt taagcatgtt accagcattc ccatcgtttc caaatgctga      60
gcccttgaga ctcggagacg cacgtgaaag actactttag ggatatagag actctgtacg     120
aggtgcagga actctctggg ggtttgtgtg ccagcttttg ccggggtgg catggggatg      180
aaaaaggaag tgatggaagg gcagggagag agagagagag agagagagag agagagagag     240
agagagagag agagagagca acagagagtg catacttatg tgctatatat ctagggcct      300
ttctctgttc ttgcctgttc ccacactagt tcacatcttg tttgtatctt tctctttgtg     360
cctgaatgca ccttgtgggt tgtatatgtg atccttgtgt gcatctctga gcacatatcc     420
cttgtgtctc tgtatctcta aactgtgcct gtctgggtac ctctttgtat gttctgttta     480
tttgcaggaa tgtgtcctca tgtgtctcct tgagtgtcca tgtgtctccg agaacggaga     540
gacaagtcct tggagacagc ttgggatgct gagtcctggg gtgtctgtct gctctggcct     600
tttctggttg acaggtatc ctagcaacac ttctgtgagt tgcctagcaa ccaggtcccc      660
atccttagag aaagagcagg gtctggctgt atgtgggagg tctggctctc attcagtcca     720
gacaggaaaa acaaacctat gatttgatga tgactagaga ctcagcatag ggtccctagc     780
ctacatgacc ttaacttatg gttttttcct cagtggactg tgctccccca ccccacccc      840
cccgtgctgg caaagaagga ggtccctagg agcttagtat ctctgtgttt tctaagatct     900
aattctggga tttggctgtg gtgtagcttc aagtgaccag caaacctggc ttccccttat     960
ccctgccatg ttgacaggca gctccagact tcagaggcgt gatgctttca tttgtgtgag    1020
gataatatgg gtggcagtgg ccatgtgtag tggggttcc tgggttcagt tttgtcttga    1080
gcttagtgca cattaggtat aaacagcaca tagtagactc agggcagtgc tgggtccaca    1140
gtccagacaa tctcttgttt attcgcaaga aggcctttac atggagaatt agttgggtca    1200
ggatattgct atcactgtgg tactctaccc tattggacac cggctgaggg cagttctggg    1260
taggaaagct agcaaaatct ggtctgtgct cagtggtggt agcacatgcc tttaatccta    1320
gcattcagga agcagaggca gatgtgtctc taagttctag gacagccaag gctacacaga    1380
caaatcctgt ctctaacctg ttaacttccc caaacaaaac aaaacaaaac agagcaaagc    1440
aaagcaaagc aaaacaaaac aaaacaacat tttcgagtgt tggagcctca cgtctacttc    1500
tgggtgagca tttctctgta tacatcttga atgtgttctt gtgtctaagg ctgtgcgtgt    1560
atgtgtgtct gaattcctgt tcatgtctct atttttgtgt tcatggatgt ccccattgtg    1620
tgtcctaggg cctgagtgtg tttgtgttgg gtgagcccat cacattatat gtttgttaat    1680
cttttggctc ctacttggtg tggagcctag gggttctggt ctggtaatct tccttttttt    1740
tttttttttt tggctttctt ctccaacctg cacagcccct ccttctctca gccgcagcct    1800
tctgcccctc cccttctgg ctgccgcacc ggctgctgcg tctagtcaat atcttatctt     1860
ccgagcagga gctaggagcc attcccagcc gcagcagacc ccaatctaga gtgagagtca    1920
ttgctcagtc cactgtgctc ctgcctgccc gcctttctgc taagcattgg ggtctatttt    1980
ggcccagctt ctgaagaggc tgtgtgtgcc gttggaggta agaggggctc ctgctgcctc    2040
tgacagagct gggggtgggg gagccctggg aggtagctat gtgaagtgcc tgagccttag    2100
gcatttctgg ataaattcca tgccttttgt gccccagtgt accttaggat ggtttaggca    2160
ttttttgtgt ttggctggct gtgagccct gggtcttggt gggtggacat gtgtgcttgt     2220
gtagctacgt tgcttctgtg cgggtctata accctaatgt gaggtaacct tgtaggtaaa    2280
```

```
tgtgctccca tgcctctgtg tgtgtcacca tgtgcccacg ggcatgtctg cctttgtctg    2340
tgtccgtgtg tctgtgtgtg tgcctagtgt ttgtgcatgc tcatggaggc gttcatgtgc    2400
ctgttagtgt agttgtgctg tgttctaagg cctcagtgga cggtgtctag cactgtggtt    2460
acttgtttct gtgccctgtt ccaggaactg tactgagtgg ctttgcaggg tgacagcatg    2520
gagtccctct ttcctgctcc atactgggag gtcttgtatg gcagccactt tcaagggaac    2580
ctgtccctcc taaatgagac cgtacCccac cacctgctcc tcaatgctag tcacagcgcc    2640
ttcctgcccc ttggactcaa ggtcaccatc gtgggctctc acttggctgt gtgcatcggg    2700
gggctcctgg ggaactgcct cgtcatgtat gtcatcctca ggtaggctgg gccccatcag    2760
tctgtgaagg gggaacctga ggcaggaggc tgttctgggt gaatctgaac aagtatggat    2820
tttctgcttg ctccatcaaa tttctttcct ctctgttcaa ggggcatgac cacccttgaa    2880
gttcaactcc tgttctgtcc ccatctgtct cagactaggt ggaggcttgg agctgcagat    2940
aaattcatgc catgatgtct gtgtgaataa cctcatgggt acacaggatc ctaggatttc    3000
tcaaacagag gaagagggc tggtgctggg cctgaagctc ttattcattg acttttggga    3060
tctctattca tggtggatgt ctttagctga gcccatgctc tattggtgct cagaaatatg    3120
aaaatttgga ggactagaaa gaaaggcagc agtactgggc aactgagtca gagtcaacag    3180 tgagggata ctggagggag cagtatgagg tgcagttctg tggacacaaa agctggacaa    3240
ggagtatgca attggtaaaa tgtgtcacgg caatgatggt ctctgttttt ttccagctgg    3300
gagggcattg aggggactg gagacagcag gtgaggactt gaatgccaga atggggacat    3360
tgggaagaca tgggaggtcc ttgaatggtg aataactaga gcaaggttct tcactgatat    3420
atttcctctt tcaaaaagat gactctgaag aaagcagtca tggtcccctt gatggtatca    3480
tggtaggtgt ggtggtggtg gagaaagggc agtgcaggtt ctatattctg cctcatcacg    3540
atcctcttag tattcctgag caactgtttt ctccattcgt tagatgggaa atatggatta    3600
cataaccata tataggtgca tgtgcataca cgtgtatata gtataatatt gatatgtgat    3660
tggacagtgt agtaggaaaa gccttccaag tactgacttt cagcagagga tccttgtggg    3720
aaactattct atgatctaag tgttagagga tattcatctt tggcaagaag tgcagcaacc    3780
tgggacagtt tgtgagcctt gccttcccctt cttgtcctca gcatttctct cccatattta    3840
ctgcatcagg gcagacaagg agcaccatct ttccagtag catcctcaga gagctagtct    3900
caggaactgc tgtggccaca ctggctctgg aggcaaaaca cggcgtgttt gagttggcat    3960
acgccaggag tcagaaaaac ctgctctgag ccccattttg cccttcgca gttccaagcc    4020 ttataaaagc tacttacgtc ctccgagcct cagcttcctt ctctgcagcc tagggatcta    4080
atagcatttt ttcttttggg gtaaacctca aatgagataa aatctacgtg aagagcttgg    4140
ctcagatatc taccattatc gttgttattg ttgtttattg tagttaaggt ctctaggatt    4200
aatgtctaag aaacagaact taatcccaga ttccctgata gcaactaaac tatcatggac    4260
tactgttacc tctagttcta tcactaccat accaccataa ccactctaac caccaccacc    4320
accaccatca ctataatcac ccttccctac cgctatcata acattaatt cattccacta    4380 atatttatca cttataatgt ccctagcatg gttcccggtg cttggataca tcaaacctaa    4440
ctagcacatc tcttgtttc tttattagaa ttaaaaaata aattatgttt atttatgtgt    4500
ctgtgtatgt ctgtctggat gtgtaggtca gaggagaaag ttgggtttct ccttttacca    4560
tgtaagtttc tccttctacc acatgcgtcc tggagataga actcaggttg tcagaattgg    4620
tagtaagtgc ccttaccggc tgagccattt ggctggccca gcattgtctg ttttcattgc    4680
```

-continued

```
tagacaatac tgtgcagttg aagacacag atctttgatg aactttacag gcagtgccct    4740
gaaaagcctc tgagagaagt cttaagagag actgaggaga gaagacagca tctctctctc   4800
ttgattcatt ccacaaactc acattcaggt tagatatgca ctcaggtact cctccatgcc   4860
cccaactttt ccagggtagt cttgtcattg atttggaacc tttctgtaga tgtcatagtc   4920
acatggggaa gcttgttaaa gtcccaggct cagtggactt tgggtgtggt gcaggatctg   4980
ccatttaata agcttccttg gagactctgg ggttgagaga ttcaaagacc ataaccctct   5040
tggtggtccc ttagctgcca agtctacgca aaatggccaa atggagcctt tcttctcctt   5100
gtcctctaca ggcacaccaa gatgaagaca gctaccaaca tttacatatt taatctggca   5160
ctggctgata ccctggtctt gctaacactg cccttccagg gcacagacat cctactgggc   5220
ttctggccat ttgggaatgc actctgcaag actgtcattg ctatcgacta ctacaacatg   5280
tttaccagca ctttttactct gaccgccatg agcgtagacc gctatgtggc tatctgccac   5340
cctatccgtg cccttgatgt tcggacatcc agcaaagccc aggctgttaa tgtggccata   5400
tgggccctgg cttcagtggt tggtgttcct gttgccatca tgggttcagc acaagtggaa   5460
gatgaaggtc agtgggtggt cctcctccct gactcattag tttcccatgg ttcttgctgg   5520
tccctctgac cccatttctc tcctgcagag atcgagtgcc tggtggagat ccctgcccct   5580
caggactatt ggggccctgt attcgccatc tgcatcttcc ttttttcctt catcatccct   5640
gtgctgatca tctctgtctg ctacagcctc atgattcgac gacttcgtgg tgtccgtctg   5700
cttttcaggct cccgggagaa ggaccgaaac ctgcggcgta tcactcgact ggtgctggta   5760
gtggtggctg tgtttgtggg ctgctggacg cctgtgcagg tgtttgtcct ggttcaagga   5820
ctgggtgttc agccaggtag tgagactgca gttgccatcc tgcgcttctg cacagccctg   5880
ggctatgtca acagttgtct caatcccatt ctctatgctt tcctggatga aacttcaag    5940
gcctgcttta gaaagttctg ctgtgcttca tccctgcacc gggagatgca ggtttctgat   6000
cgtgtgcgga gcattgccaa ggatgttggc cttggttgca agacttctga gacagtacca   6060
cggccagcat gactaggcgt ggacctgccc atggtgcctg tcagcccaca gagcccatct   6120
acacccaaca cggagctcac acaggtcact gctctctagg ttgaccctga accttgagca   6180
tctggagcct tgaatggctt tctttttgga tcaggatgct cagtcctaga ggaagacctt   6240
ttagcaccat gggacaggtc aaagcatcaa ggtggtctcc atggcctctg tcagattaag   6300
ttccctccct ggtataggac cagagaggac caaaggaact gaatagaaac atccacaaca   6360
cagtggacat gcctggtgag cccatgtagg tattcatgct tcacttgact cttctctggc   6420
ttctcccctgc tgccctggct ctagctgggc tcaacctgag gtattgtagt ggtcatgtag   6480
tcactcttgt gactacatgt tgtgtgctgt tgctctcggc ctttcagtat ttccacagga   6540
ctgctgaaca tacctggtat tgcagtgggg agcattaatt ttcttttaaa gtgagactgg   6600
cccttaagct tggcgttgcc ttggagcgtc ttctacttct gacttcactg atgcagtcag   6660
attacccgag ggtgagcatc agtggttctt tggatggctg ttttctgaag attcttccca   6720
tccagtacat ggagtctatg aagggagtca caattcatct ggtactgcca ctacctgctc   6780
tataatcctg ggctatcttc ttggcaagat gacagtgggg gagacaagac acagagcttc   6840
cctaaggctc tttccctcca aaaccactgt gaactcttat cctacagact gttcggcaag   6900
cactgcttct aggtgtgtgg gaggtaatca ggagaaagct tgtggcctc tgtaggctgc    6960
tcacaacatg gaggcaccac atgctggtct tgcctgctta gtacaggcag gacagagcag   7020
```

| | |
|---|---|
| aatatgctct ctctcgattc tctacaaact ccctcagttc tccagcagag tctcttttac | 7080 |
| ttgctatcag aggtcaggag ttgtactgct agaagcatac ttgtagcttg ggaagagtgg | 7140 |
| cagtcaggat gtgttctact ctatatccac agtgaccacc tgcttcatat atagggttag | 7200 |
| gacatatctg agtaaggcct gagtgtgctg ccaaattgga ggttggtatg agagctgatg | 7260 |
| cctaaagtgg ctcatttgca aggactatta tggtttggaa tagcaatggg cactggtcgg | 7320 |
| cgaagaagag tctataacctt cgagatctat ttgatggttc acagaagagg ttttgtcaaa | 7380 |
| cgcccttcta tgggtcagat atcaaaatac cagcaacgtt ggatagattc tgaccttta | 7440 |
| ctgagacctc ggtcagatgg tttcatgtca tgcagagaac ctaggctggt tcctgtgtca | 7500 |
| gagagacctg ggcttctggg gaggccaggg ttcttccttt gacacttgtg cgggacgcgt | 7560 |
| tagctctaga gttttcttgc taatgctaag aaactttgtg aatttgtata tctttatgta | 7620 |
| tttaagcatg caacaagcgt catttccatg catgtagcta gccctgaacc tgcctctggg | 7680 |
| gtaatgaagg agtgctcata acaaacactt atccagtgac cagtactgtc catagcctaa | 7740 |
| gtgtttctga ctccagctac ataagagtaa cttcctgggt attgatatgc actgggatga | 7800 |
| ggcacagaac caggttcatg ggtttaaac ctgttctgcc cttgcaaggg actttaagga | 7860 |
| acttcttgat tgatgggagg aaaactagtt cctgggttgc agaggctgct gcctttcctt | 7920 |
| ctcccaagac aatgactatc ttttctcccc acactcagga acagtgggta gatgcctttc | 7980 |
| ttcacagttt ttctttgtag actcttgctg cttgagcaaa tctaaaagga gttgtggtga | 8040 |
| tcagagcaga ggacccttct ctggtggcag agcaaccta tgctatagag atctacccc | 8100 |
| tggctcttgt ctgtgtaggc ccaatctggc tcaattgacc ctctggcaga tggcccttat | 8160 |
| caggggggct ttgaagaggg tcttacttgc caaagcgctt gctttcagta cagagctggt | 8220 |
| gagccaaagc ttggttttat acaagtttta atgacattgt ccatttgttt tttgtttttt | 8280 |
| agtctagcag tttataatca aaggtatga atttctaata ggcttaaaag atgcagccca | 8340 |
| tgcaggcatg gtggattgga ttctatgaga tt | 8372 |

<210> SEQ ID NO 10
<211> LENGTH: 1566
<212> TYPE: DNA
<213> ORGANISM: Rattus norvegicus

<400> SEQUENCE: 10

| | |
|---|---|
| ctgcacagcc cctccttctc tcagccgcag ccttctgccc ctcccccttc tggctgccgc | 60 |
| accggctgct gcgtctagtc aatatcttat cttccgagca ggagctagga gccattccca | 120 |
| gccgcagcag accccaatct agagtgagag tcattgctca gtccactgtg ctcctgcctg | 180 |
| cccgcctttc tgctaagcat tgggtctat tttggcccag cttctgaaga ggctgtgtgt | 240 |
| gccgttggag gaactgtact gagtggcttt gcagggtgac agcatggagt ccctctttcc | 300 |
| tgctccatac tgggaggtct tgtatggcag ccactttcaa gggaacctgt ccctcctaaa | 360 |
| tgagaccgta ccccaccacc tgctcctcaa tgctagtcac agcgccttcc tgccccttgg | 420 |
| actcaaggtc accatcgtgg ggctctactt ggctgtgtgc atcgggggc tcctggggaa | 480 |
| ctgcctcgtc atgtatgtca tcctcagctg ggagggcatt gagggggact ggagacagca | 540 |
| gacaatactg tgcagttgga agacacagat ctttgatgaa ctttacaggc agtgccctga | 600 |
| aaagcctctg agagaagtct taagagagac tgaggagaga agacagcatc tctctctctt | 660 |
| gattcattcc acaaactcac attcaggcac accaagatga agacagctac caacatttac | 720 |
| atatttaatc tggcactggc tgataccctg gtcttgctaa cactgccctt ccagggcaca | 780 |

```
gacatcctac tgggcttctg gccatttggg aatgcactct gcaagactgt cattgctatc      840
gactactaca acatgtttac cagcactttt actctgaccg ccatgagcgt agaccgctat      900
gtggctatct gccaccctat ccgtgccctt gatgttcgga catccagcaa agcccaggct      960
gttaatgtgg ccatatgggc cctggcttca gtggttggtg ttcctgttgc catcatgggt     1020
tcagcacaag tggaagatga agagatcgag tgcctggtgg agatccctgc ccctcaggac     1080
tattggggcc ctgtattcgc catctgcatc ttccttttt ccttcatcat ccctgtgctg     1140
atcatctctg tctgctacag cctcatgatt cgacgacttc gtggtgtccg tctgctttca     1200
ggctcccggg agaaggaccg aaacctgcgg cgtatcactc gactggtgct ggtagtggtg     1260
gctgtgtttg tgggctgctg gacgcctgtg caggtgtttg tcctggttca aggactgggt     1320
gttcagccag gtagtgagac tgcagttgcc atcctgcgct ctgcacagc cctgggctat     1380 gtcaacagtt gtctcaatcc cattctctat gctttcctgg atgagaactt caaggcctgc     1440
tttagaaagt tctgctgtgc ttcatccctg caccgggaga tgcaggtttc tgatcgtgtg     1500
cggagcattg ccaaggatgt tggccttggt tgcaagactt ctgagacagt accacggcca     1560
gcatga                                                                1566
```

<210> SEQ ID NO 11
<211> LENGTH: 138
<212> TYPE: PRT
<213> ORGANISM: Rattus norvegicus

<400> SEQUENCE: 11

```
Met Glu Ser Leu Phe Pro Ala Pro Tyr Trp Glu Val Leu Tyr Gly Ser
1               5                  10                  15

His Phe Gln Gly Asn Leu Ser Leu Leu Asn Glu Thr Val Pro His His
                20                  25                  30

Leu Leu Leu Asn Ala Ser His Ser Ala Phe Leu Pro Leu Gly Leu Lys
            35                  40                  45

Val Thr Ile Val Gly Leu Tyr Leu Ala Val Cys Ile Gly Gly Leu Leu
        50                  55                  60

Gly Asn Cys Leu Val Met Tyr Val Ile Leu Ser Trp Glu Gly Ile Glu
65                  70                  75                  80

Gly Asp Trp Arg Gln Gln Thr Ile Leu Cys Ser Trp Lys Thr Gln Ile
                85                  90                  95

Phe Asp Glu Leu Tyr Arg Gln Cys Pro Glu Lys Pro Leu Arg Glu Val
                100                 105                 110

Leu Arg Glu Thr Glu Glu Arg Arg Gln His Leu Ser Leu Leu Ile His
        115                 120                 125

Ser Thr Asn Ser His Ser Gly Thr Pro Arg
    130                 135
```

<210> SEQ ID NO 12
<211> LENGTH: 1421
<212> TYPE: DNA
<213> ORGANISM: Rattus norvegicus

<400> SEQUENCE: 12

```
ctgcacagcc cctccttctc tcagccgcag ccttctgccc ctcccccttc tggctgccgc       60
accggctgct gcgtctagtc aatatcttat cttccgagca ggagctagga gccattccca      120
gccgcagcag accccaatct agagtgagag tcattgctca gtccactgtg ctcctgcctg      180
cccgcctttc tgctaagcat tggggtctat tttggcccag cttctgaaga ggctgtgtgt      240
```

-continued

```
gccgttggag gaactgtact gagtggcttt gcagggtgac agcatggagt ccctctttcc      300
tgctccatac tgggaggtct tgtatggcag ccactttcaa gggaacctgt ccctcctaaa      360
tgagaccgta ccccaccacc tgctcctcaa tgctagtcac agcgccttcc tgccccttgg      420
actcaaggtc accatcgtgg ggctctactt ggctgtgtgc atcggggggc tcctggggaa      480
ctgcctcgtc atgtatgtca tcctcagctg ggagggcatt gaggggggact ggagacagca      540 ggcacaccaa gatgaagaca gctaccaaca tttacatatt taatctggca ctggctgata      600
ccctggtctt gctaacactg cccttccagg gcacagacat cctactgggc ttctggccat      660
ttgggaatgc actctgcaag actgtcattg ctatcgacta ctacaacatg tttaccagca      720
cttttactct gaccgccatg agcgtagacc gctatgtggc tatctgccac cctatccgtg      780
cccttgatgt tcggacatcc agcaaagccc aggctgttaa tgtggccata tgggccctgg      840
cttcagtggt tggtgttcct gttgccatca tgggttcagc acaagtggaa gatgaagaga      900
tcgagtgcct ggtggagatc cctgcccctc aggactattg gggccctgta ttcgccatct      960
gcatcttcct ttttccttc atcatccctg tgctgatcat ctctgtctgc tacagcctca      1020
tgattcgacg acttcgtggt gtccgtctgc tttcaggctc ccgggagaag gaccgaaacc      1080
tgcggcgtat cactcgactg gtgctggtag tggtggctgt gtttgtgggc tgctggacgc      1140
ctgtgcaggt gtttgtcctg gttcaaggac tgggtgttca gccaggtagt gagactgcag      1200
ttgccatcct gcgcttctgc acagccctgg gctatgtcaa cagttgtctc aatcccattc      1260 tctatgctttt cctggatgag aacttcaagg cctgctttag aaagttctgc tgtgcttcat      1320
ccctgcaccg ggagatgcag gtttctgatc gtgtgcggag cattgccaag gatgttggcc      1380
ttggttgcaa gacttctgag acagtaccac ggccagcatg a                         1421
```

<210> SEQ ID NO 13
<211> LENGTH: 99
<212> TYPE: PRT
<213> ORGANISM: Rattus norvegicus

<400> SEQUENCE: 13

```
Met Glu Ser Leu Phe Pro Ala Pro Tyr Trp Glu Val Leu Tyr Gly Ser
1               5                   10                  15

His Phe Gln Gly Asn Leu Ser Leu Leu Asn Glu Thr Val Pro His His
            20                  25                  30

Leu Leu Leu Asn Ala Ser His Ser Ala Phe Leu Pro Leu Gly Leu Lys
        35                  40                  45

Val Thr Ile Val Gly Leu Tyr Leu Ala Val Cys Ile Gly Gly Leu Leu
    50                  55                  60

Gly Asn Cys Leu Val Met Tyr Val Ile Leu Ser Trp Glu Gly Ile Glu
65                  70                  75                  80

Gly Asp Trp Arg Gln Gln Ala His Gln Asp Glu Asp Ser Tyr Gln His
                85                  90                  95

Leu His Ile
```

<210> SEQ ID NO 14
<211> LENGTH: 1387
<212> TYPE: DNA
<213> ORGANISM: Rattus norvegicus

<400> SEQUENCE: 14

```
ctgcacagcc cctccttctc tcagccgcag ccttctgccc ctccccttc tggctgccgc      60
```

-continued

```
accggctgct gcgtctagtc aatatcttat cttccgagca ggagctagga gccattccca      120
gccgcagcag accccaatct agagtgagag tcattgctca gtccactgtg ctcctgcctg      180
cccgcctttc tgctaagcat tgggtctat tttggcccag cttctgaaga ggctgtgtgt       240
gccgttggag gaactgtact gagtggcttt gcagggtgac agcatggagt ccctctttcc      300
tgctccatac tgggaggtct tgtatggcag ccactttcaa gggaacctgt ccctcctaaa      360
tgagaccgta ccccaccacc tgctcctcaa tgctagtcac agcgccttcc tgccccttgg      420
actcaaggtc accatcgtgg ggctctactt ggctgtgtgc atcggggggc tcctggggaa      480
ctgcctcgtc atgtatgtca tcctcaggca caccaagatg aagacagcta ccaacattta      540
catatttaat ctggcactgg ctgatacccet ggtcttgcta acactgccct tccagggcac      600
agacatccta ctgggcttct ggccatttgg gaatgcactc tgcaagactg tcattgctat      660
cgactactac aacatgttta ccagcacttt tactctgacc gccatgagcg tagaccgcta      720
tgtggctatc tgccacccta tccgtgccct tgatgttcgg acatccagca aagcccaggc      780
tgttaatgtg gccatatggg gcctggcttc agtggttggt gttcctgttg ccatcatggg      840
ttcagcacaa gtggaagatg aagagatcga gtgcctggtg gagatccctg cccctcagga      900
ctattggggc cctgtattcg ccatctgcat cttcctttt tccttcatca tccctgtgct       960
gatcatctct gtctgctaca gcctcatgat tcgacgactt cgtggtgtcc gtctgctttc     1020
aggctcccgg gagaaggacc gaaacctgcg gcgtatcact cgactggtgc tggtagtggt     1080
ggctgtgttt gtgggctgct ggacgcctgt gcaggtgttt gtcctggttc aaggactggg     1140
tgttcagcca ggtagtgaga ctgcagttgc catcctgcgc ttctgcacag ccctgggcta     1200
tgtcaacagt gtgtctcaatc ccattctcta tgctttcctg gatgagaact tcaaggcctg    1260
ctttagaaag ttctgctgtg cttcatccct gcaccgggag atgcaggttt ctgatcgtgt     1320
gcggagcatt gccaaggatg ttggccttgg ttgcaagact tctgagacag taccacggcc     1380
agcatga                                                               1387
```

<210> SEQ ID NO 15
<211> LENGTH: 367
<212> TYPE: PRT
<213> ORGANISM: Rattus norvegicus

<400> SEQUENCE: 15

```
Met Glu Ser Leu Phe Pro Ala Pro Tyr Trp Glu Val Leu Tyr Gly Ser
1               5                   10                  15

His Phe Gln Gly Asn Leu Ser Leu Leu Asn Glu Thr Val Pro His His
                20                  25                  30

Leu Leu Leu Asn Ala Ser His Ser Ala Phe Leu Pro Leu Gly Leu Lys
            35                  40                  45

Val Thr Ile Val Gly Leu Tyr Leu Ala Val Cys Ile Gly Gly Leu Leu
        50                  55                  60

Gly Asn Cys Leu Val Met Tyr Val Ile Leu Arg His Thr Lys Met Lys
65                  70                  75                  80

Thr Ala Thr Asn Ile Tyr Ile Phe Asn Leu Ala Leu Ala Asp Thr Leu
                85                  90                  95

Val Leu Leu Thr Leu Pro Phe Gln Gly Thr Asp Ile Leu Leu Gly Phe
            100                 105                 110

Trp Pro Phe Gly Asn Ala Leu Cys Lys Thr Val Ile Ala Ile Asp Tyr
        115                 120                 125

Tyr Asn Met Phe Thr Ser Thr Phe Thr Leu Thr Ala Met Ser Val Asp
```

```
                130             135             140
Arg Tyr Val Ala Ile Cys His Pro Ile Arg Ala Leu Asp Val Arg Thr
145                 150                 155                 160

Ser Ser Lys Ala Gln Ala Val Asn Val Ala Ile Trp Ala Leu Ala Ser
                165                 170                 175

Val Val Gly Val Pro Val Ala Ile Met Gly Ser Ala Gln Val Glu Asp
                180                 185                 190

Glu Glu Ile Glu Cys Leu Val Glu Ile Pro Ala Pro Gln Asp Tyr Trp
            195                 200                 205

Gly Pro Val Phe Ala Ile Cys Ile Phe Leu Phe Ser Phe Ile Ile Pro
210                 215                 220

Val Leu Ile Ile Ser Val Cys Tyr Ser Leu Met Ile Arg Arg Leu Arg
225                 230                 235                 240

Gly Val Arg Leu Leu Ser Gly Ser Arg Glu Lys Asp Arg Asn Leu Arg
                245                 250                 255

Arg Ile Thr Arg Leu Val Leu Val Val Ala Val Phe Val Gly Cys
                260                 265                 270

Trp Thr Pro Val Gln Val Phe Val Leu Val Gln Gly Leu Gly Val Gln
                275                 280                 285

Pro Gly Ser Glu Thr Ala Val Ala Ile Leu Arg Phe Cys Thr Ala Leu
            290                 295                 300

Gly Tyr Val Asn Ser Cys Leu Asn Pro Ile Leu Tyr Ala Phe Leu Asp
305                 310                 315                 320

Glu Asn Phe Lys Ala Cys Phe Arg Lys Phe Cys Cys Ala Ser Ser Leu
                325                 330                 335

His Arg Glu Met Gln Val Ser Asp Arg Val Arg Ser Ile Ala Lys Asp
                340                 345                 350

Val Gly Leu Gly Cys Lys Thr Ser Glu Thr Val Pro Arg Pro Ala
                355                 360                 365

<210> SEQ ID NO 16
<211> LENGTH: 1372
<212> TYPE: DNA
<213> ORGANISM: Rattus norvegicus

<400> SEQUENCE: 16
ctgcacagcc cctccttctc tcagccgcag ccttctgccc ctccccttc tggctgccgc      60 accggctgct gcgtctagtc aatatcttat cttccgagca ggagctagga gccattccca    120
gccgcagcag accccaatct agagtgagag tcattgctca gtccactgtg ctcctgcctg    180
cccgcctttc tgctaagcat tgggtctat tttggcccag cttctgaaga ggctgtgtgt     240
gccgttggag gaactgtact gagtggcttt gcagggtgac agcatggagt ccctctttcc    300
tgctccatac tgggaggtct tgtatggcag ccactttcaa gggaacctgt ccctcctaaa    360
tgagaccgta ccccaccacc tgctcctcaa tgctagtcac agcgccttcc tgccccttgg    420
actcaaggtc accatcgtgg ggctctactt ggctgtgtgc atcgggggc tcctggggaa     480 ctgcctcgtc atgcacacca agatgaagac agctaccaac atttacatat taatctggc     540 actggctgat accctggtct tgctaacact gcccttccag ggcacagaca tcctactggg    600
cttctggcca tttgggaatg cactctgcaa gactgtcatt gctatcgact actacaacat    660
gtttaccagc actttttactc tgaccgccat gagcgtagac cgctatgtgg ctatctgcca    720
ccctatccgt gcccttgatg ttcggacatc agcaaagcc caggctgtta atgtggccat      780
atgggccctg gcttcagtgg ttggtgttcc tgttgccatc atgggttcag cacaagtgga    840
```

```
agatgaagag atcgagtgcc tggtggagat ccctgcccct caggactatt ggggccctgt      900
attcgccatc tgcatcttcc ttttttcctt catcatccct gtgctgatca tctctgtctg      960
ctacagcctc atgattcgac gacttcgtgg tgtccgtctg ctttcaggct cccgggagaa     1020
ggaccgaaac ctgcggcgta tcactcgact ggtgctggta gtggtggctg tgtttgtggg     1080
ctgctggacg cctgtgcagg tgtttgtcct ggttcaagga ctgggtgttc agccaggtag     1140
tgagactgca gttgccatcc tgcgcttctg cacagccctg gctatgtca acagttgtct     1200
caatcccatt ctctatgctt cctggatga aacttcaag gcctgcttta gaaagttctg     1260
ctgtgcttca tccctgcacc gggagatgca ggtttctgat cgtgtgcgga gcattgccaa     1320
ggatgttggc cttggttgca agacttctga gacagtacca cggccagcat ga            1372
```

<210> SEQ ID NO 17
<211> LENGTH: 362
<212> TYPE: PRT
<213> ORGANISM: Rattus norvegicus

<400> SEQUENCE: 17

```
Met Glu Ser Leu Phe Pro Ala Pro Tyr Trp Glu Val Leu Tyr Gly Ser
1               5                   10                  15

His Phe Gln Gly Asn Leu Ser Leu Leu Asn Glu Thr Val Pro His His
            20                  25                  30

Leu Leu Leu Asn Ala Ser His Ser Ala Phe Leu Pro Leu Gly Leu Lys
        35                  40                  45

Val Thr Ile Val Gly Leu Tyr Leu Ala Val Cys Ile Gly Gly Leu Leu
    50                  55                  60

Gly Asn Cys Leu Val Met His Thr Lys Met Lys Thr Ala Thr Asn Ile
65                  70                  75                  80

Tyr Ile Phe Asn Leu Ala Leu Ala Asp Thr Leu Val Leu Leu Thr Leu
                85                  90                  95

Pro Phe Gln Gly Thr Asp Ile Leu Leu Gly Phe Trp Pro Phe Gly Asn
            100                 105                 110

Ala Leu Cys Lys Thr Val Ile Ala Ile Asp Tyr Tyr Asn Met Phe Thr
        115                 120                 125

Ser Thr Phe Thr Leu Thr Ala Met Ser Val Asp Arg Tyr Val Ala Ile
    130                 135                 140

Cys His Pro Ile Arg Ala Leu Asp Val Arg Thr Ser Ser Lys Ala Gln
145                 150                 155                 160

Ala Val Asn Val Ala Ile Trp Ala Leu Ala Ser Val Val Gly Val Pro
                165                 170                 175

Val Ala Ile Met Gly Ser Ala Gln Val Glu Asp Glu Glu Ile Glu Cys
            180                 185                 190

Leu Val Glu Ile Pro Ala Pro Gln Asp Tyr Trp Gly Pro Val Phe Ala
        195                 200                 205

Ile Cys Ile Phe Leu Phe Ser Phe Ile Ile Pro Val Leu Ile Ile Ser
    210                 215                 220

Val Cys Tyr Ser Leu Met Ile Arg Arg Leu Arg Gly Val Arg Leu Leu
225                 230                 235                 240

Ser Gly Ser Arg Glu Lys Asp Arg Asn Leu Arg Arg Ile Thr Arg Leu
                245                 250                 255

Val Leu Val Val Val Ala Val Phe Val Gly Cys Trp Thr Pro Val Gln
            260                 265                 270

Val Phe Val Leu Val Gln Gly Leu Gly Val Gln Pro Gly Ser Glu Thr
```

```
                275                 280                 285
Ala Val Ala Ile Leu Arg Phe Cys Thr Ala Leu Gly Tyr Val Asn Ser
    290                 295                 300

Cys Leu Asn Pro Ile Leu Tyr Ala Phe Leu Asp Glu Asn Phe Lys Ala
305                 310                 315                 320

Cys Phe Arg Lys Phe Cys Cys Ala Ser Ser Leu His Arg Glu Met Gln
                325                 330                 335

Val Ser Asp Arg Val Arg Ser Ile Ala Lys Asp Val Gly Leu Gly Cys
                340                 345                 350

Lys Thr Ser Glu Thr Val Pro Arg Pro Ala
                355                 360

<210> SEQ ID NO 18
<211> LENGTH: 439
<212> TYPE: DNA
<213> ORGANISM: Rattus norvegicus

<400> SEQUENCE: 18
gctcatggag gcgttcatgt gcctgttagt gtagttgtgc tgtgttctaa ggcctcagtg      60
gacggtgtct agcactgtgg ttacttgttt ctgtgccctg ttccaggaac tgtactgagt     120
ggctttgcag ggtgacagca tggagtccct ctttcctgct ccatactggg aggtcttgta     180
tggcagccac tttcaaggga acctgtccct cctaaatgag accgtacccc accacctgct     240
cctcaatgct agtcacagcg ccttcctgcc ccttggactc aaggtcacca tcgtggggct     300
ctacttggct gtgtgcatcg gggggctcct ggggaactgc ctcgtcatgt atgtcatcct     360
cagctgggag ggcattgagg gggactggag acagcaggca caccaagatg aagacagcta     420
ccaacattta catatttaa                                                   439

<210> SEQ ID NO 19
<211> LENGTH: 1243
<212> TYPE: DNA
<213> ORGANISM: Rattus norvegicus

<400> SEQUENCE: 19
gctcatggag gcgttcatgt gcctgttagt gtagttgtgc tgtgttctaa ggcctcagtg      60
gacggtgtct agcactgtgg ttacttgttt ctgtgccctg ttccaggaac tgtactgagt     120
ggctttgcag ggtgacagca tggagtccct ctttcctgct ccatactggg aggtcttgta     180
tggcagccac tttcaaggga acctgtccct cctaaatgag accgtacccc accacctgct     240
cctcaatgct agtcacagcg ccttcctgcc ccttggactc aaggtcacca tcgtggggct     300
ctacttggct gtgtgcatcg gggggctcct ggggaactgc ctcgtcatgt atgtcatcct     360
caggcacacc aagatgaaga cagctaccaa catttacata tttaatctgg cactggctga     420
taccctggtc ttgctaacac tgcccttcca gggcacagac atcctactgg gcttctggcc     480
atttgggaat gcactctgca agactgtcat tgctatcgac tactacaaca tgtttaccag     540
cacttttact ctgaccgcca tgagcgtaga ccgctatgtg gctatctgcc acccatccg      600 tgcccttgat gttcggacat ccagcaaagc ccaggctgtt aatgtggcca tatgggccct     660
ggcttcagtg gttggtgttc ctgttgccat catgggttca gcacaagtgg aagatgaaga     720
gatcgagtgc ctggtggaga tccctgcccc tcaggactat ggggccctg tattcgccat     780 ctgcatcttc cttttttcct tcatcatccc tgtgctgatc atctctgtct gctacagcct     840
catgattcga cgacttcgtg gtgtccgtct gctttcaggc tcccgggaga aggaccgaaa     900
```

| | |
|---|---|
| cctgcggcgt atcactcgac tggtgctggt agtggtggct gtgtttgtgg gctgctggac | 960 |
| gcctgtgcag gtgtttgtcc tggttcaagg actgggtgtt cagccaggta gtgagactgc | 1020 |
| agttgccatc ctgcgcttct gcacagccct gggctatgtc aacagttgtc tcaatcccat | 1080 |
| tctctatgct ttcctggatg agaacttcaa ggcctgcttt agaaagttct gctgtgcttc | 1140 |
| atccctgcac cgggagatgc aggtttctga tcgtgtgcgg agcattgcca aggatgttgg | 1200 |
| ccttggttgc aagacttctg agacagtacc acggccagca tga | 1243 |

<210> SEQ ID NO 20
<211> LENGTH: 1228
<212> TYPE: DNA
<213> ORGANISM: Rattus norvegicus

<400> SEQUENCE: 20

| | |
|---|---|
| gctcatggag gcgttcatgt gcctgttagt gtagttgtgc tgtgttctaa ggcctcagtg | 60 |
| gacggtgtct agcactgtgg ttacttgttt ctgtgccctg ttccaggaac tgtactgagt | 120 |
| ggctttgcag ggtgacagca tggagtccct cttcctgct ccatactggg aggtcttgta | 180 |
| tggcagccac tttcaaggga acctgtccct cctaaatgag accgtacccc accacctgct | 240 |
| cctcaatgct agtcacagcg ccttcctgcc ccttggactc aaggtcacca tcgtggggct | 300 |
| ctacttggct gtgtgcatcg gggggctcct ggggaactgc ctcgtcatgc acaccaagat | 360 |
| gaagacagct accaacattt acatatttaa tctggcactg gctgataccc tggtcttgct | 420 |
| aacactgccc ttcagggca cagacatcct actgggcttc tggccatttg ggaatgcact | 480 |
| ctgcaagact gtcattgcta tcgactacta acacatgttt accagcactt ttactctgac | 540 |
| cgccatgagc gtagaccgct atgtggctat ctgccaccct atccgtgccc ttgatgttcg | 600 |
| gacatccagc aaagcccagg ctgttaatgt ggccatatgg gccctggctt cagtggttgg | 660 |
| tgttcctgtt gccatcatgg gttcagcaca agtggaagat gaagagatcg agtgcctggt | 720 |
| ggagatccct gcccctcagg actattgggg ccctgtattc gccatctgca tcttcctttt | 780 |
| ttccttcatc atccctgtgc tgatcatctc tgtctgctac agcctcatga ttcgacgact | 840 |
| tcgtggtgtc cgtctgcttt caggctcccg ggagaaggac cgaaacctgc ggcgtatcac | 900 |
| tcgactggtg ctggtagtgg tggctgtgtt tgtgggctgc tggacgcctg tgcaggtgtt | 960 |
| tgtcctggtt caaggactgg gtgttcagcc aggtagtgag actgcagttg ccatcctgcg | 1020 |
| cttctgcaca gccctgggct atgtcaacag ttgtctcaat cccattctct atgctttcct | 1080 |
| ggatgagaac ttcaaggcct gctttagaaa gttctgctgt gcttcatccc tgcaccggga | 1140 |
| gatgcaggtt tctgatcgtg tgcggagcat tgccaaggat gttggccttg gttgcaagac | 1200 |
| ttctgagaca gtaccacggc cagcatga | 1228 |

<210> SEQ ID NO 21
<211> LENGTH: 887
<212> TYPE: DNA
<213> ORGANISM: Rattus norvegicus

<400> SEQUENCE: 21

| | |
|---|---|
| gctcatggag gcgttcatgt gcctgttagt gtagttgtgc tgtgttctaa ggcctcagtg | 60 |
| gacggtgtct agcactgtgg ttacttgttt ctgtgccctg ttccaggaac tgtactgagt | 120 |
| ggctttgcag ggtgacagca tggagtccct cttcctgct ccatactggg aggtcttgta | 180 |
| tggcagccac tttcaaggga acctgtccct cctaaatgag accgtacccc accacctgct | 240 |
| cctcaatgct agtcacagcg ccttcctgcc ccttggactc aaggtcacca tcgtggggct | 300 |

```
ctacttggct gtgtgcatcg gggggctcct ggggaactgc ctcgtcatgt atgtcatcct    360
cagagatcga gtgcctggtg gagatccctg cccctcagga ctattggggc cctgtattcg    420
ccatctgcat cttcctttt tccttcatca tccctgtgct gatcatctct gtctgctaca    480
gcctcatgat tcgacgactt cgtggtgtcc gtctgctttc aggctcccgg gagaaggacc    540
gaaacctgcg gcgtatcact cgactggtgc tggtagtggt ggctgtgttt gtgggctgct    600
ggacgcctgt gcaggtgttt gtcctggttc aaggactggg tgttcagcca ggtagtgaga    660
ctgcagttgc catcctgcgc ttctgcacag ccctgggcta tgtcaacagt tgtctcaatc    720
ccattctcta tgctttcctg gatgagaact tcaaggcctg ctttagaaag ttctgctgtg    780
cttcatccct gcaccgggag atgcaggttt ctgatcgtgt gcggagcatt gccaaggatg    840
ttggccttgg ttgcaagact tctgagacag taccacggcc agcatga                 887
```

<210> SEQ ID NO 22
<211> LENGTH: 2534
<212> TYPE: DNA
<213> ORGANISM: Homo sapiens

<400> SEQUENCE: 22

```
cctgctctgc acctgtcgtc gactgccagc cggctgaggg cgggggtctc cacggtggtc     60
ccagctccca aggaggttgc agaagtaccg tacagagtgg atttgcaggg cagtggcatg    120 gagccctct tccccgcgcc gttctgggag gttatctacg gcagccacct tcagggcaac    180
ctgtccctcc tgagccccaa ccacagtctg ctgccccgc atctgctgct caatgccagc    240
cacggcgcct tcctgcccct cgggctcaag gtcaccatcg tggggctcta cctggccgtg    300
tgtgtcggag ggtcctgggg gaactgcctt gtcatgtacg tcatcctcag gcacaccaaa    360
atgaagacag ccaccaatat ttacatcttt aacctggccc tggccgacac tctggtcctg    420
ctgacgctgc ccttccaggg cacggacatc ctcctgggct tctggccgtt tgggaatgcg    480
ctgtgcaaga cagtcattgc cattgactac tacaacatgt tcaccagcac cttcacccta    540
actgccatga gtgtggatcg ctatgtagcc atctgccacc ccatccgtgc cctcgacgtc    600
cgcacgtcca gcaaagccca ggctgtcaat gtggccatct gggcctggc ctctgttgtc    660 ggtgttcccg ttgccatcat gggctcggca caggtcgagg atgaagagat cgagtgcctg    720
gtggagatcc ctaccctca ggattactgg ggcccggtgt ttgccatctg catcttcctc    780
ttctccttca tcgtccccgt gctcgtcatc tctgtctgct acagcctcat gatccggcgg    840
ctccgtggag tccgcctgct ctcgggctcc cgagagaagg accggaacct gcggcgcatc    900
actcggctgg tgctggtggt agtggctgtg ttcgtgggct gctggacgcc tgtccaggtc    960
ttcgtgctgg cccaagggct gggggttcag ccgagcagcg agactgccgt ggccattctg   1020
cgcttctgca cggccctggg ctacgtcaac agctgcctca cccccatcct ctacgccttc   1080
ctggatgaga acttcaaggc ctgcttccgc aagttctgct gtgcatctgc cctgcgccgg   1140
gacgtgcagg tgtctgaccg cgtgcgcagc attgccaagg acgtggccct ggcctgcaag   1200
acctctgaga cggtaccgcg gcccgcatga ctaggcgtgg acctgcccat ggtgcctgtc   1260
agcccgcaga gccatctac gcccaacaca gagctcacac aggtcactgc tctctaggcg   1320
gacacaccct gggccctgag catccagagc ctgggatggg cttttccctg tgggccaggg   1380
atgctcggtc ccagaggagg acctagtgac atcatgggac aggtcaaagc attagggcca   1440
cctccatggc cccagacaga ctaaagctgc cctcctggtg cagggccgag gggacacaag   1500
```

-continued

```
gacctacctg gaagcagctg acatgctggt ggacggccgt tactggagcc cgtgcccctc     1560
cctcccgtg cttcatgtga ctcttggcct ctctgctgct gcgttggcag aaccctgggt      1620
gggcaggcac ccggaggagg agcagcagct gtgtcatcct gtgccccca tgtgctgtgt      1680
gctgtttgca tggcagggct ccagctgcct tcagccctgt gacgtctcct cagggcagct    1740
ggacaggctt ggcacggccc gggaagtgca gcaggcagct tttctttggg gtgggacttg    1800
ccctgagctt ggagctgcca cctggaggac ttgcctgttc cgactccacc tgtgcagccg    1860
gggccacccc aggagaaagt gtccaggtgg gggctggcag tccctggctg cagaccccga    1920
gctggccctc ggaccgcacc tctgaaggtt ttctgtgtgc tgcacggtgc aggcctcatc    1980
cctgactgca gcttgactct gggcccaacc cccatttccc ttcaggagac cagcgagagg    2040
ccctggccat ccctccagcg gtgcaatgaa ctatatgctg tggaccgtca acccagccct    2100
gcttctcagt gtggggcagg tgtctcagga cgaaggcgcc gcgtgaccac atgggcagct    2160
ctgttcacaa agtggaggcc tcgttttcct ggtcttgact gctctgtttg ggtgggagaa    2220
gattctctgg gggtccccac atcctcccaa ggctcccctc acagcctctc ctttgcttga    2280
agccagaggt cagtggccgt gctgtgttgc ggggaagctg tgtggaagga gaagctggtg    2340
gccacagcag agtcctgctc tggggacgcc tgcttcattt acaagcctca agatggctct    2400
gtgtagggcc tgagcttgct gcccaacggg aggatggctt cacagcagag ccagcatgag    2460
gggtggggcc tggcagggct tgcttgagcc aaactgcaaa ggctgtggtg gctgtgagga    2520
cactgcgggg gttg                                                       2534
```

<210> SEQ ID NO 23
<211> LENGTH: 171
<212> TYPE: PRT
<213> ORGANISM: Rattus norvegicus

<400> SEQUENCE: 23

```
Met Glu Ser Leu Phe Pro Ala Pro Tyr Trp Glu Val Leu Tyr Gly Ser
1               5                   10                  15

His Phe Gln Gly Asn Leu Ser Leu Leu Asn Glu Thr Val Pro His His
            20                  25                  30

Leu Leu Leu Asn Ala Ser His Ser Ala Phe Leu Pro Leu Gly Leu Lys
        35                  40                  45

Val Thr Ile Val Gly Leu Tyr Leu Ala Val Cys Ile Gly Gly Leu Leu
    50                  55                  60

Gly Asn Cys Leu Val Met Tyr Val Ile Leu Arg Asp Arg Val Pro Gly
65                  70                  75                  80

Gly Asp Pro Cys Pro Ser Gly Leu Leu Gly Pro Cys Ile Arg His Leu
                85                  90                  95

His Leu Pro Phe Phe Leu His His Pro Cys Ala Asp His Leu Cys Leu
            100                 105                 110

Leu Gln Pro His Asp Ser Thr Thr Ser Trp Cys Pro Ser Ala Phe Arg
        115                 120                 125

Leu Pro Gly Glu Gly Pro Lys Pro Ala Ala Tyr His Ser Thr Gly Ala
    130                 135                 140

Gly Ser Gly Gly Cys Val Cys Gly Leu Leu Asp Ala Cys Ala Gly Val
145                 150                 155                 160

Cys Pro Gly Ser Arg Thr Gly Cys Ser Ala Arg
                165                 170
```

<210> SEQ ID NO 24

```
<211> LENGTH: 17
<212> TYPE: PRT
<213> ORGANISM: Rattus norvegicus

<400> SEQUENCE: 24

Phe Gly Gly Phe Thr Gly Ala Arg Lys Ser Ala Arg Lys Leu Ala Asn
1               5                   10                  15

Gln

<210> SEQ ID NO 25
<211> LENGTH: 35
<212> TYPE: DNA
<213> ORGANISM: Rattus norvegicus

<400> SEQUENCE: 25
gttggaggta agaggggccc tgttccagga actgt                                35

<210> SEQ ID NO 26
<211> LENGTH: 35
<212> TYPE: DNA
<213> ORGANISM: Rattus norvegicus

<400> SEQUENCE: 26
tcctcaggta ggctgggttt ttttccagct gggag                                35

<210> SEQ ID NO 27
<211> LENGTH: 35
<212> TYPE: DNA
<213> ORGANISM: Rattus norvegicus

<400> SEQUENCE: 27
acagcaggtg aggactttc attgctagac aatac                                 35

<210> SEQ ID NO 28
<211> LENGTH: 35
<212> TYPE: DNA
<213> ORGANISM: Rattus norvegicus

<400> SEQUENCE: 28
acattcagtt agatatggtc tctacaggc acacc                                 35

<210> SEQ ID NO 29
<211> LENGTH: 35
<212> TYPE: DNA
<213> ORGANISM: Rattus norvegicus

<400> SEQUENCE: 29
gatgaaggtc agtgggtctc tcctgcagag atcga                                35

<210> SEQ ID NO 30
<211> LENGTH: 7
<212> TYPE: DNA
<213> ORGANISM: Rattus norvegicus

<400> SEQUENCE: 30 agcatga                                                                7

<210> SEQ ID NO 31
<211> LENGTH: 90
<212> TYPE: DNA
<213> ORGANISM: Rattus norvegicus

<400> SEQUENCE: 31
```

```
gaaggtcagt gggtggtcct cctccctgac tcattagttt cccatggttc ttgctggtcc      60
ctctgacccc atttctctcc tgcagagatc                                       90

<210> SEQ ID NO 32
<211> LENGTH: 29
<212> TYPE: PRT
<213> ORGANISM: Rattus norvegicus

<400> SEQUENCE: 32

Glu Gly Gln Trp Val Val Leu Leu Pro Asp Ser Leu Val Ser His Gly
1               5                   10                  15

Ser Cys Trp Ser Leu Pro His Phe Ser Pro Ala Glu Ile
            20                  25

<210> SEQ ID NO 33
<211> LENGTH: 27
<212> TYPE: PRT
<213> ORGANISM: Rattus norvegicus

<400> SEQUENCE: 33

Gln Trp Val Val Leu Leu Pro Asp Ser Leu Val Ser His Gly Phe Leu
1               5                   10                  15

Leu Val Pro Leu Pro Pro Asn Pro Ser Pro Ala
            20                  25

<210> SEQ ID NO 34
<211> LENGTH: 3200
<212> TYPE: DNA
<213> ORGANISM: Rattus norvegicus

<400> SEQUENCE: 34
ggatatagag actctgtacg aggtgcagga actctctggg ggtttgtgtg ccagcttttg      60 ccggggtgg catggggatg aaaaaggaag tgatggaagg gcaggagag agagagagag       120 agagagagag agagagagag agagagagag agagagagca acagagagtg catacttatg    180
tgctatatat ctaggggcct ttctctgttc cagtggtggt agcacatgcc tttaatccta    240
gcattcagga agcagaggca gatgtgtctc taagttctag gacagccaag gctacacaga    300
caaatcctgt ctctaacctg ttaacttccc caaacaaaac aaaacaaaac agagcaaagc    360
aaagcaaagc aaaacaaaac aaaacaacat tttcgagtgt tggagcctca cgtctacttc    420
tgggtgagca tttctctgta tacatcttga atgtgttctt gtgtctaagg ctgtgcgtgt    480
atgtgtgtct gaattcctgt tcatgtctct atttttgtgt tcatggatgt ccccattgtg    540
tgtcctaggg cctgagtgtg tttgtgttgg gtgagcccat cacattatat gtttgttaat    600
cttttggctc ctacttggtg tggagcctag gggtctggt ctggtaatct cctttttttt    660 ttttttttt tggctttctt ctccaacctg cacagcccct ccttctctca gccgcagcct    720 tctgccccctc cccttctgg ctgccgcacc ggctgctgcg tctagtcaat atcttatctt    780
ccgagcagga gctaggagcc attcccagcc gcagcagacc ccaatctaga gtgagagtca    840
ttgctcagtc cactgtgctc ctgcctgccc gcctttctgc taagcattgg ggtctatttt    900
ggcccagctt ctgaagaggc tgtgtgtgcc gttggaggta agagggctc ctgctgcctc     960 tgacagagct gggggtgggg gagccctggg aagtagctat gtgaagtgcc tgagccttag   1020
gcatttctgg ataaattcca tgccttttgt gccccagtgt accttaggat ggtttaggca    1080 tttttttgtgt ttggctggct gtgagcccct gggtcttggt gggtggacat gtgtgcttgt   1140
gtagctacgt tgcttctgtg cgggtctata accctaatgt gaggtaacct tgtaggtaaa   1200
```

```
tgtgctccca tgcctctgtg tgtgtcacca tgtgcccacg ggcatgtctg cctttgtctg  1260
tgtccgtgtg tctgtgtgtg tgcctagtgt ttgtgcatgc tcatggaggc gttcatgtgc  1320
ctgttagtgt agttgtgctg tgttctaagg cctcagtgga cggtgtctag cactgtggtt  1380
acttgtttct gtgccctgtt ccaggaactg tactgagtgg ctttgcaggg tgacagcatg  1440
gagtccctct ttcctgctcc atactgggag gtcttgtatg cagccactt tcaagggaac  1500 ctgtccctcc taaatgagac cgtaccccac cacctgctcc tcaatgctag tcacagcgcc  1560
ttcctgcccc ttggactcaa ggtcaccatc gtggggctct acttggctgt gtgcatcggg  1620
gggctcctgg ggaactgcct cgtcatgtat gtcatcctca ggtaggctgg gccccatcag  1680
tctgtgaagg gggaacctga ggcaggaggc tgttctgggt gaatctgaac ttccagctgg  1740
gagggcattg agggggactg gagacagcag gtgaggactt gaatgccaga atggggacat  1800
tgggaagaca tgggaggtcc ttgaatggtg aataactaga gcaaggttct ttttcattgc  1860
tagacaatac tgtgcagttg aagacacag atctttgatg aactttacag gcagtgccct  1920
gaaaagcctc tgagagaagt cttaagagag actgaggaga gaagacagca tctctctctc  1980
ttgattcatt ccacaaactc acattcaggt tagatatgca ctcaggtact cctccatgcc  2040 cccaacttt ccagggtagt cttgtcattg atttggaacc tttctgtaga tcttctcctt  2100
gtcctctaca ggcacaccaa gatgaagaca gctaccaaca tttacatatt taatctggca  2160
ctggctgata ccctggtctt gctaacactg cccttccagg gcacagacat cctactgggc  2220
ttctggccat ttgggaatgc actctgcaag actgtcattg ctatcgacta ctacaacatg  2280
tttaccagca ctttttactct gaccgccatg agcgtagacc gctatgtggc tatctgccac  2340
cctatccgtg cccttgatgt tcggacatcc agcaaagccc aggctgttaa tgtggccata  2400
tgggccctgg cttcagtggt tggtgttcct gttgccatca tgggttcagc acaagtggaa  2460
gatgaaggtc agtgggtggt cctcctccct gactcattag tttcccatgg ttcttgctgg  2520
tccctctgac cccatttctc tcctgcagag atcgagtgcc tggtggagat ccctgcccct  2580
caggactatt ggggccctgt attcgccatc tgcatcttcc ttttttcctt catcatccct  2640
gtgctgatca tctctgtctg ctacagcctc atgattcgac gacttcgtgg tgtccgtctg  2700
ctttcaggct cccgggagaa ggaccgaaac ctgcggcgta tcactcgact ggtgctggta  2760
gtggtggctg tgtttgtggg ctgctggacg cctgtgcagg tgtttgtcct ggttcaagga  2820
ctgggtgttc agccaggtag tgagactgca gttgccatcc tgcgcttctg cacagccctg  2880
ggctatgtca acagttgtct caatcccatt ctctatgctt tcctggatga aacttcaag  2940 gcctgcttta gaaagttctg ctgtgcttca tccctgcacc gggagatgca ggtttctgat  3000
cgtgtgcgga gcattgccaa ggatgttggc cttggttgca agacttctga gacagtacca  3060
cggccagcat gactaggcgt ggacctgccc atggtgcctg tcagcccaca gagcccatct  3120
acacccaaca cggagctcac acaggtcact gctctctagg ttgaccctga accttgagca  3180
tctggagcct tgaatggctt                                              3200
```

<210> SEQ ID NO 35
<211> LENGTH: 429
<212> TYPE: PRT
<213> ORGANISM: Rattus norvegicus

<400> SEQUENCE: 35

```
Met Glu Ser Leu Phe Pro Ala Pro Tyr Trp Glu Val Leu Tyr Gly Ser
1               5                   10                  15
```

-continued

His Phe Gln Gly Asn Leu Ser Leu Leu Asn Glu Thr Val Pro His His
         20                  25                  30

Leu Leu Leu Asn Ala Ser His Ser Ala Phe Leu Pro Leu Gly Leu Lys
         35                  40                  45

Val Thr Ile Val Gly Leu Tyr Leu Ala Val Cys Ile Gly Gly Leu Leu
         50                  55                  60

Gly Asn Cys Leu Val Met Tyr Val Ile Leu Ser Glu Gly Ile Glu Gly
 65                  70                  75                  80

Asp Trp Arg Gln Gln Thr Ile Leu Cys Ser Trp Lys Thr Gln Ile Phe
                 85                  90                  95

Asp Glu Leu Tyr Arg Gln Cys Pro Glu Lys Pro Leu Arg Glu Val Leu
                100                 105                 110

Arg Glu Thr Glu Glu Arg Gln His Leu Ser Leu Leu Ile His Ser
                115                 120                 125

Thr Asn Ser His Ser Gly Thr Pro Arg His Thr Lys Met Lys Thr Ala
        130                 135                 140

Thr Asn Ile Tyr Ile Phe Asn Leu Ala Leu Ala Asp Thr Leu Val Leu
145                 150                 155                 160

Leu Thr Leu Pro Phe Gln Gly Thr Asp Ile Leu Leu Gly Phe Trp Pro
                165                 170                 175

Phe Gly Asn Ala Leu Cys Lys Thr Val Ile Ala Ile Asp Tyr Tyr Asn
                180                 185                 190

Met Phe Thr Ser Thr Phe Thr Leu Thr Ala Met Ser Val Asp Arg Tyr
                195                 200                 205

Val Ala Ile Cys His Pro Ile Arg Ala Leu Asp Val Arg Thr Ser Ser
        210                 215                 220

Lys Ala Gln Ala Val Asn Val Ala Ile Trp Ala Leu Ala Ser Val Val
225                 230                 235                 240

Gly Val Pro Val Ala Ile Met Gly Ser Ala Gln Val Glu Asp Glu Glu
                245                 250                 255

Ile Glu Cys Leu Val Glu Ile Pro Ala Pro Gln Asp Tyr Trp Gly Pro
                260                 265                 270

Val Phe Ala Ile Cys Ile Phe Leu Phe Ser Phe Ile Ile Pro Val Leu
            275                 280                 285

Ile Ile Ser Val Cys Tyr Ser Leu Met Ile Arg Arg Leu Arg Gly Val
        290                 295                 300

Arg Leu Leu Ser Gly Ser Arg Glu Lys Asp Arg Asn Leu Arg Arg Ile
305                 310                 315                 320

Thr Arg Leu Val Leu Val Val Ala Val Phe Val Gly Cys Trp Thr
                325                 330                 335

Pro Val Gln Val Phe Val Leu Val Gln Gly Leu Gly Val Gln Pro Gly
            340                 345                 350

Ser Glu Thr Ala Val Ala Ile Leu Arg Phe Cys Thr Ala Leu Gly Tyr
        355                 360                 365

Val Asn Ser Cys Leu Asn Pro Ile Leu Tyr Ala Phe Leu Asp Glu Asn
    370                 375                 380

Phe Lys Ala Cys Phe Arg Lys Phe Cys Cys Ala Ser Ser Leu His Arg
385                 390                 395                 400

Glu Met Gln Val Ser Asp Arg Val Arg Ser Ile Ala Lys Asp Val Gly
                405                 410                 415

Leu Gly Cys Lys Thr Ser Glu Thr Val Pro Arg Pro Ala
            420                 425

```
<210> SEQ ID NO 36
<211> LENGTH: 15
<212> TYPE: DNA
<213> ORGANISM: Rattus norvegicus

<400> SEQUENCE: 36
gtatgtcatc ctcag                                                    15
```

ORPHANIN FQ RECEPTOR NUCLEIC ACIDS

The present invention claims priority to provisional patent application serial No. 60/272,429 filed Mar. 1, 2001, which is herein incorporated by reference in its entirety.

FIELD OF THE INVENTION

The present invention provides Orphanin-FQ receptor nucleic acid sequences. Specifically, the present invention provides nucleic acid sequences of differentially expressed splice variants of the Orphanin FQ receptor. The present invention also provides methods of using the Orphanin FQ receptor nucleic acid sequences for the identification of pharmaceutical agents and the generation of animal models of Orphanin FQ receptor-mediated disease states.

BACKGROUND

The use (and abuse) of opiates, archetypally opium and morphine, have been known since antiquity (reviewed in Brownstein, Proc. Natl. Acad. Sci. USA 90:5391 [1993]). Since the nineteenth century, chemical characterization and synthesis of a number of morphine analogues have been achieved in an effort to discover a compound with the analgesic effects of morphine that lacks or is substantially attenuated in its addictive potential. These efforts have proven fruitless to date.

The biology behind the reasons why morphine and morphine-like compounds display both analgesic and addictive properties was first elucidated by the discovery of endogenous morphine-like compounds termed enkephalins (See e.g., DiChara and North, Trends in Pharmacol. Sci. 13:185 [1992] for review). Accompanying this finding of an endogenous opiate was the biochemical evidence for a family of related but distinct opiate receptors, each of which displays a unique pharmacological profile of response to opiate agonists and antagonists (See e.g., McKnight and Rees, Neurotransmissions 7:1 [1991] for review). To date, four distinct opiate receptors have been described by their pharmacological profiles and anatomical distribution: these comprise the mu, delta, kappa and sigma receptors.

In 1991, U.S. pharmaceutical companies spent an estimated $7.9 billion on research and development devoted to identifying new therapeutic agents (Pharmaceutical Manufacturers Association). The magnitude of this amount is due, in part, to the fact that the hundreds, if not thousands, of chemical compounds must be tested in order to identify a single effective therapeutic agent that does not engender unacceptable levels of undesirable or deleterious side effects. There is an increasing need for economical methods of testing large numbers of chemical compounds to quickly identify those compounds that are likely to be effective in treating disease.

This is of particular importance for psychoactive and psychotropic drugs, due to their pharmacological importance and their potential to greatly benefit or greatly harm human patients All treated with such drugs. At present, few such economical systems exist. Conventional screening methods require the use of animal brain slices in binding assays as a first step. This is suboptimal for a number of reasons, including interference in the binding assay by non-specific binding of heterologous (i.e., non-receptor) cell surface proteins expressed by brain cells in such slices; differential binding by cells other than neuronal cells present in the brain slice, such as glial cells or blood cells; and the possibility that putative drug binding behavior in animal brain cells will differ from the binding behavior in human brain cells in subtle but critical ways. For these and other reasons, development of in vitro screening methods for psychotropic drugs has numerous advantages and is a major research goal in the pharmaceutical industry.

SUMMARY OF THE INVENTION

The present invention provides Orphanin FQ receptor nucleic acid sequences. Specifically, the present invention provides nucleic acid sequences of differentially expressed splice variants of the Orphanin FQ receptor. The present invention also provides methods of using the Orpbanin FQ receptor nucleic acid sequences for the identification of pharmaceutical agents and the generation of animal models of Orphanin FQ receptor-mediated disease states.

In some embodiments, the present invention provides an isolated OFQR nucleic acid sequence. The present invention is not limited to a particular isolated OFQR nucleic acid sequence. Indeed, a variety of sequences are contemplated. For example, in some embodiments, the present invention provides a composition comprising an isolated nucleic acid sequence encoding a polypeptide that binds to Orphanin FQ, wherein the nucleic acid is at least 85% identical to a nucleic acid sequence selected from the group including, but not limited to, SEQ ID NOs: 9, 10, 12, 14, 16, 18, 19, 20, and 21. In some embodiments, the nucleic acid is selected from the group including, but not limited to, SEQ ID NOs; 9, 10, 12, 14, 16, 18, 19, 20, and 21. In some embodiments, the nucleic acid is at least 90% identical to a nucleic acid sequence selected from the group including, but not limited to, of SEQ ID NOs: 9, 10, 12, 14, 16, 18, 19, 20, and 21. In other embodiments, the nucleic acid hybridizes under conditions of low stringency to a nucleic acid is selected from the group including, but not limited to, SEQ ID NOs: 9, 10, 12, 14, 16, 18, 19, 20, and 21. In some embodiments, the present invention provides a vector comprising the nucleic acid sequences described herein. In further embodiments, the present invention provides a host cell comprising the vector. In yet other embodiments, the present invention provides an animal comprising the host cell. In some embodiments, the animal is a non-human mammal. In some preferred embodiments, the animal expresses a polypeptide selected from the group consisting of SEQ ID NOs: 11, 13, 15, 17 and 23. In some embodiments, the nucleic acid sequence encodes a polypeptide that binds to Orphanin FQ, wherein the polypeptide is at least 95% identical to a polypeptide selected from the group consisting of SEQ ID NOs: 11, 13, 15, 17 and 23.

The present invention also provides a composition comprising an isolated nucleic acid sequence selected from the group including, but not limited to, SEQ ID NOs: 9, 10, 12, 14, 16, 18, 19, 20, and 21. In some embodiments, the nucleic acid sequence is SEQ ID NO: 9.

The present invention further provides an OFQR polypeptide. The present invention is not limited to a particular OFQR polypeptide. Indeed, a variety of OFQR polypeptides are contempled. For example, in some embodiments, the present invention further provides a composition comprising an isolated polypeptide sequence that binds to Orphanin FQ, wherein the polypeptide is at least 95% identical to a polypeptide selected from the group consisting of SEQ ID NOs: 11, 13, 15, 17 and 23. In some embodiments, the polypeptide is selected from the group including, but not limited to, SEQ ID NOs: 11, 13, 15, 17 and 23.

The present invention provides a method for screening test compounds for the ability to alter the level of interaction between Orphanin FQ and OFQR, comprising: providing at least one OFQR polypeptide (e.g., including but not limited to, those selected from the group consisting of SEQ ID NOs: 11, 13, 15, 17, and 23); an orphanin FQ peptide; and one or more test compounds; and combining in any order, at least one OFQR polypeptide, the orphanin FQ peptide, and the one or more test compounds under conditions such that the OFQR polypeptide sequence, the orphanin FQ peptide, and the test compound can interact; detecting the level of interaction between the OFQR polypeptide sequence and the orphanin FQ peptide; and comparing the level of interaction of the OFQR polypeptide sequence and the orphanin FQ peptide in the presence of the test compound to the level of interaction in the absence of the test compound.

The present invention also provides a method for screening test compounds for the ability to bind to OFQR, comprising: providing at least one polypeptide sequence selected from the group consisting of SEQ ID NOs: 11, 13, 15, 17, and 23; one or more test compounds; and combining the at least one polypeptide sequence selected from the group consisting of SEQ ID NOs: 11, 13, 15, 17, and 23 and the one or more test compounds under conditions such that the polypeptide sequence and the test compound can interact; and detecting the presence or absence of binding between the polypeptide sequence and the test compound.

The present invention further provides a method of screening test compounds for their ability to alter OFQR signaling activity, comprising: providing at least one polypeptide sequence selected from the group consisting of SEQ ID NOs: 11, 13, 15, 17, and 23; a test compound suspected of altering OFQR signaling activity; and contacting the test compound with the polypeptide; and comparing the level of signaling activity of the polypeptide in presence of the test compound to the level of signaling in the absence of the test compound. In some embodiments, the polypeptide is expressed in a cell. In some embodiments the method further comprises providing a reporter gene construct comprising a reporter gene. In some embodiments, the step of determining if the compound alters the signaling of the polypeptide comprises detecting expression of the reporter gene.

DESCRIPTION OF THE FIGS.

The following figures form part of the present specification and are included to further demonstrate certain aspects and embodiments of the present invention. The invention may be better understood by reference to one or more of these figures in combination with the description of specific embodiments presented herein.

FIG. 1 shows the structure of the rat OFQ receptor gene. (A) Restriction map and exon location. The restriction sites for Pst I (P), Acc I (A), and Sac I (S) are shown with the relative distances of each exon. (B) mRNA organization. Shaded and clear rectangles with size (bp) represent exons of the open reading frame and the untranslated regions, respectively. The ATG translation initiation codon is located in exon 2, and the TGA termination codon is located in exon 6.

FIG. 2 shows the nucleotide (SEQ ID NO:34) and deduced amino acid (SEQ ID NO:35) sequences of the rat OFQ receptor gene. The five exons (uppercase) are underlined. The nucleotide sequence is numbered on the far left, relative to the first nucleotide of the translation initiation codon in exon 2. Amino acids are numbered on the far right and are by designated with single-letter symbols below each triplet codon. FIG. 2 also shows the nucleotide sequence of the 5' flanking region of the rat OFQ receptor gene. The nucleotide sequence is numbered relative to the first nucleotide (dA) of the translation initiation codon (far right). A tandem dinucleotide sequence (GA) at nt 2312–2251 and two (AAAAC)$_3$ repeat sequences at nt 1106–1053 are underlined. Potential binding sites for RNA polymerase II (TATA) are marked with boxes at nt 852–849 and at nt 272–269. Transcription initiation sites are indicated with arrows. The exons are in uppercase. The methionine (M) of the translation initiation codon is depicted with a single-letter symbol below the triplet codon (ATG) in exon 2. The sites of consensus motifs for transcription factors Ap2 and Sp1 are underlined and labeled.

FIG. 3 shows primer extension for the identification of the transcription initiation sites. The transcription initiation sites were identified as the cytosine at nt 750 (A) and the guanine at nt 139 (B) (see asterisks). Lanes A, C, G, and T indicate the size of the genomic DNA from dideoxy sequencing using the same primers that were used for the primer extension experiment. (C) Transcription initiation sites. CAP 1 is the transcription initiation site of mRNAs containing exon 1 by joining nt 501 in exon 1 to nt 33 in exon 2. CAP 2 is the transcription initiation site of mRNAs deleted for exon 1.

FIG. 4 shows PCR cloning of gene splice variants. The resulting PCR bands obtained from primers P5 and P10 using the RT-PCR products of either primer P9 located in exon 1 (A) or P3 contained in intron 1 sequence (B) in combination with primer P13, were subcloned into the M13 vector and sequenced by the dideoxy chain termination method. (C) Alternative splicing of the rat OFQR gene. OFQR-a (SEQ ID NO: 10) contained all six exons, whereas OFQR-e was deleted for exons 3, 4, and 5. Two mRNA variants, OFQR-b (SEQ ID NO:12) and -c (SEQ ID NO: 14) were deleted for exon 4 and for exons 3 and 4, respectively. OFQR-d (SEQ ID NO: 16) was the same isoform as OFQR-c, except for the 1 5-bp (GTATGTCATCCTCAG; SEQ ID NO:36) deletion in exon 2 at nt 243–257. OFQR-b' (SEQ ID NO:17), -c' (SEQ ID NO:19), -d' (SEQ ID NO:20) and-e' (SEQ ID NO:21) are mRNA variants deleted for exon 1. Shaded and clear boxes indicate exons for the open reading frames (corresponding to the polypeptide sequences for variant a (SEQ ID NO:11); variant b (SEQ ID NO:13); variant c (SEQ ID NO:15; variant d (SEQ ID NO:17; and variant e (SEQ ID NO:23) for the untranslated regions, respectively. The asterisks in exons 5 and 6 indicate the positions of early termination in protein coding regions. The putative open reading frames are (D) Translation of intron 5 and comparison of the amino acid homology to the published sequence. The nucleotide sequence (a; SEQ ID NO:31) of intron 5 is indicated by arrows and is depicted in the single-letter symbols below each triplet codon (b; SEQ ID NO:32), and compared to the amino acid sequence reported by Wang et al. (FEBS Lett. 348, 75 [1994]) (c; SEQ ID NO:33).

FIG. 5 shows Expression of alternative splicing in rat tissues. Either primer P9 (A) in exon 1 or P3 (B) in intron 1 in combination with P13 in the 3' untraslated region were used in PCR to produce full-length cDNAs. The primer P3 containing the 19-mer intron 1 sequence (shown in lowercase in Table 1) was designed to verify only exon 2 expression in mRNA. OFQR-c, -d, -c' and -d' could not be distinguished from one another due to minimal size differences (i.e., 15 bp). No message could be detected from kidney, heart, lung, or muscle. Multiple receptor forms containing exon 1 were expressed in various tissues (A), whereas those without exon 1 were restricted to brain (B). GAPDH served as an internal control (C).

FIG. 6 shows the nucleic acid sequence of SEQ ID NO: 9.

FIG. 7 shows the nucleic acid sequence of SEQ ID NO: 10.

FIG. 8 shows the amino acid sequence of SEQ ID NO: 11.

FIG. 9 shows the nucleic acid sequence of SEQ ID NO: 12.

FIG. 10 shows the amino acid sequence of SEQ ID NO: 13.

FIG. 11 shows the nucleic acid sequence of SEQ ID NO: 14.

FIG. 12 shows the amino acid sequence of SEQ ID NO: 15.

FIG. 13 shows the nucleic acid sequence of SEQ ID NO: 16.

FIG. 14 shows the amino acid sequence of SEQ ID NO: 17.

FIG. 15 shows the nucleic acid sequence of SEQ ID NO: 18.

FIG. 16 shows the nucleic acid sequence of SEQ ID NO: 19.

FIG. 17 shows the nucleic acid sequence of SEQ ID NO: 20.

FIG. 18 shows the nucleic acid sequence of SEQ ID NO: 21.

FIG. 19 shows the nucleic acid sequence of SEQ ID NO: 22.

FIG. 20 shows the amino acid sequence of SEQ ID NO: 23.

GENERAL DESCRIPTION OF THE INVENTION

Figure 1:
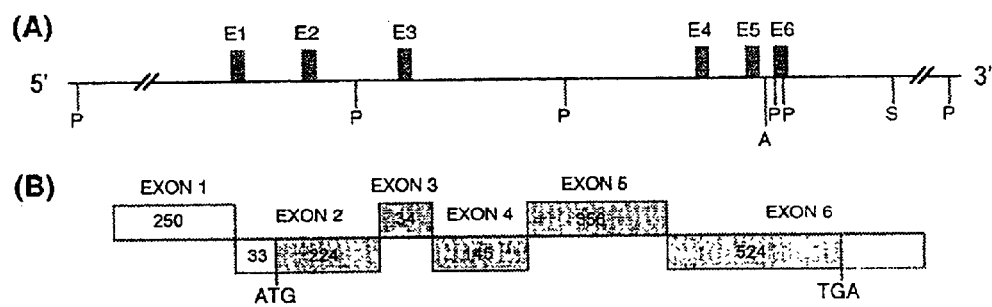

The present invention provides Orphanin FQ receptor nucleic acid sequences. Specifically, the present invention provides nucleic acid sequence of differentially expressed splice variants of the Orphanin FQ receptor. The present invention also provides methods of using the Orphanin FQ receptor nucleic acid sequences for the identification of pharmaceutical agents and the generation of animal models of Orphanin FQ receptor-mediated disease states.

Orphanin FQ (OFQ), also called nociceptin, is a 17-amino acid peptide (Phe-Gly-Gly-Phe-Thr-Gly-Ala-Arg-Lys-Ser-Ala-Arg-Lys-Leu-Ala-Asn-Gln; SEQ ID NO:24) isolated from the central nervous system. Research has shown that OFQ receptors (OFQRs) have the classical seven transmembrane-spanning domain structure of G protein-linked receptors and high sequence homology to opioid receptors (Bunzow et al., FEBS Lett. 347: 284 [1994]). OFQRs bear several similarities to opioid receptors in that they appear to inhibit adenylate cyclase through a $G_i$ protein, they activate inwardly rectifying $K^+$ channels, and they inhibit N-type voltage-operated $Ca^{2+}$ channels. However, OFQRs have a very low affinity for the classical opioid ligands (Darland et al., Trends Neurosci. 21, 215 [1998]). Similar or perhaps identical receptors in various species have been reported: in human, opioid receptor-like 1 (ORL1, Mollereau et al., FEBS Lett. 341, 331994); in rat, rat opioid receptor C (ROR-C, Fukuda et al., FEBS Lett. 343:42 [1994]), X-opioid receptor (XOR, Chen et al., FEBS Lett. 347:279 [1994]), LC132 (Bunzow et al., FEBS Lett. 347:284 [1994]), X-opioid receptor 1 (XOR1, Wang et al., supra), Hyp 8-1 (Wick et al., Brain Res. Mol. Brain Res. 27:37 [1994]), and C3 (Lachowicz et al., J. Neurochem. 64: 34 [1995]); and in mouse, opioid receptor C (MOR-C, Nishi et al., Biochem. Biophys. Res. Commun. 205:1353 [1994]) and $K_3$-related opioid receptor (KOR-3, Pan et al., Regul. Pept. 54, 217 [1994]; Pan et al., Mol. Pharmacol. 47:1180 [1995]; Pan et al., Gene 171:255 [1996a]). OFQ binds to these receptors with high affinity in a saturable manner (Reinscheid et al., Science 270:792 [1995]). Moreover, OFQ inhibits (with an $EC_{50}$ of about 1 nM) forskolin-induced cAMP accumulation in CHO cells transfected with the receptor; an effect that is not modified by opioid ligands (Meunier et al., Nature 377:532 [1995]; Reinscheid et al., supra). OFQ was shown to reduce, in a concentration-dependent manner, the electrically induced ileal contraction in guinea pig (Zhang et al., Brain Res. 772:102 [1997]), rat (Yazdani et al., Gastroenterology 116:108 [1999]), and pig (Osinski et al., Eur. J. Pharmacol. 365:281 [1999]). Intracerebroventricular OFQ administration was shown to induce hyperalgesia and decrease locomotor activity in mice (Meunier et al., supra; Reinscheid et al., supra), suggesting a modulatory or neurotransmitter role in the central nervous system, as has been reported for other central functions (for a review, see Darland et al., supra). Subsequently, OFQ was shown to have a dual effect on pain perception in mice—initial hyperalgesia followed by analgesia (Rossi et al., J. Pharmacol. Exp. Ther. 282:858 [1997]). Although the analgesic effect can be blocked by classical opioid antagonists, it is not mediated by traditional δ-, κ- and μ-opioid receptors (Rossi et al., [1997] supra; Rossi et al., Brain Res. 792:327 [1998]; Noda et al., J. Biol. Chem. 273:18047 [1998]).

These observations suggest that OFQR subtypes may exist in the central nervous system. This hypothesis is supported by receptor binding studies of cerebral bomogenates or CHO cells that express OFQR chimeras (Mathis et al., Biochem. Biophys. Res. Commun. 230:462 [1997]; Pan et al., FEBS Lett. 395:207 [1996b]). OFQR mRNA expression has also been demonstrated in peripheral tissues such as rat intestine (Wang et al., supra), pig gastrointestinal tract (Osinski et al., 1999), and in human immune system cells such as lymphocytes and monocytes (Peluso et al., supra).

Accordingly, in some embodiments, the present invention provides genes encoding OFQ receptors, as well as isoforms (e.g., splice variants) expressed in different tissues. In other embodiments, the present invention provides drug screening assays for the identification of compounds that effect signaling by the different isoforms of the OFQR (e.g., agonists or antagonists). The present invention is not limited to any one mechanism. Indeed, an understanding of the mechanism is not necessary to practice the present invention. Nonetheless, it is contemplated that therapeutic agents are targeted to specific receptor isoforms, and can thus provide specific therapies with decreased side effects.

Definitions

To facilitate an understanding of the present invention, a number of terms and phrases are defined below:

As used herein the term "disease" refers to a deviation from the condition regarded as normal or average for members of a species, and which is detrimental to an affected individual under conditions that are not inimical to the majority of individuals of that species (e.g., diarrhea, by nausea, fever, pain, and inflammation etc).

As used herein, the term "therapeutic agent," refers to compositions that decrease the symptoms of a disease in a host. Such agents may additionally comprise pharmaceutically acceptable compounds (e.g., adjutants, excipients, stabilizers, diluents, and the like). In some embodiments, the therapeutic agents are administered in the form of topical emulsions, injectable compositions, ingestible solutions, and the like. When the route is topical, the form may be, for example, a spray (e.g., a nasal spray).

The terms "pharmaceutically acceptable" or "pharmacologically acceptable," as used herein, refer to compositions that do not substantially produce adverse allergic or immunological reactions when administered to a host (e.g., an animal or a human). As used herein, "pharmaceutically acceptable carrier" includes any and all solvents, dispersion media, coatings, wetting agents (e.g., sodium lauryl sulfate), isotonic and absorption delaying agents, disintrigrants (e.g., potato starch or sodium starch glycolate), and the like.

As used herein, the term "systemically active drugs" is used broadly to indicate a substance or composition that will produce a pharmacological response at a site remote from the point of application or entry into a subject.

As used herein, the term "agonist" refers to a compound (e.g., a drug) that has affinity for the cellular receptor (e.g., OFQR) of another drug or natural substance (e.g., Orphanin FQ) and that produces a physiological effect.

As used herein, the term "antagonist" refers to a compound (e.g., a drug) that binds to a cellular receptor (e.g., OFQR) for a hormone, neurotransmitter (e.g., Orphanin FQ), or another drug blocking the action of that substance without producing any physiologic effect itself.

The term "gene" refers to a nucleic acid (e.g., DNA) sequence that comprises coding sequences necessary for the production of a polypeptide or precursor (e.g., OFQR). The polypeptide can be encoded by a full length coding sequence or by any portion of the coding sequence so long as the desired activity or functional properties (e.g., ligand binding, signal transduction, etc.) of the full-length or fragment are retained. The term also encompasses the coding region of a structural gene and the including sequences located adjacent to the coding region on both the 5' and 3' ends for a distance of about 1 kb on either end such that the gene corresponds to the length of the full-length mRNA. The sequences that are located 5' of the coding region and which are present on the mRNA are referred to as 5' untranslated sequences. The sequences that are located 3' or downstream of the coding region and that are present on the mRNA are referred to as 3' untranslated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene that are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

In particular, the term "OFQR gene" refers to the full-length OFQR nucleotide sequence (e.g., contained in SEQ ID NO:9). Furthermore, the terms "OFQR nucleotide sequence" or "OFQR polynucleotide sequence" encompasses DNA, cDNA, and RNA (e.g., mRNA) sequences. It is also intended that the term encompass splice variants of OFQR (e.g., including but not limited to SEQ ID NOs: 10, 12, 14, 16, 18, 19, 20, and 21).

As used herein, the term "OFQR polypeptide" refers to polypeptides encoded by an OFQR gene. The term is intended to encompass variants of OFQR (e.g. splice variants of SEQ ID NOs: 11, 13, 15, 17, and 23) as well as mutants, homologs, and orthologs thereof.

As used herein, the terms "interact," "interaction," and "level of interaction" refer to a physical interaction (e.g., binding) between a polypeptide (e.g., an OFQR polypeptide) and a molecule (e.g., a ligand or a test compound). The level of interaction can be determined, for example, by using one of the binding assays described in Section IV below.

As used herein, the term "capable of binding" as in "capable of binding to orphanin FQ" refers to a polypeptide (e.g., an OFQR polypeptide) that is able to bind to a molecule (e.g., a ligand including but not limited to, orphanin FQ). Binding can be measured using any suitable assay, including but not limited to, those disclosed herein (See e.g., Section IV below).

As used herein the term "OFQR signaling activity" refers to one of the signaling activities mediated by the binding of orphanin FQ to OFQR (e.g., including but not limited to, one of the activities disclosed herein). Signaling can be measured using any suitable assay, including but not limited to, the reporter gene assay described in Section IV below. As used herein, the term "altering OFQR signaling activity" as in "the ability of a test compound to alter OFQR signaling activity" refers to an altered level of signaling (e.g., higher or lower) relative to the level of signaling in the absence of a test compound.

Where amino acid sequence is recited herein to refer to an amino acid sequence of a naturally occurring protein molecule, amino acid sequence and like terms, such as polypeptide or protein are not meant to limit the amino acid sequence to the complete, native amino acid sequence associated with the recited protein molecule.

In addition to containing introns, genomic forms of a gene may also include sequences located on both the 5' and 3' end of the sequences that are present on the RNA transcript. These sequences are referred to as "flanking" sequences or regions (these flanking sequences are located 5' or 3' to the non-translated sequences present on the mRNA transcript). The 5' flanking region may contain regulatory sequences such as promoters and enhancers that control or influence the transcription of the gene. The 3' flanking region may contain sequences that direct the termination of transcription, post-transcriptional cleavage and polyadenylation.

The term "wild-type" refers to a gene or gene product that has the characteristics of that gene or gene product when isolated from a naturally occurring source. A wild-type gene is that which is most frequently observed in a population and is thus arbitrarily designed the "normal" or "wild-type" form of the gene. In contrast, the terms "modified","mutant",and "variant" refer to a gene or gene product that displays modifications in sequence and or functional properties (i.e., altered characteristics) when compared to the wild-type gene or gene product. It is noted that naturally-occurring mutants can be isolated; these are identified by the fact that they have altered characteristics when compared to the wild-type gene or gene product.

As used herein, the terms "nucleic acid molecule encoding," "DNA sequence encoding," and "DNA encoding" refer to the order or sequence of deoxyribonucleotides along a strand of deoxyribonucleic acid. The order of these deoxyribonucleotides determines the order of amino acids along the polypeptide (protein) chain. The DNA sequence thus codes for the amino acid sequence.

DNA molecules are said to have "5' ends" and "3' ends" because mononucleotides are reacted to make oligonucleotides or polynucleotides in a manner such that the 5' phosphate of one mononucleotide pentose ring is attached to the 3' oxygen of its neighbor in one direction via a phosphodiester linkage. Therefore, an end of an oligonucleotides or polynucleotide, referred to as the "5' end" if its 5' phosphate is not linked to the 3' oxygen of a mononucleotide pentose ring and as the "3' end" if its 3' oxygen is not linked to a 5' phosphate of a subsequent mononucleotide pentose ring. As used herein, a nucleic acid sequence, even if internal to a larger oligonucleotide or polynucleotide, also may be said to have 5' and 3' ends. In either a linear or circular DNA molecule, discrete elements are referred to as being "upstream" or 5' of the "downstream" or 3' elements. This terminology reflects the fact that transcription proceeds in a 5' to 3' fashion along the DNA strand. The promoter and enhancer elements that direct transcription of a linked gene are generally located 5' or upstream of the coding region. However, enhancer elements can exert their effect even when located 3' of the promoter element and the coding region. Transcription termination and polyadenylation signals are located 3' or downstream of the coding region.

As used herein, the terms "an oligonucleotide having a nucleotide sequence encoding a gene" and "polynucleotide having a nucleotide sequence encoding a gene," means a nucleic acid sequence comprising the coding region of a gene or, in other words, the nucleic acid sequence that encodes a gene product. The coding region may be present in either a cDNA, genomic DNA, or RNA form. When present in a DNA form, the oligonucleotide or polynucleotide may be single-stranded (i.e., the sense strand) or double-stranded. Suitable control elements such as enhancers/promoters, splice junctions, polyadenylation signals, etc. may be placed in close proximity to the coding region of the gene if needed to permit proper initiation of transcription and/or correct processing of the primary RNA transcript. Alternatively, the coding region utilized in the expression vectors of the present invention may contain endogenous enhancers/promoters, splice junctions, intervening sequences, polyadenylation signals, etc. or a combination of both endogenous and exogenous control elements.

As used herein, the term "regulatory element" refers to a genetic element that controls some aspect of the expression of nucleic acid sequences. For example, a promoter is a regulatory element that facilitates the initiation of transcription of an operably linked coding region. Other regulatory elements include splicing signals, polyadenylation signals, termination signals, etc.

As used herein, the terms "complementary" or "complementarity" are used in reference to polynucleotides (i.e., a sequence of nucleotides) related by the base-pairing rules. For example, for the sequence "A-G-T," is complementary to the sequence "T-C-A." Complementarity may be "partial," in which only some of the nucleic acids bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods that depend upon binding between nucleic acids.

The term "homology" refers to a degree of complementarity. There may be partial homology or complete homology (i.e., identity). A partially complementary sequence is one that at least partially inhibits a completely complementary sequence from hybridizing to a target nucleic acid and is referred to using the functional term "substantially homologous." The term "inhibition of binding," when used in reference to nucleic acid binding, refers to inhibition of binding caused by competition of homologous sequences for binding to a target sequence. The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding (i.e., the hybridization) of a completely homologous to a target under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target that lacks even a partial degree of complementarity (e.g., less than about 30% identity); in the absence of non-specific binding the probe will not hybridize to the second non-complementary target.

The art knows well that numerous equivalent conditions may be employed to comprise low stringency conditions; factors such as the length and nature (DNA, RNA, base composition) of the probe and nature of the target (DNA, RNA, base composition, present in solution or immobilized, etc.) and the concentration of the salts and other components (e.g., the presence or absence of formamide, dextran sulfate, polyethylene glycol) are considered and the hybridization solution may be varied to generate conditions of low stringency hybridization different from, but equivalent to, the above listed conditions. In addition, the art knows conditions that promote hybridization under conditions of high stringency (e.g., increasing the temperature of the hybridization and/or wash steps, the use of formamide in the hybridization solution, etc.).

When used in reference to a double-stranded nucleic acid sequence such as a cDNA or genomic clone, the term "substantially homologous" refers to any probe that can hybridize to either or both strands of the double-stranded nucleic acid sequence under conditions of low stringency as described above.

A gene may produce multiple RNA species that are generated by differential splicing of the primary RNA transcript. cDNAs that are splice variants of the same gene (e.g., the splice variants of OFQR represented by SEQ ID NOs: 10, 12, 14, 16, 18, 19, 20, and 21) will contain regions of sequence identity or complete homology (representing the presence of the same exon or portion of the same exon on both cDNAs) and regions of complete non-identity (for example, representing the presence of exon "A" on cDNA 1 wherein cDNA 2 contains exon "B" instead). Because the two cDNAs contain regions of sequence identity they will both hybridize to a probe derived from the entire gene or portions of the gene containing sequences found on both cDNAs; the two splice variants are therefore substantially homologous to such a probe and to each other.

When used in reference to a single-stranded nucleic acid sequence, the term "substantially homologous" refers to any probe that can hybridize (i.e., it is the complement of) the single-stranded nucleic acid sequence under conditions of low stringency as described above.

As used herein, the term "competes for binding" is used in reference to a first polypeptide with an activity which binds to the same substrate as does a second polypeptide with an activity, where the second polypeptide is a variant of the first polypeptide or a related or dissimilar polypeptide. The efficiency (e.g., kinetics or thermodynamics) of binding by the first polypeptide may be the same as or greater than or less than the efficiency substrate binding by the second polypeptide. For example, the equilibrium binding constant ($K_D$) for binding to the substrate may be different for the two polypeptides. The term "$K_M$" as used herein refers to the Michaelis-Menton constant for an enzyme and is defined as the concentration of the specific substrate at which a given enzyme yields one-half its maximum velocity in an enzyme catalyzed reaction.

As used herein, the term "hybridization" is used in reference to the pairing of complementary nucleic acids. Hybridization and the strength of hybridization (i.e., the strength of the association between the nucleic acids) is impacted by such factors as the degree of complementary between the nucleic acids, stringency of the conditions involved, the $T_m$ of the formed hybrid, and the G:C ratio within the nucleic acids.

As used herein, the term "$T_m$" is used in reference to the "melting temperature." The melting temperature is the temperature at which a population of double-stranded nucleic acid molecules becomes half dissociated into single strands. The equation for calculating the $T_m$ of nucleic acids is well known in the art. As indicated by standard references, a simple estimate of the $T_m$ value may be calculated by the equation: $T_m=81.5+0.41(\% \text{ G+C})$, when a nucleic acid is in aqueous solution at 1 M NaCl (See e.g., Anderson and Young, Quantitative Filter Hybridization, in *Nucleic Acid Hybridization* [1985]). Other references include more sophisticated computations that take structural as well as sequence characteristics into account for the calculation of $T_m$.

As used herein the term "stringency" is used in reference to the conditions of temperature, ionic strength, and the presence of other compounds such as organic solvents, under which nucleic acid hybridizations are conducted. Those skilled in the art will recognize that "stringency" conditions may be altered by varying the parameters just described either individually or in concert. With "high stringency" conditions, nucleic acid base pairing will occur only between nucleic acid fragments that have a high frequency of complementary base sequences (e.g., hybridization under "high stringency" conditions may occur between homologs with about 85–100% identity, preferably about 70–100% identity). With medium stringency conditions, nucleic acid base pairing will occur between nucleic acids with an intermediate frequency of complementary base sequences (e.g., hybridization under "medium stringency" conditions may occur between homologs with about 50–70% identity). Thus, conditions of "weak" or "low" stringency are often required with nucleic acids that are derived from organisms that are genetically diverse, as the frequency of complementary sequences is usually less.

"High stringency conditions" when used in reference to nucleic acid hybridization comprise conditions equivalent to binding or hybridization at 42 C in a solution consisting of 5×SSPE (43.8 g/l NaCl, 6.9 g/l NaH$_2$PO$_4$ H$_2$O and 1.85 g/l EDTA, pH adjusted to 7.4 with NaOH), 0.5% SDS, 5×Denhardt's reagent and 100 μg/ml denatured salmon sperm DNA followed by washing in a solution comprising 0.1×SSPE, 1.0% SDS at 42 C when a probe of about 500 nucleotides in length is employed.

"Medium stringency conditions" when used in reference to nucleic acid hybridization comprise conditions equivalent to binding or hybridization at 42 C in a solution consisting of 5×SSPE (43.8 g/l NaCl, 6.9 g/l NaH$_2$PO$_4$ H$_2$O and 1.85 g/l EDTA, pH adjusted to 7.4 with NaOH), 0.5% SDS, 5×Denhardt's reagent and 100 μg/ml denatured salmon sperm DNA followed by washing in a solution comprising 1.0×SSPE, 1.0% SDS at 42 C when a probe of about 500 nucleotides in length is employed.

"Low stringency conditions" comprise conditions equivalent to binding or hybridization at 42 C in a solution consisting of 5×SSPE (43.8 g/l NaCl, 6.9 g/l NaH$_2$PO$_4$ H$_2$O and 1.85 g/l EDTA, pH adjusted to 7.4 with NaOH), 0.1% SDS, 5×Denhardt's reagent [50×Denhardt's contains per 500 ml: 5 g Ficoll (Type 400, Pharamcia), 5 g BSA (Fraction V; Sigma)] and 100 g/ml denatured salmon sperm DNA followed by washing in a solution comprising 5×SSPE, 0.1% SDS at 42 C when a probe of about 500 nucleotides in length is employed.

The following terms are used to describe the sequence relationships between two or more polynucleotides: "reference sequence," "sequence identity," "percentage of sequence identity," and "substantial identity." A "reference sequence" is a defined sequence used as a basis for a sequence comparison; a reference sequence may be a subset of a larger sequence, for example, as a segment of a full-length cDNA sequence given in a sequence listing or may comprise a complete gene sequence. Generally, a reference sequence is at least 20 nucleotides in length, frequently at least 25 nucleotides in length, and often at least 50 nucleotides in length. Since two polynucleotides may each (1) comprise a sequence (i.e., a portion of the complete polynucleotide sequence) that is similar between the two polynucleotides, and (2) may further comprise a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window," as used herein, refers to a conceptual segment of at least 20 contiguous nucleotide positions wherein a polynucleotide sequence may be compared to a reference sequence of at least 20 contiguous nucleotides and wherein the portion of the polynucleotide sequence in the comparison window may comprise additions or deletions (i.e., gaps) of 20 percent or less as compared to the reference sequence (which does not comprise additions or deletions) for optimal alignment of the two sequences. Optimal alignment of sequences for aligning a comparison window may be conducted by the local homology algorithm of Smith and Waterman [Smith and Waterman, *Adv. Appl. Math.* 2: 482 (1981)] by the homology alignment algorithm of Needleman and Wunsch [Needleman and Wunsch, *J. Mol. Biol.* 48 443 (1970)], by the search for similarity method of Pearson and Lipman [Pearson and Lipman, *Proc. Nail. Acad. Sci. (U.S.A.)* 85:2444 (1988)], by computerized implementations of these algorithms (GAP, BESTFIT, FASTA, and TFASTA in the Wisconsin Genetics Software Package Release 7.0, Genetics Computer Group, 575 Science Dr., Madison, Wis.), or by inspection, and the best alignment (i.e., resulting in the highest percentage of homology over the comparison window) generated by the various methods is selected. The term "sequence identity" means that two polynucleotide sequences are identical (i.e., on a nucleotide-by-nucleotide basis) over the window of comparison. The term "percentage of sequence identity" is calculated by comparing two optimally aligned sequences over the window of comparison, determining the number of positions at which the identical nucleic acid base (e.g., A, T, C, G, U, or 1) occurs in both sequences to yield the number of matched positions, dividing the number of matched positions by the total number of positions in the window of comparison (i.e., the window size), and multiplying the result by 100 to yield the percentage of sequence identity.

As applied to polynucleotides, the term "substantial identity" denotes a characteristic of a polynucleotide sequence, wherein the polynucleotide comprises a sequence that has at least 85 percent sequence identity, preferably at least 90 to 95 percent sequence identity, more usually at least 99 percent sequence identity as compared to a reference sequence over a comparison window of at least 20 nucleotide positions, frequently over a window of at least 25–50 nucleotides, wherein the percentage of sequence identity is calculated by comparing the reference sequence to the polynucleotide sequence which may include deletions or additions which total 20 percent or less of the reference sequence over the window of comparison. The reference sequence may be a subset of a larger sequence, for example, as a splice variant of the full-length sequences of the compositions claimed in the present invention (e.g., OFQR).

As applied to polypeptides, the term "substantial identity" means that two peptide sequences, when optimally aligned, such as by the programs GAP or BESTFIT using default gap weights, share at least 80 percent sequence identity, preferably at least 90 percent sequence identity, more preferably at least 95 percent sequence identity or more (e.g., 99 percent sequence identity). Preferably, residue positions that are not identical differ by conservative amino acid substitutions. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, and asparagine-glutamine.

"Amplification" is a special case of nucleic acid replication involving template specificity. It is to be contrasted with non-specific template replication (i.e., replication that is template-dependent but not dependent on a specific template). Template specificity is here distinguished from fidelity of replication (i.e., synthesis of the proper polynucleotide sequence) and nucleotide (ribo- or deoxyribo-) specificity. Template specificity is frequently described in terms of "target" specificity. Target sequences are "targets" in the sense that they are sought to be sorted out from other nucleic acid. Amplification techniques have been designed primarily for this sorting out.

Template specificity is achieved in most amplification techniques by the choice of enzyme. Amplification enzymes are enzymes that, under conditions they are used, will process only specific sequences of nucleic acid in a heterogeneous mixture of nucleic acid. For example, in the case of Q replicase, MDV-1 RNA is the specific template for the replicase (D. L. Kacian et al., Proc. Natl. Acad. Sci. USA 69:3038 [1972]). Other nucleic acid will not be replicated by this amplification enzyme. Similarly, in the case of T7 RNA polymerase, this amplification enzyme has a stringent specificity for its own promoters (M. Chamberlin et al., Nature 228:227 [1970]). In the case of T4 DNA ligase, the enzyme will not ligate the two oligonucleotides or polynucleotides, where there is a mismatch between the oligonucleotide or polynucleotide substrate and the template at the ligation junction (D. Y. Wu and R. B. Wallace, Genomics 4:560 [989]). Finally, Taq and Pfu polymerases, by virtue of their ability to function at high temperature, are found to display high specificity for the sequences bounded and thus defined by the primers; the high temperature results in thermodynamic conditions that favor primer hybridization with the target sequences and not hybridization with non-target sequences (H. A. Erlich (ed.), *PCR Technology*, Stockton Press [1989]).

As used herein, the term "amplifiable nucleic acid" is used in reference to nucleic acids that may be amplified by any amplification method. It is contemplated that "amplifiable nucleic acid" will usually comprise "sample template."

As used herein, the term "sample template" refers to nucleic acid originating from a sample that is analyzed for the presence of "target" (defined below). In contrast, "background template" is used in reference to nucleic acid other than sample template that may or may not be present in a sample. Background template is most often inadvertent. It may be the result of carryover, or it may be due to the presence of nucleic acid contaminants sought to be purified away from the sample. For example, nucleic acids from organisms other than those to be detected may be present as background in a test sample.

As used herein, the term "primer" refers to an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced, (i.e., in the presence of nucleotides and an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer and the use of the method.

As used herein, the term "probe" refers to an oligonucleotide (i.e., a sequence of nucleotides), whether occurring naturally as in a purified restriction digest or produced synthetically, recombinantly or by PCR amplification, that is capable of hybridizing to another oligonucleotide of interest. A probe may be single-stranded or double-stranded. Probes are useful in the detection, identification and isolation of particular gene sequences. It is contemplated that any probe used in the present invention will be labeled with any "reporter molecule," so that is detectable in any detection system, including, but not limited to enzyme (e.g., ELISA, as well as enzyme-based histochemical assays), fluorescent, radioactive, and luminescent systems. It is not intended that the present invention be limited to any particular detection system or label.

As used herein, the term "target," when used in reference to the polymerase chain reaction, refers to the region of nucleic acid bounded by the primers used for polymerase chain reaction. Thus, the "target" is sought to be sorted out from other nucleic acid sequences. A "segment" is defined as a region of nucleic acid within the target sequence.

As used herein, the term "polymerase chain reaction" ("PCR") refers to the method of K. B. Mullis (See e.g., U.S. Pat. Nos. 4,683,195, 4,683,202, and 4,965,188, hereby incorporated by reference), which describe a method for increasing the concentration of a segment of a target sequence in a mixture of genomic DNA without cloning or purification. This process for amplifying the target sequence consists of introducing a large excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers then annealed to their complementary sequences within the target molecule. Following annealing, the primers are extended with a polymerase so as to form a new pair of complementary strands. The steps of denaturation, primer annealing, and polymerase extension can be repeated many times (i.e., denaturation, annealing and extension constitute one "cycle"; there can be numerous "cycles") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to as the "polymerase chain reaction" (hereinafter "PCR"). Because the desired amplified segments of the target sequence become the predominant sequences (in terms of concentration) in the mixture, they are said to be "PCR amplified."

With PCR, it is possible to amplify a single copy of a specific target sequence in genomic DNA to a level detectable by several different methodologies (e.g. hybridization with a labeled probe; incorporation of biotinylated primers followed by avidin-enzyme conjugate detection; incorporation of $^{32}$P-labeled deoxynucleotide triphosphates, such as dCTP or dATP, into the amplified segment). In addition to genomic DNA, any oligonucleotide or polynucleotide sequence can be amplified with the appropriate set of primer molecules. In particular, the amplified segments created by the PCR process itself are, themselves, efficient templates for subsequent PCR amplifications.

As used herein, the terms "PCR product," "PCR fragment," and "amplification product" refer to the resultant mixture of compounds after two or more cycles of the PCR steps of denaturation, annealing and extension are complete. These terms encompass the case where there has been amplification of one or more segments of one or more target sequences.

As used herein, the term "amplification reagents" refers to those reagents (deoxyribonucleotide triphosphates, buffer, etc.), needed for amplification except for primers, nucleic acid template, and the amplification enzyme. Typically, amplification reagents along with other reaction components are placed and contained in a reaction vessel (test tube, microwell, etc.).

As used herein, the term "recombinant DNA molecule" as used herein refers to a DNA molecule that is comprised of segments of DNA joined together by means of molecular biological techniques.

As used herein, the term "antisense" is used in reference to RNA sequences that are complementary to a specific RNA sequence (e.g., mRNA). The term "antisense strand" is used in reference to a nucleic acid strand that is complementary to the "sense" strand. The designation (−) (i.e., "negative") is sometimes used in reference to the antisense strand, with the designation (+) sometimes used in reference to the sense (i.e., "positive") strand.

The term "isolated" when used in relation to a nucleic acid, as in "an isolated oligonucleotide" or "isolated polynucleotide" refers to a nucleic acid sequence that is identified and separated from at least one contaminant nucleic acid with which it is ordinarily associated in its natural source. Isolated nucleic acid is present in a form or setting that is different from that in which it is found in nature. In contrast, non-isolated nucleic acids are nucleic acids such as DNA and RNA found in the state they exist in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs that encode a multitude of proteins. However, isolated nucleic acids encoding OFQR include, by way of example, such nucleic acid in cells ordinarily expressing OFQR where the nucleic acid is in a chromosomal location different from that of natural cells, or is otherwise flanked by a different nucleic acid sequence than that found in nature. The isolated nucleic acid, oligonucleotide, or polynucleotide may be present in single-stranded or double-stranded form. When an isolated nucleic acid, oligonucleotide or polynucleotide is to be utilized to express a protein, the oligonucleotide or polynucleotide will contain at a minimum the sense or coding strand (i.e., the oligonucleotide or polynucleotide may single-stranded), but may contain both the sense and anti-sense strands (i.e., the oligonucleotide or polynucleotide may be double-stranded).

As used herein the term "portion" when in reference to a nucleotide sequence (as in "a portion of a given nucleotide sequence") refers to fragments of that sequence. The fragments may range in size from four nucleotides to the entire nucleotide sequence minus one nucleotide (10 nucleotides, 20, 30, 40, 50, 100, 200, etc.).

As used herein the term "coding region" when used in reference to structural gene refers to the nucleotide sequences that encode the amino acids found in the nascent polypeptide as a result of translation of a mRNA molecule. The coding region is bounded, in eukaryotes, on the 5' side by the nucleotide triplet "ATG" that encodes the initiator methionine and on the 3' side by one of the three triplets that specify stop codons (i.e., TAA, TAG, TGA).

As used herein, the term "purified" or "to purify" refers to the removal of contaminants from a sample. For example, OFQR antibodies are purified by removal of contaminating non-immunoglobulin proteins; they are also purified by the removal of immunoglobulin that does not bind OFQR or specific splice variants of OFQR. The removal of non-immunoglobulin proteins and/or the removal of immunoglobulins that do not bind OFQR or splice variants thereof results in an increase in the percent of OFQR-reactive immunoglobulins in the sample.

The term "recombinant protein" or "recombinant polypeptide" as used herein refers to a protein molecule that is expressed from a recombinant DNA molecule.

The term "native protein" as used herein to indicate that a protein does not contain amino acid residues encoded by vector sequences; that is the native protein contains only those amino acids found in the protein as it occurs in nature. A native protein may be produced by recombinant means or may be isolated from a naturally occurring source.

As used herein the term "portion" when in reference to a protein (as in "a portion of a given protein") refers to fragments of that protein. The fragments may range in size from four consecutive amino acid residues to the entire amino acid sequence minus one amino acid.

The term "Southern blot," refers to the analysis of DNA on agarose or acrylamide gels to fractionate the DNA according to size followed by transfer of the DNA from the gel to a solid support, such as nitrocellulose or a nylon membrane. The immobilized DNA is then probed with a labeled probe to detect DNA species complementary to the probe used. The DNA may be cleaved with restriction enzymes prior to electrophoresis. Following electrophoresis, the DNA may be partially depurinated and denatured prior to or during transfer to the solid support. Southern blots are a standard tool of molecular biologists (J. Sambrook et al., *Molecular Cloning: A Laboratory Manual*, Cold Spring Harbor Press, NY, pp 9.31–9.58 [1989]).

The term "Western blot" refers to the analysis of protein(s) (or polypeptides) immobilized onto a support such as nitrocellulose or a membrane. The proteins are run on acrylamide gels to separate the proteins, followed by transfer of the protein from the gel to a solid support, such as nitrocellulose or a nylon membrane. The immobilized proteins are then exposed to antibodies with reactivity against an antigen of interest. The binding of the antibodies may be detected by various methods, including the use of labeled antibodies.

The term "antigenic determinant" as used herein refers to that portion of an antigen that makes contact with a particular antibody (i.e., an epitope). When a protein or fragment of a protein is used to immunize a host animal, numerous regions of the protein may induce the production of antibodies that bind specifically to a given region or three-dimensional structure on the protein; these regions or structures are referred to as antigenic determinants. An antigenic determinant may compete with the intact antigen (i.e., the "immunogen" used to elicit the immune response) for binding to an antibody.

The term "transgene" as used herein refers to a foreign gene that is placed into an organism by introducing the foreign gene into newly fertilized eggs or early embryos. The term "foreign gene" refers to any nucleic acid (e.g., gene sequence) that is introduced into the genome of an animal by experimental manipulations and may include gene sequences found in that animal so long as the introduced gene does not reside in the same location as does the naturally-occurring gene.

As used herein, the term "vector" is used in reference to nucleic acid molecules that transfer DNA segment(s) from one cell to another. The term "vehicle" is sometimes used interchangeably with "vector."

The term "expression vector" as used herein refers to a recombinant DNA molecule containing a desired coding sequence and appropriate nucleic acid sequences necessary for the expression of the operably linked coding sequence in a particular host organism. Nucleic acid sequences necessary for expression in prokaryotes usually include a promoter, an operator (optional), and a ribosome binding site, often along with other sequences. Eukaryotic cells are known to utilize promoters, enhancers, and termination and polyadenylation signals.

As used herein, the term host cell refers to any eukaryotic or prokaryotic cell (e.g., bacterial cells such as $E.$ $coli$, yeast cells, mammalian cells, avian cells, amphibian cells, plant cells, fish cells, and insect cells), whether located in vitro or in vivo. For example, host cells may be located in a transgenic animal.

The terms "overexpression" and "overexpressing" and grammatical equivalents, are used in reference to levels of mRNA to indicate a level of expression approximately 3-fold higher than that typically observed in a given tissue in a control or non-transgenic animal. Levels of mRNA are measured using any of a number of techniques known to those skilled in the art including, but not limited to Northern blot analysis. Appropriate controls are included on the Northern blot to control for differences in the amount of RNA loaded from each tissue analyzed (e.g., the amount of 28S rRNA, an abundant RNA transcript present at essentially the same amount in all tissues, present in each sample can be used as a means of normalizing or standardizing the RAD50 mRNA-specific signal observed on Northern blots). The amount of mRNA present in the band corresponding in size to the RNA of interest (e.g., OFQR splice variants) is quantified; other minor species of RNA that hybridize to the probe are not considered in the quantification of the expression of the transgenic mRNA.

The term "transfection" as used herein refers to the introduction of foreign DNA into eukaryotic cells. Transfection may be accomplished by a variety of means known to the art including calcium phosphate-DNA co-precipitation, DEAE-dextran-mediated transfection, polybrene-mediated transfection, electroporation, microinjection, liposome fusion, lipofection, protoplast fusion, retroviral infection, and biolistics.

The term "stable transfection" or "stably transfected" refers to the introduction and integration of foreign DNA into the genome of the transfected cell. The term "stable transfectant" refers to a cell that has stably integrated foreign DNA into the genomic DNA.

The term "transient transfection" or "transiently transfected" refers to the introduction of foreign DNA into a cell where the foreign DNA fails to integrate into the genome of the transfected cell. The foreign DNA persists in the nucleus of the transfected cell for several days. During this time the foreign DNA is subject to the regulatory controls that govern the expression of endogenous genes in the chromosomes. The term "transient transfectant" refers to cells that have taken up foreign DNA but have failed to integrate this DNA.

The term "calcium phosphate co-precipitation" refers to a technique for the introduction of nucleic acids into a cell. The uptake of nucleic acids by cells is enhanced when the nucleic acid is presented as a calcium phosphate-nucleic acid co-precipitate. The original technique of Graham and van der Eb (Graham and van der Eb, Virol., 52:456 [1973]), has been modified by several groups to optimize conditions for particular types of cells. The art is well aware of these numerous modifications.

The term "test compound" refers to any chemical entity, pharmaceutical, drug, and the like that are tested in an assay (e.g., a drug screening assay) for any desired activity (e.g., including but not limited to, the ability to treat or prevent a disease, illness, sickness, or disorder of bodily function, or otherwise alter the physiological or cellular status of a sample). Test compounds comprise both known and potential therapeutic compounds. A test compound can be determined to be therapeutic by screening using the screening methods of the present invention. A "known therapeutic compound" refers to a therapeutic compound that has been shown (e.g., through animal trials or prior experience with administration to humans) to be effective in such treatment or prevention.

The term "sample" as used herein is used in its broadest sense. A sample suspected of containing a human chromosome or sequences associated with a human chromosome may comprise a cell, chromosomes isolated from a cell (e.g., a spread of metaphase chromosomes), genomic DNA (in solution or bound to a solid support such as for Southern blot analysis), RNA (in solution or bound to a solid support such as for Northern blot analysis), cDNA (in solution or bound to a solid support) and the like. A sample suspected of containing a protein may comprise a cell, a portion of a tissue, an extract containing one or more proteins and the like.

As used herein, the term "response," when used in reference to an assay, refers to the generation of a detectable signal (e.g., accumulation of reporter protein, increase in ion concentration, accumulation of a detectable chemical product).

As used herein, the term "reporter gene" refers to a gene encoding a protein that may be assayed. Examples of reporter genes include, but are not limited to, luciferase (See, e.g., deWet et al., Mol. Cell. Biol. 7:725 [1987] and U.S. Pat Nos. 6,074,859; 5,976,796; 5,674,713; and 5,618,682; all of which are incorporated herein by reference), green fluorescent protein (e.g., GenBank Accession Number U43284; a number of GFP variants are commercially available from CLONTECH Laboratories, Palo Alto, Calif.), chloramphenicol acetyltransferase, -galactosidase, alkaline phosphatase, and horse radish peroxidase.

As used herein, the term "purified" refers to molecules, either nucleic or amino acid sequences, which are removed from their natural environment, isolated or separated. An "isolated nucleic acid sequence" is therefore a purified nucleic acid sequence. "Substantially purified" molecules are at least 60% free, preferably at least 75% free, and more preferably at least 90% free from other components with which they are naturally associated.

DETAILED DESCRIPTION OF THE INVENTION

The present invention provides OFQR nucleic acids. In some embodiments, the present invention provides nucleic acids (e.g., mRNA) encoding novel splice variants of OFQR. In some embodiments, the present invention provides methods of utilizing the splice variants for the development of specific receptor agonists and antagonists. In still further embodiments, the present invention provides transgenic animals useful as animal models of disease states involving altered OFQR receptors as well as providing system for the study of complex neurological responses.

I. OFQR Nucleic Acids

In some embodiments, the present invention comprises OFQR nucleic acids. The present invention is not limited to any one particular OFQR nucleic acid. In some embodiments, the present invention comprises genomic (e.g., DNA sequences) encoding an OFQR. In other embodiments, the present invention comprises expressed (e.g., mRNA) sequences encoding spliced OFQR encoding sequences. In still further embodiments, the present invention comprises mutants, variants, homologs, and orthologs of the disclosed sequences.

A. Isolation and Characterization of Rat OFQR

Figure 2:
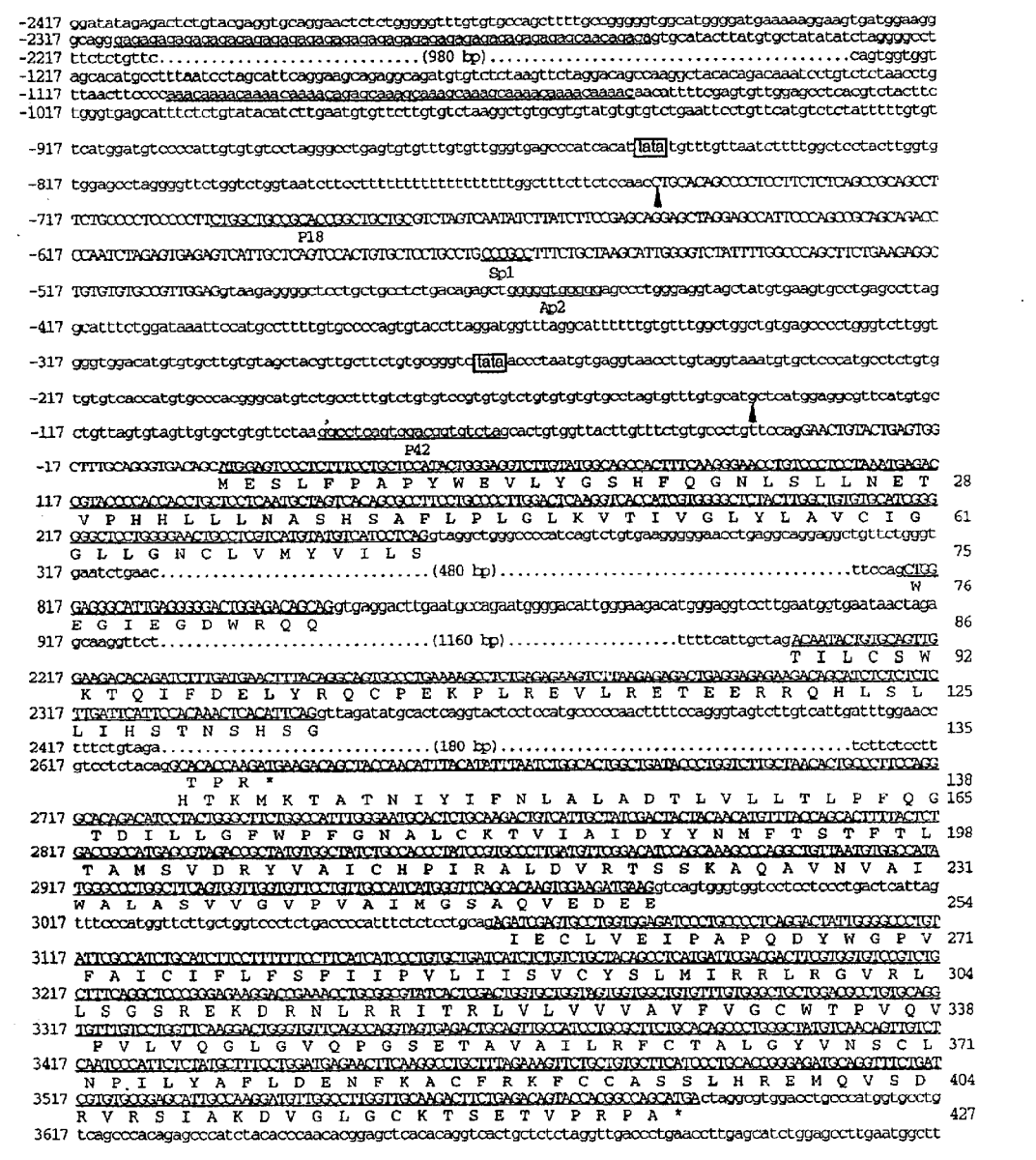

In some embodiments, the present invention provides rat OFQR nucleic acid sequences. For example, the present invention provides the rat OFQR nucleic acid sequence of SEQ ID NO:9. Examples 1 and 2 describe the isolation and characterization of the rat OFQR gene. The rat OFQR gene exceeds 10 kb in length and contains six exons that are interrupted by five introns (FIG. 2). Two major transcription initiation sites were identified: one in the 5' flanking region and the other in intron 1.

In other embodiments, the present invention provides mRNA splice variants of the rat OFQR gene (e.g., SEQ ID NOs: 10,12,14,16,18,19,20, and 21). Primer extension analysis was used to identify splice variants of the OFQR gene (See Examples 2 and 3). The OFQR gene was found to be alternatively spliced to yield multiple RNAs. Splice variants were PCR cloned and sequenced (Example 3). The sequencing results revealed that rat OFQR expressed at least nine splice variants deleted for exon 1, or exons 3 to 5 (See FIG. 5C).

Figure 5:
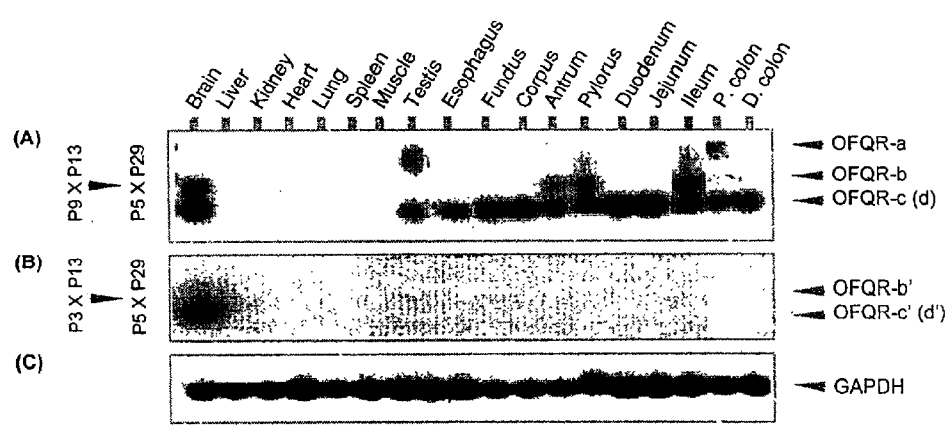

As described above, the varying effects of Orphanin FQ in different tissues suggested that multiple OFQR subtypes existed in different tissues. Example 4 describes the detection of differential tissue expression of the splice variants. As shown in FIG. 5A, PCR products of OFQR variants were not detected in liver, kidney, heart, lung, spleen, or skeletal muscle. Two forms were expressed in testes. These forms, in addition to one additional variant, were expressed in pylorus, ileum, and proximal colon. Both forms, OFQR-b and -c (or -d) were expressed in brain and antin. OFQR-c (or -d) was expressed in esophagus, fundus, corpus, duodenum, jejunum, and descending colon. As shown in FIG. 5B, the OFQR-c' or -d' splice variants were expressed only in brain. These data suggest that unique regions in the 5' flanking region and in intron 1 of the OFQR gene contribute to the regulation of its expression in different as tissues.

B. Variants of OFQR

In other embodiments of the present invention, variants of the disclosed OFQR sequences are provided. In preferred embodiments, variants result from mutation, (i.e., a change in the nucleic acid sequence) and generally produce altered mRNAs or polypeptides whose structure or function may or may not be altered. Any given gene may have none, one, or many variant forms. Common mutational changes that give rise to variants are generally ascribed to deletions, additions or substitutions of nucleic acids. Each of these types of changes may occur alone, or in combination with the others, and at the rate of one or more times in a given sequence.

It is contemplated that it is possible to modify the structure of a polypeptide having a function (e.g., OFQR) for such purposes as increasing of decreased binding affinity of the OFQR for a ligand (e.g., Orphanin FQ). Such modified peptides are considered functional equivalents of peptides having an activity of OFQR as defined herein. A modified peptide can be produced in which the nucleotide sequence encoding the polypeptide has been altered, such as by substitution, deletion, or addition. In other words, construct "X" can be evaluated in order to determine whether it is a member of the genus of modified or variant OFQRs of the present invention as defined functionally, rather than structurally. In preferred embodiments, the activity of variant or mutant OFQR (e.g., ligand binding) is evaluated by a previously described method (See e.g., Meng et al., Mol. Pharmacol. 53:772 [1998]; Wnendt et al., Mol. Pharmacol. 56:334 [1999]). Accordingly, in some embodiments, the present invention provides nucleic acids encoding an OFQR polypeptide that binds Orphanin FQ.

In some embodiments, OFQR nucleic acid sequences are modified to contain portion of the human OFQR cDNA sequence (Gen Bank Accession Number NM_000913.1; SEQ ID NO:22). In some embodiments, domains (e.g., those corresponding to Exons 1, 2, 3, 4 5, or 6 of the rat nucleic acid) are substituted with the corresponding human domains. Suitable domains of the human nucleic acid can be identified by aligning nucleic acid sequences from various species in order to determine the conserved regions or domains. Any suitable software may be used for sequence alignment, including but not limited to, those disclosed herein.

Moreover, as described above, variant forms of OFQR are also contemplated as being equivalent to those peptides and DNA molecules that are set forth in more detail herein. For example, it is contemplated that isolated replacement of a leucine with an isoleucine or valine, an aspartate with a glutamate, a threonine with a serine, or a similar replacement of an amino acid with a structurally related amino acid (i.e., conservative mutations) will not have a major effect on the biological activity of the resulting molecule. Accordingly, some embodiments of the present invention provide variants of OFQR disclosed herein containing conservative replacements. Conservative replacements are those that take place within a family of amino acids that are related in their side chains. Genetically encoded amino acids can be divided into four families: (1) acidic (aspartate, glutamate); (2) basic (lysine, arginine, histidine); (3) nonpolar (alanine, valine, leucine, isoleucine, proline, phenylalanine, methionine, tryptophan); and (4) uncharged polar (glycine, asparagine, glutamine, cysteine, serine, threonine, tyrosine). Phenylalanine, tryptophan, and tyrosine are sometimes classified jointly as aromatic amino acids. In similar fashion, the amino acid repertoire can be grouped as (1) acidic (aspartate, glutamate); (2) basic (lysine, arginine, histidine), (3) aliphatic (glycine, alanine, valine, leucine, isoleucine, serine, threonine), with serine and threonine optionally be grouped separately as aliphatic-hydroxyl; (4) aromatic (phenylalanine, tyrosine, tryptophan); (5) amide (asparagine, glutamine); and (6) sulfur -containing (cysteine and methionine) (e.g., Stryer ed., *Biochemistry*, pg. 17–21, 2nd ed, WH Freeman and Co., 1981). Whether a change in the amino acid sequence of a peptide results in a functional homolog can be readily determined by assessing the ability of the variant peptide to fiction in a fashion similar to the wild-type protein. Peptides having more than one replacement can readily be tested in the same manner.

More rarely, a variant includes "nonconservative" changes (e.g., replacement of a glycine with a tryptophan). Analogous minor variations can also include amino acid deletions or insertions, or both. Guidance in determining which amino acid residues can be substituted, inserted, or deleted without abolishing biological activity can be found using computer programs (e.g., LASERGENE software, DNASTAR Inc., Madison, Wis.).

As described in more detail below, variants may be produced by methods such as directed evolution or other techniques for producing combinatorial libraries of variants, described in more detail below. In still other embodiments of the present invention, the nucleotide sequences of the present invention may be engineered in order to alter a OFQR coding sequence including, but not limited to, alterations that modify the cloning, processing, localization, secretion, and/or expression of the gene product. For example, mutations may be introduced using techniques that are well known in the art (e.g., site-directed mutagenesis to insert new restriction sites, alter glycosylation patterns, or change codon preference, etc.).

II. OFQR Polypeptides

In some embodiments, the present invention provides OFQR polynucleotide sequences that encode OFQR polypeptide sequences. OFQR polypeptides (e.g., SEQ ID NOs:11,13,15,17 and 23) are described in FIGS. 2, 8, 10, 12, 14, and 20. Other embodiments of the present invention provide fragments, fusion proteins or functional equivalents of these OFQR proteins. In still other embodiment of the present invention, nucleic acid sequences corresponding to these various OFQR homologs and mutants may be used to generate recombinant DNA molecules that direct the expression of the OFQR homologs and mutants in appropriate host cells. In some embodiments of the present invention, the polypeptide may be a naturally purified product, in other embodiments it may be a product of chemical synthetic procedures, and in still other embodiments it may be produced by recombinant techniques using a prokaryotic or eukaryotic host cells (e.g., by bacterial, yeast, higher plant, insect and mammalian cells in culture). In some embodiments, depending upon the host employed in a recombinant production procedure, the polypeptide of the present invention may be glycosylated or may be non-glycosylated. In other embodiments, the polypeptides of the invention may also include an initial methionine amino acid residue.

In one embodiment of the present invention, due to the inherent degeneracy of the genetic code, DNA sequences other than the polynucleotide sequences of SEQ ID NOs: 9, 10, 12, 14, 16, 18, 19, 20 and 21 which encode substantially the same or a functionally equivalent amino acid sequence, may be used to clone and express OFQR variants. In general, such polynucleotide sequences hybridize to SEQ ID NO: 9, 10, 12, 14, 16, 18, 19, 20 and 21 under conditions of high to medium stringency as described above. As will be understood by those of skill in the art, it may be advantageous to produce OFQR-encoding nucleotide sequences possessing non-naturally occurring codons. Therefore, in some preferred embodiments, codons preferred by a particular prokaryotic or eukaryotic host (Murray et al., Nucl. Acids Res., 17 [1989]) are selected, for example, to increase the rate of OFQR expression or to produce recombinant RNA transcripts having desirable properties, such as a longer half-life, than transcripts produced from naturally occurring sequences.

A. Vectors for Production of OFQR

The polynucleotides of the present invention may be employed for producing polypeptides by recombinant techniques. Thus, for example, the polynucleotide may be included in any one of a variety of expression vectors for expressing a polypeptide. In some embodiments of the present invention, vectors include, but are not limited to, chromosomal, nonchromosomal and synthetic DNA sequences (e.g., derivatives of SV40, bacterial plasmids, phage DNA; baculovirus, yeast plasmids, vectors derived from combinations of plasmids and phage DNA, and viral DNA such as vaccinia, adenovirus, fowl pox virus, and pseudorabies). It is contemplated that any vector may be used as long as it is replicable and viable in the host.

In particular, some embodiments of the present invention provide recombinant constructs comprising one or more of the sequences as broadly described above (e.g., SEQ ID NO: 9, 10, 12, 14, 16, 18, 19, 20 and 21). In some embodiments of the present invention, the constructs comprise a vector, such as a plasmid or viral vector, into which a sequence of the invention has been inserted, in a forward or reverse orientation. In still other embodiments, the heterologous structural sequence (e.g., SEQ ID NOs: 9, 10, 12, 14, 16, 18, 19, 20 and 21) is assembled in appropriate phase with translation initiation and termination sequences. In preferred embodiments of the present invention, the appropriate DNA sequence is inserted into the vector using any of a variety of procedures. In general, the DNA sequence is inserted into an appropriate restriction endonuclease site(s) by procedures known in the art.

Large numbers of suitable vectors are known to those of skill in the art, and are commercially available. Such vectors include, but are not limited to, the following vectors: 1) Bacterial—pQE70, pQE60, pQE-9 (Qiagen), pBS, pD10, phagescript, psiX174, pbluescript SK, pBSKS, pNH8A, pNH16a, pNH18A, pNH46A (Stratagene); ptrc99a, pKK223-3, pKK233-3, pDR540, pRIT5 (Pharmacia); and 2) Eukaryotic—pWLNEO, pSV2CAT, pOG44, PXT1, pSG (Stratagene) pSVK3, pBPV, pMSG, pSVL (Pharmacia). Any other plasmid or vector may be used as long as they are replicable and viable in the host. In some preferred embodiments of the present invention, mammalian expression vectors comprise an origin of replication, a suitable promoter and enhancer, and also any necessary ribosome binding sites, polyadenylation sites, splice donor and acceptor sites, transcriptional termination sequences, and 5' flanking non-transcribed sequences. In other embodiments, DNA sequences derived from the SV40 splice, and polyadenylation sites may be used to provide the required non-transcribed genetic elements.

In certain embodiments of the present invention, the DNA sequence in the expression vector is operatively linked to an appropriate expression control sequence(s) (promoter) to direct mRNA synthesis. Promoters useful in the present invention include, but are not limited to, the LTR or SV40 promoter, the *E. coli* lac or trp, the phage lambda $P_L$ and $P_R$, T3 and T7 promoters, and the cytomegalovirus (CMV) immediate early, herpes simplex virus (HSV) thymidine kinase, and mouse metallothionein-I promoters and other promoters known to control expression of gene in prokaryotic or eukaryotic cells or their viruses. In other embodiments of the present invention, recombinant expression vectors include origins of replication and selectable markers permitting transformation of the host cell (e.g., dihydrofolate reductase or neomycin resistance for eukaryotic cell culture, or tetracycline or ampicillin resistance in *E. coli*).

In some embodiments of the present invention, transcription of the DNA encoding one of the polypeptides of the present invention by higher eukaryotes is increased by inserting an enhancer sequence into the vector. Enhancers are cis-acting elements of DNA, usually about from 10 to 300 bp that act on a promoter to increase its transcription. Enhancers useful in the present invention include, but are not limited to, the SV40 enhancer on the late side of the replication origin bp 100 to 270, a cytomegalovirus early promoter enhancer, the polyoma enhancer on the late side of the replication origin, and adenovirus enhancers.

In other embodiments, the expression vector also contains a ribosome binding site for translation initiation and a transcription terminator. In still other embodiments of the present invention, the vector may also include appropriate sequences for amplifying expression.

B. Host Cells for Production of OFQR

In a further embodiment, the present invention provides host cells containing the above-described constructs. In some embodiments of the present invention, the host cell is a higher eukaryotic cell (e.g., a mammalian or insect cell). In other embodiments of the present invention, the host cell is a lower eukaryotic cell (e.g., a yeast cell). In still other embodiments of the present invention, the host cell can be a prokaryotic cell (e.g., a bacterial cell). Specific examples of host cells include, but are not limited to, *Escherichia coli*, *Salmonella typhimurium, Bacillus subtilis*, and various species within the genera *Pseudomonas, Streptomyces*, and *Staphylococcus*, as well as *Saccharomyces cerivisiae, Schizosaccharomycees pombe, Drosophila* S2 cells, *Spodopiera* Sf9 cells, Chinese hamster ovary (CHO) cells, COS-7 lines of monkey kidney fibroblasts, (Gluzman, Cell 23:175 [1981]), C127, 3T3, 293, 293T, HeLa and BHK cell lines.

The constructs in host cells can be used in a conventional manner to produce the gene product encoded by the recombinant sequence. In some embodiments, introduction of the construct into the host cell can be accomplished by calcium phosphate transfection, DEAE-Dextran mediated transfection, or electroporation (See e.g., Davis et al., Basic Methods in Molecular Biology, [1986]). Alternatively, in some embodiments of the present invention, the polypeptides of the invention can be synthetically produced by conventional peptide synthesizers.

Proteins can be expressed in mammalian cells, yeast, bacteria, or other cells under the control of appropriate promoters. Cell-free translation systems can also be employed to produce such proteins using RNAs (e.g., splice variants of OFQR) derived from the DNA constructs of the present invention. Appropriate cloning and expression vectors for use with prokaryotic and eukaryotic hosts are described by Sambrook, et al., Molecular Cloning: A Laboratory Manual, Second Edition, Cold Spring Harbor, N.Y., (1989).

In some embodiments of the present invention, following transformation of a suitable host strain and growth of the host strain to an appropriate cell density, the selected promoter is as induced by appropriate means (e.g., temperature shift or chemical induction) and cells are cultured for an additional period.

C. Fusion Proteins Containing OFQR

The present invention also provides fusion proteins incorporating all or part of an OFQR polypeptide. Accordingly, in some embodiments of the present invention, a coding sequence for one of the polypeptides of the present invention can be incorporated as a part of a fusion gene including a nucleotide sequence encoding a different polypeptide. It is contemplated that this type of expression system will find use under conditions where it is desirable to produce an immunogenic fragment of an OFQR polypeptide. In some embodiments of the present invention, the VP6 capsid protein of rotavirus is used as an immunologic carrier protein for portions of a OFQR polypeptide of the present invention (e.g., SEQ ID Nos: 11, 13, 15,17 and 23), either in the monomeric form or in the form of a viral particle. In other embodiments of the present invention, the nucleic acid sequences corresponding to the portion of OFQR against which antibodies are to be raised can be incorporated into a fusion gene construct which includes coding sequences for a late vaccinia virus structural protein to produce a set of recombinant viruses expressing fusion proteins comprising a portion of OFQR as part of the virion. It has been demonstrated with the use of immunogenic fusion proteins utilizing the hepatitis B surface antigen fusion proteins that recombinant hepatitis B virions can be utilized in this role as well. Similarly, in other embodiments of the present invention, chimeric constructs coding for fusion proteins containing a portion of OFQR and the poliovirus capsid protein are created to enhance immunogenicity of the set of polypeptide antigens (See e.g., EP Publication No. 025949; and Evans et al., Nature 339:385 [1989]; Huang et al., J. Virol., 62:3855 [1988]; and Schlienger et al., J. Virol., 66:2 [1992]).

In still other embodiments of the present invention, the multiple antigen peptide system for peptide-based immunization can be utilized. In this system, a desired portion of OFQR is obtained directly from organo-chemical synthesis of the peptide onto an oligomeric branching lysine core (see e.g., Posnett et al., J. Biol. Chem., 263:1719 [1988]; and Nardelli et al., J. Immunol., 148:914 [1992]). In other embodiments of the present invention, antigenic determinants of the OFQR proteins can also be expressed and presented by bacterial cells.

Techniques for making fusion genes are well known. Essentially, the joining of various DNA fragments coding for different polypeptide sequences is performed in accordance with conventional techniques, employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment of the present invention, the fusion gene can be synthesized by conventional techniques including automated DNA synthesizers. Alternatively, in other embodiments of the present invention, PCR amplification of gene fragments can be carried out using anchor primers which give rise to complementary overhangs between two consecutive gene fragments which can subsequently be annealed to generate a chimeric gene sequence (See e.g., Current Protocols in Molecular Biology, supra).

D. Variants of OFQR

Still other embodiments of the present invention provide mutant or variant forms of OFQR (i.e., muteins). It is possible to modify the structure of a polypeptide having an activity of OFQR for such purposes as enhancing therapeutic or prophylactic efficacy, or stability (e.g., ex vivo shelf life, and/or resistance to proteolytic degradation in vivo). Such modified polypeptides are considered functional equivalents of polypeptides having an activity of the subject OFQR proteins as defined herein. A modified polypeptide can be produced in which the amino acid sequence has been altered, such as by amino acid substitution, deletion, or addition.

Moreover, as described above, variant forms (e.g., mutants) of the subject OFQR proteins are also contemplated as being equivalent to those peptides and DNA molecules that are set forth in more detail. For example, as described above, the present invention encompasses mutant and variant proteins that contain conservative or non-conservative amino acid substitutions.

This invention further contemplates a method of generating sets of combinatorial mutants of the present OFQR proteins, as well as truncation mutants, and is especially useful for identifying potential variant sequences (i.e., homologs) that are functional in binding to Orphanin FQ or other neurotransmitter peptides. The purpose of screening such combinatorial libraries is to generate, for example, novel OFQR homologs express differential ligand binding properites, or alternatively, possess novel activities all together.

In some embodiments of the combinatorial mutagenesis approach of the present invention, the amino acid sequences for a population of OFQR homologs or other related proteins are aligned, preferably to promote the highest homology possible. Such a population of variants can include, for example, OFQR homologs from one or more species, or OFQR homologs from the same species but which differ due to mutation or splice variation. Amino acids that appear at each position of the aligned sequences are selected to create a degenerate set of combinatorial sequences.

In a preferred embodiment of the present invention, the combinatorial OFQR library is produced by way of a degenerate library of genes encoding a library of polypeptides which each include at least a portion of potential OFQR protein sequences. For example, a mixture of synthetic oligonucleotides can be enzymatically ligated into gene sequences such that the degenerate set of potential OFQR sequences are expressible as individual polypeptides, or alternatively, as a set of larger fusion proteins (e.g., for phage display) containing the set of OFQR sequences therein.

There are many ways by which the library of potential OFQR homologs can be generated from a degenerate oligonucleotide sequence. In some embodiments, chemical synthesis of a degenerate gene sequence is carried out in an automatic DNA synthesizer, and the synthetic genes are ligated into an appropriate gene for expression. The purpose of a degenerate set of genes is to provide, in one mixture, all of the sequences encoding the desired set of potential OFQR sequences. The synthesis of degenerate oligonucleotides is well known in the art (See e.g., Narang, Tetrahedron Lett., 39:3 9 [1983]; Itakura et al., Recombinant DNA, in Walton (ed.), *Proceedings of the 3rd Cleveland Symposium on Macromolecules*, Elsevier, Amsterdam, pp 273–289 [1981]; Itakura et al., Annu. Rev. Biochem., 53:323 [1984]; Itakura et al., Science 198:1056 [1984]; Ike et al., Nucl. Acid Res., 11:477 [1983]). Such techniques have been employed in the directed evolution of other proteins (See e.g., Scott et al., Science 249:386–390 [1980]; Roberts et al., Proc. Natl. Acad. Sci. USA 89:2429–2433 [1992]; Devlin et al., Science 249: 404–406 [1990]; Cwirla et al., Proc. Natl. Acad. Sci. USA 87: 6378–6382 [1990]; as well as U.S. Pat. Nos. 5,223,409, 5,198,346, and 5,096,815, each of which is incorporated herein by reference).

It is contemplated that the OFQR nucleic acids (e.g., SEQ ID NOs: 9, 10, 12, 14, 16, 18, 19, 20, and 21), and fragments and variants thereof) can be utilized as starting nucleic acids for directed evolution. These techniques can be utilized to develop OFQR variants having desirable properties such as increased or decreased binding affinity for Orphanin FQ.

In some embodiments, artificial evolution is performed by random mutagenesis (e.g., by utilizing error-prone PCR to introduce random mutations into a given coding sequence). This method requires that the frequency of mutation be finely tuned. As a general rule, beneficial mutations are rare, while deleterious mutations are common. This is because the combination of a deleterious mutation and a beneficial mutation often results in an inactive protein. The ideal number of base substitutions for targeted gene is usually between 1.5 and 5 (Moore and Arnold, Nat. Biotech., 14,458–67 [1996]; Leung et al., Technique, 1:11–15 [1989]; Eckert and Kunkel, PCR Methods Appl., 1:17–24 [1991]; Caldwell and Joyce, PCR Methods Appl., 2:28–33 (1992); and Zhao and Arnold, Nuc. Acids. Res., 25:1307–08 [1997]). After mutagenesis, the resulting clones are selected for desirable activity (e.g., screened for Orphanin FQ binding). Successive rounds of mutagenesis and selection are often necessary to develop enzymes with desirable properties. It should be noted that only the useful mutations are carried over to the next round of mutagenesis.

In other embodiments of the present invention, the polynucleotides of the present invention are used in gene shuffling or sexual PCR procedures (eg., Smith, Nature, 370:324–25 [1994]; U.S. Pat. Nos. 5,837,458; 5,830,721; 5,811,238; 5,733,731; all of which are herein incorporated by reference). Gene shuffling involves random fragmentation of several mutant DNAs followed by their reassembly by PCR into full length molecules. Examples of various gene shuffling procedures include, but are not limited to, assembly following DNase treatment, the staggered extension process (STEP), and random priming in vitro recombination. In the DNase mediated method, DNA segments isolated from a pool of positive mutants are cleaved into random fragments with DNaseI and subjected to multiple rounds of PCR with no added primer. The lengths of random fragments approach that of the uncleaved segment as the PCR cycles proceed, resulting in mutations in present in different clones becoming mixed and accumulating in some of the resulting sequences. Multiple cycles of selection and shuffling have led to the functional enhancement of several enzymes (Stemmer, Nature, 370:398–91 [1994]; Stemmer, Proc. Natl. Acad. Sci. USA, 91, 10747–51 [1994]; Crameri et al., Nat. Biotech., 14:315–19 [1996]; Zhang et al., Proc. Natl. Acad. Sci. USA, 94:4504–09 [1997]; and Crameri et al., Nat. Biotech., 15:436–38 [1997]). Variants produced by directed evolution can be screened for ligand binding using any suitable method, including but not limited to, those disclosed herein.

A wide range of techniques are known in the art for screening gene products of combinatorial libraries made by point mutations, and for screening cDNA libraries for gene products having a certain property. Such techniques will be generally adaptable for rapid screening of the gene libraries generated by the combinatorial mutagenesis or recombination of OFQR homologs. The most widely used techniques for screening large gene libraries typically comprises cloning the gene library into replicable expression vectors, transforming appropriate cells with the resulting library of vectors, and expressing the combinatorial genes under conditions in which detection of a desired activity facilitates relatively easy isolation of the vector encoding the gene whose product was detected.

E. Chemical Synthesis of OFQR

In an alternate embodiment of the invention, the coding sequence of an OFQR polypeptide is synthesized, whole or in part, using chemical methods well known in the art (See e.g., Caruthers et at., Nucl. Acids Res. Symp. Ser., 7:215–233 [1980]; Crea and Horn, Nucl. Acids Res., 9:2331 [1980]; Matteucci and Caruthers, Tetrahedron Lett., 21:719 [1980]; and Chow and Kempe, Nucl. Acids Res., 9:2807–2817 [1981]). In other embodiments of the present invention, the protein itself is produced using chemical methods to synthesize either an entire OFQR amino acid sequence (e.g., SEQ ID Nos: 11, 13, 15, and 17) or a portion thereof. For example, peptides can be synthesized by solid phase techniques, cleaved from the resin, and purified by preparative high performance liquid chromatography (See e.g., Creighton, *Proteins Structures And Molecular Principles*, W H Freeman and Co, New York N.Y. [1983]). In other embodiments of the present invention, the composition of the synthetic peptides is confirmed by amino acid analysis or sequencing (See e.g., Creighton, supra).

Direct peptide synthesis can be performed using various solid-phase techniques (Roberge et al., Science 269:202–204 [1995]) and automated synthesis may be achieved, for example, using ABI 431A Peptide Synthesizer (Perkin Elmer) in accordance with the instructions provided by the manufacturer. Additionally, an amino acid sequence of OFQR, or any part thereof, may be altered during direct synthesis and/or combined using chemical methods with other sequences to produce a variant polypeptide.

III. Generation of OFQR Antibodies

In some embodiments, the present invention provides antibodies specific to a OFQR polypeptide. Antibodies can be generated to allow for the detection of OFQR protein. The antibodies may be prepared using various immunogens. In one embodiment, an OFQR splice variant peptide is used as an immunogen in order to generate antibodies that recognize a specific splice variant of OFQR. Such antibodies include, but are not limited to polyclonal, monoclonal, chimeric, single chain, Fab fragments, and Fab expression libraries.

Various procedures known in the art may be used for the production of polyclonal antibodies directed against an OFQR splice variant. For the production of antibody, various host animals can be immunized by injection with the peptide corresponding to the OFQR epitope including but not limited to rabbits, mice, rats, sheep, goats, etc. In a preferred embodiment, the peptide is conjugated to an immunogenic carrier (e.g., diphtheria toxoid, bovine serum albumin (BSA), or keyhole limpet hemocyanin (KLH)). Various adjuvants may be used to increase the immunological response, depending on the host species, including but not limited to Freund's (complete and incomplete), mineral gels (e.g., aluminum hydroxide), surface active substances (e.g., lysolecithin, pluronic polyols, polyanions, peptides, oil emulsions, keyhole limpet hemocyanins, dinitrophenol, and potentially useful human adjuvants such as BCG (Bacille Calmette-Guerin) and *Corynebacterium parvum*).

For preparation of monoclonal antibodies directed toward an OFQR polypeptide, it is contemplated that any technique that provides for the production of antibody molecules by continuous cell lines in culture will find use with the present invention (See e.g., Harlow and Lane, *Antibodies: A Laboratory Manual*, Cold Spring Harbor Laboratory Press, Cold Spring Harbor, N.Y.). These include, but are not limited to, the hybridoma technique originally developed by Köhler and Milstein (Köhler and Milstein, Nature 256:495–497 [1975]), as well as the trioma technique, the human B-cell hybridoma technique (See e.g., Kozbor et al., Immunol. Tod., 4:72 [1983]), and the EBV-hybridoma technique to produce human monoclonal antibodies (Cole et al., in *Monoclonal Antibodies and Cancer Therapy*, Alan R. Liss, Inc., pp. 77–96 [1985]).

In an additional embodiment of the invention, monoclonal antibodies are produced in germ-free animals utilizing technology such as that described in PCT/US90/02545). Furthermore, it is contemplated that human antibodies will be generated by human hybridomas (Cote et al., Proc. Natl. Acad. Sci. USA 80:2026–2030 [1983]) or by transforming human B cells with EBV virus in vitro (Cole et al., in *Monoclonal Antibodies and Cancer Therapy*, Alan R. Liss, pp. 77–96 [1985]).

In addition, it is contemplated that techniques described for the production of single chain antibodies (U.S. Pat. No. 4,946,778; herein incorporated by reference) will find use in producing OFQR specific single chain antibodies. An additional embodiment of the invention utilizes the techniques described for the construction of Fab expression libraries (Huse et al., Science 246:1275–1281 [1989]) to allow rapid and easy identification of monoclonal Fab fragments with the desired specificity for a specific OFQR polypeptide.

It is contemplated that any technique suitable for producing antibody fragments will find use in generating antibody fragments that contain the idiotype (antigen binding region) of the antibody molecule. For example, such fragments include but are not limited to: F(ab')2 fragment that can be produced by pepsin digestion of the antibody molecule; Fab' fragments that can be generated by reducing the disulfide bridges of the F(ab')2 fragment, and Fab fragments that can be generated by treating the antibody molecule with papain and a reducing agent.

In the production of antibodies, it is contemplated that screening for the desired antibody will be accomplished by techniques known in the art (e.g., radioimmunoassay, ELISA (enzyme-linked immunosorbant assay), "sandwich" immunoassays, immunoradiometric assays, gel diffusion precipitation reactions, immunodiffusion assays, in situ immunoassays (e.g., using colloidal gold, enzyme or radioisotope labels, for example), Western blots, precipitation reactions, agglutination assays (e.g.,gel agglutination assays, hemagglutination assays, etc.), complement fixation assays, immunofluorescence assays, protein A assays, and immunoelectrophoresis assays, etc.

In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many means are known in the art for detecting binding in an immunoassay and are within the scope of the present invention. As is well known in the art, the immunogenic peptide should be provided free of the carrier molecule used in any immunization protocol. For example, if the peptide was conjugated to KLH, it may be conjugated to BSA, or used directly, in a screening assay.

The foregoing antibodies can be used in methods known in the art relating to the localization and structure of an OFQR polypeptide (e.g., for Western blotting), measuring levels thereof in appropriate biological samples, etc. The antibodies can be used to detect OFQR in a specific tissue (e.g., brain or gastrointestinal tissue).

The biological tissue samples can then be tested directly for the presence of an OFQR polypeptide using an appropriate strategy (e.g., ELISA or radioirmnunoassay) and format (e.g., microwells, dipstick (e.g., as described in International Patent Publication WO 93/03367), etc. Alternatively, proteins in the sample can be size separated (e.g., by polyacrylamide gel electrophoresis (PAGE), in the presence or not of sodium dodecyl sulfate (SDS), and the presence of OFQR detected by immunoblotting (Western blotting). Inmuunoblotting techniques are generally more effective with antibodies generated against a peptide corresponding to an epitope of a protein, and hence, are particularly suited to the present invention.

Another method uses antibodies as agents to alter signal transduction. Specific antibodies that bind to the binding domains of OFQR involved in signalling can be used to inhibit the interaction between the various proteins and their interaction with other ligands. Antibodies that bind to the complex can also be used therapeutically to inhibit interactions of the protein complex in the signal transduction pathways leading to the various physiological and cellular effects of Orphanin FQ. Such antibodies can also be used diagnostically to measure abnormal expression of OFQR, or the aberrant formation of protein complexes, which may be indicative of a disease state.

IV. Drug Screening Using OFQR

The present invention provides methods and compositions for using OFQR as a target for screening drugs. In some embodiments, drug screening assays are used to identify compounds that can alter, for example, the binding of Orphanin FQ to OFQR. In other embodiments, drug screens are used to identify OFQR agonists and antagonists. In preferred embodiments, one or more splice variants of OFQR are utilized to identify compounds that are active towards some (e.g., one), but not all, receptor variants. The present invention thus provides methods of identifying compounds that are active in specific tissues or organs.

Previous studies have suggested that Orphanin FQ modulates a variety of biological functions including nociception (pain), food intake, memory processes, caridovacular and renal function, spontaintaneous locomotor activity, gastrointestinal motility, anxiety and neurotransmitter release (Calo et al., Br. J. Pharmacol 129:1261 [2000]). Specifically, Orphanin FQ reduces elementary stress-induced physiological responses such as analgesia in rodents and attenuates elaborate behavioral fear responses elicited when animal are exposed to stressfil/anxiogenic situations (Jenck et al., PNAS 97:4938 [2000]; Koster et al., PNAS 96:10444). Orphanin FQ has also been found to play a role in pain perception by the measurement of thermal hyperalgesia in rats following nerve injury (Yamamoto and Nozaki-Taguchi, Anesthesiology 87:1145 [1997]). Orphanin FQ has further been shown to play a role in gastrointestinal motility in rats (Yazdani et al., Gastroenterology, 116:108 [1999]).

The present invention is not limited to a particular mechanism. Indeed, an understanding of the mechanism is not necessary to practice the present invention. Nonetheless, it is contemplated that the diverse effects of Orphanin FQ in a variety of tissues are due to the preferential expression of different splice variants in different tissues (See Example 4). Thus, it is contemplated that OFQR antagonists or agonists can be targeted to specific tissues and physiological responses (e.g., pain, gastrointestinal motility, learning and memory, drug dependence, and stress-related neuronal dysfunctions).

The present invention is not limited to any one drug-screening method. Indeed, any suitable method may be utilized. In some embodiments, drug screening is carried out using the method described in U.S. Pat. No. 6,172,075 (herein incorporated by reference). Briefly, the cDNA for a particular splice variant of OFQR is cloned into an expression vector (e.g., including, but not limited to, those described above) and expressed in a mammalian cell line (e.g., including, but not limited to, those described above). In some embodiments, greater than one (e.g., two) OFQR receptors are expressed in the same cell (See e.g., U.S. Pat. No. 5,976,807; herein incorporate by reference).

In some embodiments, binding assays are performed with intact cells expressing OFQR receptor on their surfaces (the presence of OFQR on cell surfaces can be determined, for example, by one of the immunological methods described above). In other embodiments, membrane fractions are isolated from the cells (See e.g., U.S. Pat. No. 6,172,075).

Binding assays arc next performed using any suitable method. For example, in some embodiments, filter binding assays utilizing radiolabelled OFQR are used to assay the binding of a ligand to OFQR (See e.g., U.S. Pat. No. 6,172,075; herein incorporated by reference). In other embodiments, binding is assayed by ligand binding associated inhibition of forskolin-stimulated camp accumulation (See e.g., U.S Pat. No. 5,821,219; herein incorporated by reference). In still other embodiments, a reporter gene expression assay is utilized in which cells are transformed with a plasmid containing an OFQR gene and a second plasmid containing a reporter plasmid (e.g., cAMP responsive element) (See e.g., Wnendt et al., Mol. Pharmacol. 56:334 [1999] and U.S. Pat. No. 5,976,807; herein incorporated by reference for exemplary methods).

Another technique for drug screening provides high throughput screening for compounds having suitable binding affinity to OFQR and is described in detail in WO 84/03564, incorporated herein by reference. Briefly, large numbers of different small peptide test compounds are synthesized on a solid substrate, such as plastic pins or some other surface. The peptide test compounds are then reacted with OFQR and washed. Bound OFQR polypeptides are then detected by methods well known in the art.

Another technique uses OFQR antibodies, generated as discussed above. Such antibodies capable of binding to specific OFQR splice variants compete with a test compound for binding to an OFQR polypeptide. In this manner, the antibodies can be used to detect the presence of any peptide that shares one or more antigenic determinants of a specific OFQR polypeptide.

The present invention contemplates many other means of screening compounds. The examples provided above are presented merely to illustrate a range of techniques available. One of ordinary skill in the art will appreciate that many other screening methods can be used.

In particular, the present invention contemplates the use of cell lines transfected with OFQR splice variants and variants or mutants thereof for screening compounds for activity, and in particular to high throughput screening of compounds from combinatorial libraries (e.g., libraries containing greater than $10^4$ compounds). The cell lines of the present invention can be used in a variety of screening methods. In some embodiments, the cells can be used in second messenger assays that monitor signal transduction following activation of cell-surface receptors. In other embodiments, the cells can be used in reporter gene assays that monitor cellular responses at the transcription/translation level. In still further embodiments, the cells can be used in cell proliferation assays to monitor the overall growth/no growth response of cells to external stimuli.

In second messenger assays, the host cells are preferably transfected as described above with vectors encoding OFQR splice variants or variants or mutants thereof. The host cells are then treated with a compound or plurality of compounds (e.g., from a combinatorial library) and assayed for the presence or absence of a response. It is contemplated that at least some of the compounds in the combinatorial library can serve as agonists, antagonists, activators, or inhibitors of the protein or proteins encoded by the vectors. It is also contemplated that at least some of the compounds in the combinatorial library can serve as agonists, antagonists, activators, or inhibitors of protein acting upstream or downstream of the protein encoded by the vector in a signal transduction pathway.

In some embodiments, the second messenger assays measure fluorescent signals from reporter molecules that respond to intracellular changes (e.g., $Ca^{2+}$ concentration, membrane potential, pH, $IP_3$, cAMP, arachidonic acid release) due to stimulation of membrane receptors and ion channels (e.g., ligand gated ion channels; see Denyer et al., Drug Discov. Today 3:323–32 [1998]; and Gonzales et al., Drug. Discov. Today 4:431–39 [1999]). Examples of reporter molecules include, but are not limited to, FRET (florescence resonance energy transfer) systems (e.g., Cuo-lipids and oxonols, EDAN/DABCYL), calcium sensitive indicators (e.g., Fluo-3, FURA 2, INDO 1, and FLUO3/AM, BAPTA AM), chloride-sensitive indicators (e.g., SPQ, SPA), potassium-sensitive indicators (e.g., PBFI), sodium-sensitive indicators (e.g., SBFI), and pH sensitive indicators (e.g., BCECF).

In general, the host cells are loaded with the indicator prior to exposure to the compound. Responses of the host cells to treatment with the compounds can be detected by methods known in the art, including, but not limited to, fluorescence microscopy, confocal microscopy (e.g., FCS systems), flow cytometry, microfluidic devices, FLIPR systems (See, e.g., Schroeder and Neagle, J. Biomol. Screening 1:75–80 [1996]), and plate-reading systems. In some preferred embodiments, the response (e.g., increase in fluorescent intensity) caused by compound of unknown activity is compared to the response generated by a known agonist and expressed as a percentage of the maximal response of the known agonist. The maximum response caused by a known agonist is defined as a 100% response. Likewise, the maximal response recorded after addition of an agonist to a sample containing a known or test antagonist is delectably lower than the 100% response.

The cells are also useful in reporter gene assays (e.g., as described above). Reporter gene assays involve the use of host cells transfected with vectors encoding a nucleic acid comprising transcriptional control elements of a target gene (i.e., a gene that controls the biological expression and function of a disease target) spliced to a coding sequence for a reporter gene. Therefore, activation of the target gene results in activation of the reporter gene product.

Examples of reporter genes finding use in the present invention include, but are not limited to, chloramphenicol transferase, alkaline phosphatase, firefly and bacterial luciferases, β-galactosidase, β-lactamase, and green fluorescent protein. The production of these proteins, with the exception of green fluorescent protein, is detected through the use of chemiluminescent, colorimetric, or bioluminecent products of specific substrates (e.g., X-gal and luciferin). Comparisons between compounds of known and unknown activities may be conducted as described above.

In some embodiments, drug screening assays are performed (e.g., using one of the methods described above) in which multiple splice variants (e.g., two or more) of OFQR are simultaneously assayed. The variants can be expressed in one cell line, or alternatively, in a series of membrane preparations. In such an analysis, the comparative effect of multiple compounds can be assayed. The ability of compounds to compete with each other and/or the endogenous ligand (e.g., Orphanin FQ) provides data useful in identifying potential therapeutics.

V. Pharmaceutical Compositions

The present invention further provides pharmaceutical compositions (e.g., those developed by the drug screening applications described above) which may comprise agonists or antagonists of OFQR, including antibodies, peptides, antisense oligonucleotides, and small molecule compounds, alone or in combination with at least one other agent, such as a stabilizing compound, and may be administered in any sterile, biocompatible pharmaceutical carrier, including, but not limited to, saline, buffered saline, dextrose, and water.

The methods of the present invention find use in treating diseases or altering physiological states characterized by Orphanin FQ/OFQR signaling. Consequently, compounds developed using the methods of the present invention are useful in the treatment of psychiatric, neurological and physiological disorders, especially, but not limited to, amelioration of symptoms of anxiety and stress disorders, depression, trauma, memory loss due to Alzheimer's disease or other dementias, epilepsy and convulsions, acute and/or chronic pain conditions, symptoms of addictive drug withdrawal, control of water balance, $Na^+$ excretion, arterial blood pressure disorders and metabolic disorders such as obesity.

The formulations developed by the methods of the present invention are useful for parenteral administration, such as intravenous, subcutaneous, intramuscular, and intraperitoneal. As is well known in the medical arts, dosages for any one patient depends upon many factors, including the patient's size, body surface area, age, the particular compound to be administered, sex, time and route of administration, general health, and interaction with other drugs being concurrently administered.

Accordingly, in some embodiments of the present invention, compounds developed by the drug screening methods of the present invention can be administered to a patient alone, or in combination with nucleotide sequences, drugs or hormones or in pharmaceutical compositions where it is mixed with excipient(s) or other pharmaceutically acceptable carriers. In one embodiment of the present invention, the pharmaceutically acceptable carrier is pharmaceutically inert. In another embodiment of the present invention, compounds may be administered alone to individuals subject to or suffering from a disease.

Depending on the condition being treated, these pharmaceutical compositions may be formulated and administered systemically or locally. Techniques for formulation and administration may be found in the latest edition of "Remington's Pharmaceutical Sciences" (Mack Publishing Co, Easton Pa.). Suitable routes may, for example, include oral or transmucosal administration; as well as parenteral delivery, including intramuscular, subcutaneous, intramredullary, intrathecal, intraventricular, intravenous, intraperitoneal, or intranasal administration.

For injection, the pharmaceutical compositions of the invention may be formulated in aqueous solutions, preferably in physiologically compatible buffers such as Hanks' solution, Ringer's solution, or physiologically buffered saline. For tissue or cellular administration, penetrants appropriate to the particular barrier to be permeated are used in the formulation. Such penetrants are generally known in the art.

In other embodiments, the pharmaceutical compositions of the present invention can be formulated using pharmaceutically acceptable carriers well known in the art in dosages suitable for oral administration, Such carriers enable the pharmaceutical compositions to be formulated as tablets, pills, capsules, liquids, gels, syrups, slurries, suspensions and the like, for oral or nasal ingestion by a patient to be treated.

Pharmaceutical compositions suitable for use in the present invention include compositions wherein the active ingredients are contained in an effective amount to achieve the intended purpose. For example, an effective amount of composition may be that amount that results in substantial elimination of symptoms characteristic of the disease state being treated. Determination of effective amounts is well within the capability of those skilled in the art, especially in light of the disclosure provided herein.

In addition to the active ingredients these pharmaceutical compositions may contain suitable pharmaceutically acceptable carriers comprising excipients and auxiliaries which facilitate processing of the active compounds into preparations which can be used pharmaceutically. The preparations formulated for oral administration may be in the form of tablets, dragees, capsules, or solutions.

The pharmaceutical compositions of the present invention may be manufactured in a manner that is itself known (e.g., by means of conventional mixing, dissolving, granulating, dragee-making, levigating, emulsifying, encapsulating, entrapping or lyophilizing processes).

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Pharmaceutical preparations for oral use can be obtained by combining the active compounds with solid excipient, optionally grinding a resulting mixture, and processing the mixture of granules, after adding suitable auxiliaries, if desired, to obtain tablets or dragee cores. Suitable excipients are carbohydrate or protein fillers such as sugars, including lactose, sucrose, mannitol, or sorbitol; starch from corn, wheat, rice, potato, etc; cellulose such as methyl cellulose, hydroxypropylmethyl-cellulose, or sodium carboxymethylcellulose; and gums including arabic and tragacanth; and proteins such as gelatin and collagen. If desired, disintegrating or solubilizing agents may be added, such as the cross-linked polyvinyl pyrrolidone, agar, alginic acid or a salt thereof such as sodium alginate.

Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, (i.e., dosage).

Pharmaceutical preparations that can be used orally include push-fit capsules made of gelatin, as well as soft, sealed capsules made of gelatin and a coating such as glycerol or sorbitol. The push-fit capsules can contain the active ingredients mixed with fillers or binders such as lactose or starches, lubricants such as talc or magnesium stearate, and, optionally, stabilizers. In soft capsules, the active compounds may be dissolved or suspended in suitable liquids, such as fatty oils, liquid paraffin, or liquid polyethylene glycol with or without stabilizers.

Compositions comprising a compound of the invention formulated in a pharmaceutical acceptable carrier may be prepared, placed in an appropriate container, and labeled for treatment of an indicated condition.

The pharmaceutical composition may be provided as a salt and can be formed with many acids, including but not limited to hydrochloric, sulfuric, acetic, lactic, tartaric, malic, succinic, etc. Salts tend to be more soluble in aqueous or other protonic solvents that are the corresponding free base forms. In other cases, the preferred preparation may be a lyophilized powder in 1 mM–50 mM histidine, 0.1%–2%, sucrose, 2%–7% mannitol at a pH range of 4.5 to 5.5 that is combined with buffer prior to use.

For any compound used in the method of the invention, the therapeutically effective dose can be estimated initially from cell culture assays. Then, preferably, dosage can be formulated in animal models (particularly murine models) to achieve a desirable circulating concentration range that adjusts the level of the compound.

A therapeutically effective dose refers to that amount of the compound developed by the methods of the present invention that ameliorates symptoms of the disease state. Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index, and it can be expressed as the ratio $LD_{50}/ED_{50}$. Compounds that exhibit large therapeutic indices are preferred. The data obtained from these cell culture assays and additional animal studies can be used in formulating a range of dosage for human use. The dosage of such compounds lies preferably within a range of circulating concentrations that include the $ED_{50}$ with little or no toxicity. The dosage varies within this range depending upon the dosage form employed, sensitivity of the patient, and the route of administration.

The exact dosage is chosen by the individual physician in view of the patient to be treated. Dosage and administration are adjusted to provide sufficient levels of the active moiety or to maintain the desired effect. Additional factors which may be taken into account include the severity of the disease state; age, weight, and gender of the patient; diet, time and frequency of administration, drug combination(s), reaction sensitivities, and tolerance/response to therapy. Long acting pharmaceutical compositions might be administered every 3 to 4 days, every week, or once every two weeks depending on half-life and clearance rate of the particular formulation.

Normal dosage amounts may vary from 0.1 to 100,000 micrograms, up to a total dose of about 1 g, depending upon the route of administration. Guidance as to particular dosages and methods of delivery is provided in the literature (See, U.S. Pat. Nos. 4,657,760; 5,206,344; or 5,225,212, all of which are herein incorporated by reference). Administration to the bone marrow may necessitate delivery in a manner different from intravenous injections.

VI. Transgenic Animals Expressing Exogenous OFQR Genes and Splice Variants, Homologs, Mutants, and Variants thereof The present invention contemplates the generation of transgenic animals comprising an exogenous OFQR gene or splice variants, homologs, mutants, or variants thereof. In preferred embodiments, the transgenic animal displays an altered phenotype as compared to wild-type animals. In some embodiments, the altered phenotype is the overexpression of mRNA for an OFQR gene (e.g., a splice variant) as compared to wild-type levels of OFQR expression. In other embodiments, the altered phenotype is the decreased expression of mRNA for an endogenous OFQR gene (e.g., a splice variant) gene as compared to wild-type levels of endogenous OFQR expression. Methods for analyzing the presence or absence of such phenotypes include Northern blotting, mRNA protection assays, and RT-PCR. In other embodiments, the transgenic animals have a knock out mutation of one or more variants of the OFQR gene (e.g., including but not limited to, splice variants). In still further embodiments, transgenic animals express a OFQR mutant gene. Since the specific tissue where different variants of OFQR are known, mutations, knock outs, etc. can be targeted to a specific tissue in order to study the localized effect of Orphanin FQ/OFQR signaling.

In some embodiments, the transgenic animals of the present invention find use in drug screens. In some embodiments, test compounds (e.g., a drug developed by the drug screening methods described above) and control compounds (e.g., a placebo) are administered to the transgenic animals and the control animals and the effects evaluated.

The transgenic animals can be generated via a variety of methods. In some embodiments, embryonal cells at various developmental stages are used to introduce transgenes for the production of transgenic animals. Different methods are used depending on the stage of development of the embryonal cell. The zygote is the best target for micro-injection. In the mouse, the male pronucleus reaches the size of approximately 20 micrometers in diameter, which allows reproducible injection of 1–2 picoliters (pl) of DNA solution. The use of zygotes as a target for gene transfer has a major advantage in that in most cases the injected DNA will be incorporated into the host genome before the first cleavage (Brinster et at., Proc. Natl. Acad. Sci. USA 82:4438–4442 [1985]). As a consequence, all cells of the transgenic non-human animal will carry the incorporated transgene. This will in general also be reflected in the efficient transmission of the transgene to offspring of the founder since 50% of the germ cells will harbor the transgene. U.S. Pat. No. 4,873,191 describes a method for the micro-injection of zygotes; the disclosure of this patent is incorporated herein in its entirety.

In other embodiments, retroviral infection is used to introduce transgenes into a non-human animal. In some embodiments, the retroviral vector is utilized to transfect oocytes by injecting the retroviral vector into the perivitelline space of the oocyte (U.S. Pat. No. 6,080,912, incorporated herein by reference). In other embodiments, the developing non-human embryo can be cultured in vitro to the blastocyst stage. During this time, the blastomeres can be targets for retroviral infection (Janenich, Proc. Natl. Acad. Sci. USA 73:1260–1264 [1976]). Efficient infection of the blastomeres is obtained by enzymatic treatment to remove the zona pellucida (Hogan et al., in *Manipulating the Mouse Embryo*, Cold Spring Harbor Laboratory Press, Cold Spring Harbor, N.Y. [1986]). The viral vector system used to introduce the transgene is typically a replication-defective retrovirus carrying the transgene (D. Jahner et al., Proc. Natl. Acad. Sci. USA 82:6927–693 [1985]). Transfection is easily and efficiently obtained by culturing the blastomeres on a monolayer of virus-producing cells (Van der Putten, supra; Stewart, et al., EMBO J., 6:383–388 [1987]). Alternatively, infection can be performed at a later stage. Virus or virus-producing cells can be injected into the blastocoele (D. Jahner et al., Nature 298:623–628 [1982]). Most of the founders will be mosaic for the transgene since incorporation occurs only in a subset of cells which form the transgenic animal. Further, the founder may contain various retroviral insertions of the transgene at different positions in the genome which generally will segregate in the offspring. In addition, it is also possible to introduce transgenes into the germline, albeit with low efficiency, by intrauterine retroviral infection of the midgestation embryo (Jahner et al., supra [1982]). Additional means of using retroviruses or retroviral vectors to create transgenic animals known to the art involves the micro-injection of retroviral particles or mitomycin C-treated cells producing retrovirus into the perivitelline space of fertilized eggs or early embryos (PCT International Application WO 90/08832 [1990], and Haskell and Bowen, Mol. Reprod. Dev., 40:386 [1995]).

In other embodiments, the transgene is introduced into embryonic stem cells and the transfected stem cells are utilized to form an embryo. ES cells are obtained by culturing pre-implantation embryos in vitro under appropriate conditions (Evans et al., Nature 292:154–156 [1981]; Bradley et al., Nature 309:255–258 [1984]; Gossler et al., Proc. Acad. Sci. USA 83:9065–9069 [1986]; and Robertson et al., Nature 322:445–448 [1986]). Transgenes can be efficiently introduced into the ES cells by DNA transfection by a variety of methods known to the art including calcium phosphate co-precipitation, protoplast or spheroplast fusion, lipofection and DEAE-dextran-mediated transfection. Transgenes may also be introduced into ES cells by retrovirus-mediated transduction or by micro-injection. Such transfected ES cells can thereafter colonize an embryo following their introduction into the blastocoel of a blastocyst-stage embryo and contribute to the germ line of the resulting chimeric animal (for review, See, Jaenisch, Science 240:1468–1474 [1988]). Prior to the introduction of transfected ES cells into the blastocoel, the transfected ES cells may be subjected to various selection protocols to enrich for ES cells which have integrated the transgene assuming that the transgene provides a means for such selection. Alternatively, the polymerase chain reaction may be used to screen for ES cells which have integrated the transgene. This technique obviates the need for growth of the transfected ES cells under appropriate selective conditions prior to transfer into the blastocoel.

In still other embodiments, homologous recombination is utilized knock-out gene function or create deletion mutants (e.g., mutants in which the OFQR is altered to effect its ligand binding or signaling abilities). Methods for homologous recombination are described in U.S. Pat. No. 5,614,396, incorporated herein by reference.

EXAMPLES

The following examples serve to illustrate certain preferred embodiments and aspects of the present invention and are not to be construed as limiting the scope thereof.

In the experimental disclosure which follows, the following abbreviations apply: eq (equivalents); $\mu$(micron); M (Molar); $\mu$M (micromolar); mM (millimolar); N (Normal); mol (moles); mmol (millimoles); $\mu$mol (micromoles); nmol (nanomoles); g (grams); mg (milligrams); $\mu$g (micrograms); ng (nanograms); L (liters); ml (milliliters); $\mu$l (microliters);

cm (centimeters); mm (millimeters); μm (micrometers); nM (nanomolar);° C. (degrees Centigrade); and PBS (phosphate buffered saline).

Example 1

Isolation of OFQR Genomic Clones

This example describes the isolation of genomic clones from rat containing the OFQR. A rat genomic library in the bacteriophage EMBL-3 (Clontech) was screened as previously reported (Blandizzi et al., Biochem. Biophys. Res. Commun. 202:947 [1994]), using a $^{32}$P-labeled cDNA fragment generated by the polymerase chain reaction (PCR) with primers based on the cDNA sequences of the rat OFQR (U01913, Bunzow et al., FEBS Lett. 347:284 [1994]; and L29419, Wick et al., Brain Res. Mol. Brain Res. 27:37 [1994]). Positive clones were digested with Pst I, Acc I, and Sac I. The resulting restriction fragments were subcloned into phage M13mp1 8 or -mp19 and sequenced in both directions by the dideoxy chain termination method (Sanger et al., 1977) using the T7 Sequenase Kit (Amersham). Oligonucleotide primers for sequencing or for PCR were synthesized on a DNA synthesizer (Applied Biosystems-380B). Computer analysis of nucleotide sequences was performed with the Genetics Computer Group (GCG) program (Biotechnology Center, University of Wisconsin, Madison, Wis.).

A random-primed $^{32}$P-labeled rat OFQR cDNA probe gave positive hybridization signals with five clones of $10^6$ plaques from a rat genomic library. Two of the genomic clones were overlapped to cover the full-length sequence of the gene encoding OFQR. The rat OFQR gene exceeded 10 kb in length and contained six exons, which were interrupted by five introns (FIG. 1). All exon/intron boundaries conformed to known splice junction consensus sequences (Mount, Nucleic Acids Res. 10:459 [1982]) (Table 2). The ATG translation initiation codon was located in exon 2, and the open reading frame consisted of 1283 bp and six exons ranging from 34 to 524 bp (FIG. 2). An mRNA variant containing exon 4 (see FIG. 4C for splice variants) is formed by joining nt 2344 (splice donor G/gt) to nt 2628 (acceptor ag/GC), which results in a threonine (T) residue at position 136 and early termination at nt 2639–2641 (TGA). Splice variants deleted for exons 3 and 4 cause a translation frameshift, avoiding early termination and resulting in the replacement of serine (S) with arginine (R) at position 75 in exon 2, and threonine (T) with histidine (H) at position 136 in exon 5. In these forms, the stop codon (TGA) is located at nt 3586–3588 in exon 6.

Exon 2 encodes the putative extracellular amino terminus and transmembrane (TM)-spanning region I of the receptor. Exon 5 encodes TM regions II to IV, and exon 6 encodes the remaining TM regions V to VII and the intracellular carboxyl terminus. The 5' flanking region of the rat OFQR gene (FIG. 2) contains a tandem dinucleotide sequence $(GA)_{26}$, two $(AAAAC)_3$ repeat sequences, two potential recognition sites for RNA polymerase II (TATA), and common motifs for transcription factors, such as Ap2 and Sp1. The OFQR nucleotide sequence, including that of the 5' flanking region (FIG. 2) has been deposited in the GenBank database under the accession number AF216218.

Example 2

Primer Extension Analysis

This Example describes the use of primer extension analysis to determine the putative transcription initiation sites of the OFQR gene. Primer extension was performed with poly (A)$^+$ RNA (500 ng) from rat brain and colon combined with two end-labeled antisense oligonucleotide primers: P18 (5' GCAGCAGCCGGTGCGGCAGCCAG3' ; (SEQ ID NO: 1) and P42 (5' TAGACACCGTCCACTGAG-GCC3' ; SEQ ID NO:2), as previously described (Muraoka et al., Am. J. Physiol. 271:G1101 [1996]). FIG. 2 shows the location of the primers (exon 1 and intron 1, respectively).

Figure 3:
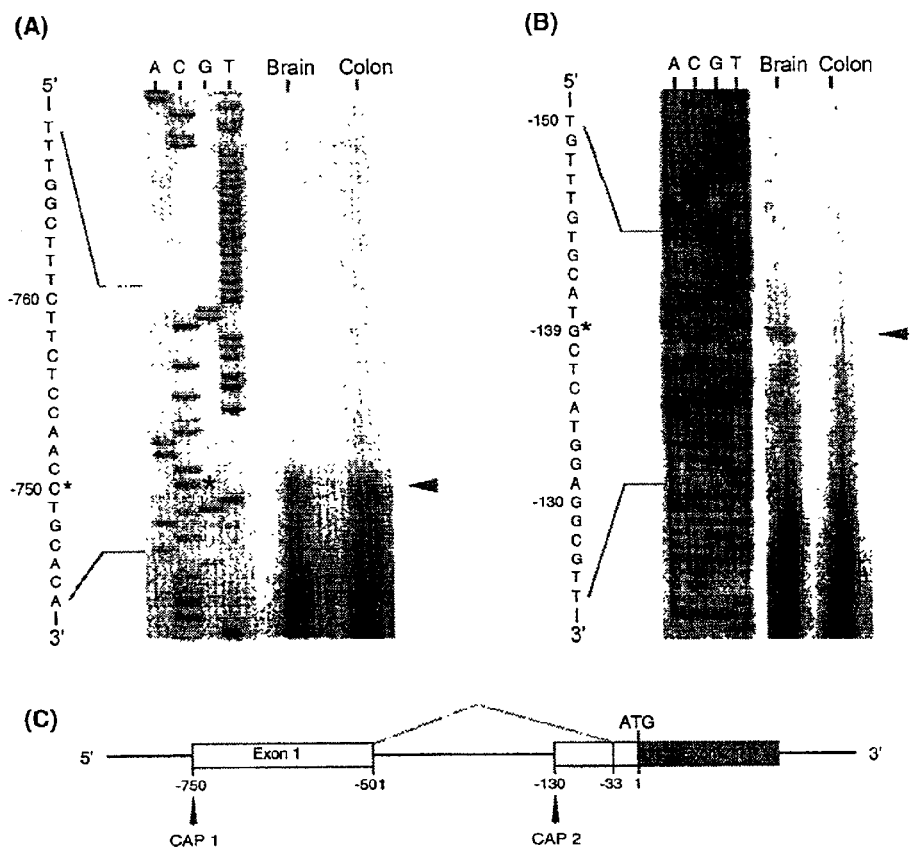

When the end-labeled primer P18 was used in the extension reaction, an elongation product of 72 bp was detected in both brain and colon, and the transcription initiation site was identified as the cytosine 103 bp downstream from the TATA box at nt 750 in the 5' flanking region (FIG. 3A). In contrast, when primer P42 was used, an elongation product of 71 bp was detected in brain tissue only, and the transcription initiation site was identified as the guanine 133 bp downstream from the TATA box at nt 139 in intron 1 (FIG. 3B).

Example 3

PCR Cloning of Gene Splice Variants

PCR cloning was performed with poly (A)$^+$ RNA (150 ng) from rat brain, colon, and liver using strategically designed oligonucleotide primers (Table 1), as previously reported (Song et al., Proc. Natl. Acad. Sci. U S A. 90, 9085 [1993]). Primer P13 (SEQ ID NO:7) in the 3' untranslated region was used in combination with either primer P9 (SEQ ID NO:6) in exon 1 or primer P3 (SEQ ID NO:3) in intron 1 to produce full-length cDNAs. Primer P3 containing the 20-mer of intron 1 sequence was designed to verify splice variants that did not express exon 1. The resulting PCR products served as the templates for subsequent PCRs using internal primers P5 (SEQ ID NO:4) and P 10 (SEQ ID NO:5). Gene splice variants were identified by sequencing as described above.

Figure 4:
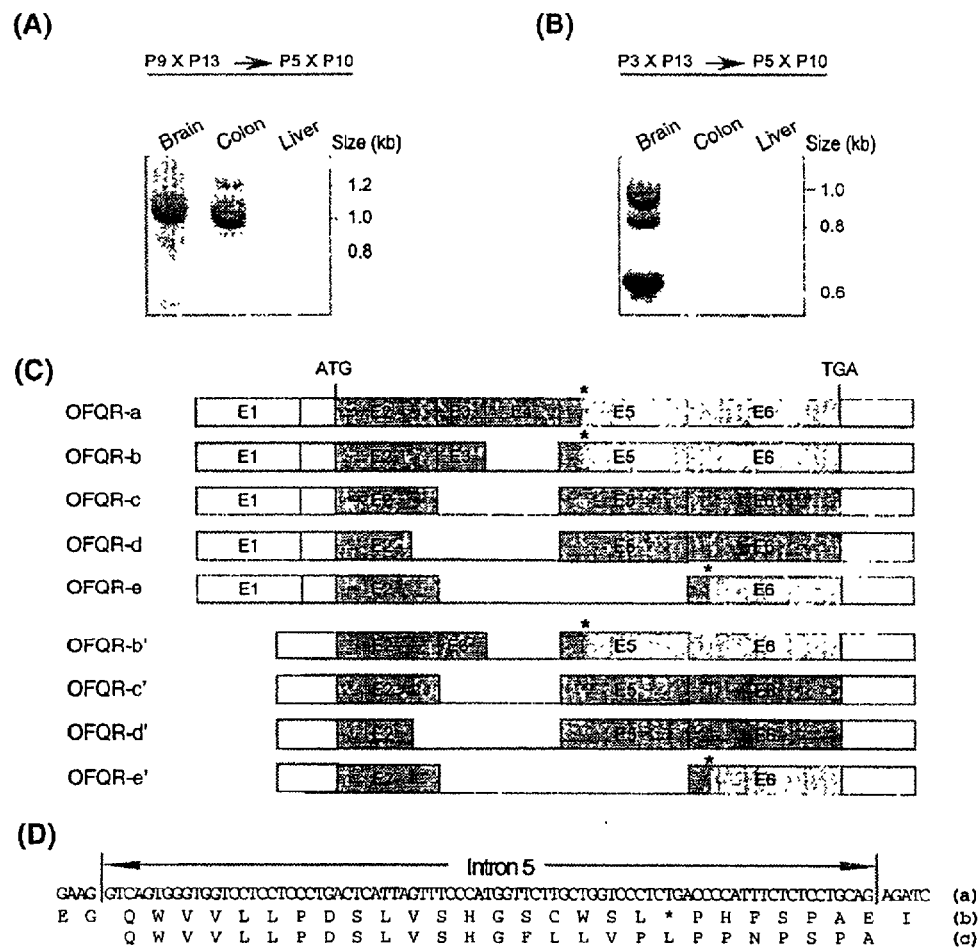

When primers P9 and P13 followed by primers P5 and P10 were used for PCR, multiple bands were obtained from the brain and colon RNA (FIG. 4A), rather than the expected single band. Using primers P3 and P 13 followed by primers P5 and P 10, specific bands were demonstrated only in brain, as shown in FIG. 4B. The sequencing results of these PCR products revealed that rat OFQR expressed at least nine splice variants deleted for exon 1, or exons 3 to 5, as shown in FIG. 5C. Previously reported cDNAs LC132 (Bunzow et al., FEBS Lett. 347:284 [1994]) and Hyp 8-1 (Wick et al., Brain Res. Mol. Brain Res. 27:37 [1994]) deleted for exon 1 had the same sequence as the OFQR-c and OFQR-c', respectively. Pan et al., Gene 171: 255 [1998] reported that the coding regions of OFQR-b (-b'), -c (-c'), and -d (-d') splice variants corresponded to the coding regions of KOR-3a, -3, and -3d, respectively, in mouse brain. Unlike the OFQR-c (-c') and -d (-d') isoforms, translation of the OFQR-a, -b (-b'), and -e (-e') is predicted to result in early termination at exon 5 or 6 due to shifts of the open reading frame (FIG. 4C). We did not detect a splice variant containing intron 5, as reported by Wang et al., supra. In addition, the amino acid sequence deduced by this study varies from that published by Wang et al., supra, as shown in FIG. 4D.

Example 4

Expression of Alternative Splicing in Various Rat Tissues

RT-PCR with poly (A)$^+$ RNA (150 ng) from various rat tissues (brain, liver, kidney, Vio heart, lung, spleen, skeletal muscle, testes, esophagus, gastric fundus, corpus, antrum, pylorus, duodenum, jejunum, ileum, proximal colon, and distal colon) was performed using primers P5 and P29 (Table 1). The splice variants were analyzed by Southern blot or the ScanJet 4c/T (Hewlett Packard). A housekeeping gene, GAPDH, served as an internal control.

As shown in FIG. 5A, PCR products of OFQR variants were not detected in liver, kidney, heart, lung, spleen, or skeletal muscle, whereas two forms, OFQR-a and -c, were expressed in testes. These forms, in addition to OFQR-b, were expressed in pylorus, ileum, and proximal colon. Both forms, OFQR-b and -c (or -d) were expressed in brain and antrum. OFQR-c (or -d) was expressed in esophagus, findus, corpus, duodenum, jejunum, and descending colon. OFQR-c and -d could not be distinguished in the electrophoretic analysis of RT-PCR products due to the small size difference (i.e., 15 bp). As shown in FIG. 5B, the OFQR-c' or -d' splice variants were expressed only in brain. The sequencing data agree in part with the results of Wang et al., supra and Osinski et al., Eur. J. Pharmacol. 365, 281 [1999]), who used RT-PCR to study the expression of OFQR in rat and pig tissues, respectively.

TABLE 1

Sequence of Oligonucleotide Primers Used in PCR

| Name | Location | Orientation | Sequence (5'-3') |
|---|---|---|---|
| P3 | Intron 1/ Exon 2 | Sense | gtttctgtgccctgttccagGAACTG (SEQ ID NO:3) |
| P5 | Exon 2 | Sense | CCTGCCCCTTGGACTCAAGGTCACC (SEQ ID NO:4) |
| P9 | Exon 1 | Sense | GCTCAGTCCACTGTGCTCCTGCCTG (SEQ ID NO:6) |
| P10 | Exon 6 | Antisense | GGTCCACGCCTAGTCATGCTGGCC (SEQ ID NO:5) |
| P13 | 3'UTR | Antisense | GGTGCTAAAAGGTCTTCCTCTAGGAC (SEQ ID NO:7) |
| P29 | Exon 5 | Antisense | CAGTGTTAGCAAGACCAGGG (SEQ ID NO:8) |

Primers P3, P5, and P9 possess a BamHI site at their 5' end. Primers P10 and P13 possess an EcoRI site at their 5' end. The intron sequence is in lowercase.

TABLE 2

Nucleotide Sequence of Exon-Intron Boundaries in Rat OFQ Receptor Gene

| Exon | Exon Size (bp) | Sequence of Exon-Intron Junctions (5' Splice Donor . . . Intron (bp) . . . 3' Splice Acceptor) |
|---|---|---|
| 1 | 250 | GTTGGAG gtaagagggg . . . (467) . . . ccctgttccag GAACTGT (SEQ ID NO:25) |
| 2 | 257 | TCCTCAG gtaggctggg . . . (555) . . . ttttttccag CTGGGAG (SEQ ID NO:26) |
| 3 | 84 | ACAGCAG gtgaggactt . . . (1353) . . . ttcattgctag ACAATAC (SEQ ID NO:27) |
| 4 | 145 | ACATTCA gttagatatg . . . (283) . . . gtcctctacag GCACACC (SEQ ID NO:28) |
| 5 | 358 | GATGAAG gtcagtgggt . . . (81) . . . ctctcctgcag AGATCGA (SEQ ID NO:29) |
| 6 | 524 | AGCATGA (SEQ ID NO:30) |

Exon sequences are in uppercase and intron sequences are in lowercase

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in relevant fields are intended to be within the scope of the following claims.

I claim:

1. An isolated nucleic acid sequence encoding a polypeptide that binds to Orphanin FQ, wherein said nucleic acid is selected from the group consisting of SEQ ID NOs: 9, 10, 12, 14, 16, 18, 19, 20, and 21.

2. A vector comprising the nucleic acid sequence of claim 1.

3. A host cell comprising the vector of claim 2, wherein said host cell is located in vitro.

* * * * *